US006653086B1

(12) United States Patent
Behan et al.

(10) Patent No.: US 6,653,086 B1
(45) Date of Patent: Nov. 25, 2003

(54) ENDOGENOUS CONSTITUTIVELY ACTIVATED G PROTEIN-COUPLED ORPHAN RECEPTORS

(75) Inventors: Dominic P. Behan, San Diego, CA (US); Derek T. Chalmers, Solana Beach, CA (US); Chen W. Liaw, San Diego, CA (US); I Lin-Lin, San Diego, CA (US); Kevin P. Lowitz, San Diego, CA (US); Ruoping Chen, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/364,425

(22) Filed: Jul. 30, 1999

Related U.S. Application Data

(63) Continuation-in-part of application No. 09/060,188, filed on Apr. 14, 1998.
(60) Provisional application No. 60/094,879, filed on Jul. 31, 1998, provisional application No. 60/106,300, filed on Oct. 30, 1998, provisional application No. 60/110,906, filed on Dec. 4, 1998, and provisional application No. 60/121,851, filed on Feb. 26, 1999.

(51) Int. Cl.[7] ........................ C12N 15/00; C12N 16/63; C07H 21/04; G01N 33/53; C07K 14/00

(52) U.S. Cl. ........................ 435/7.1; 435/7.2; 435/7.21; 435/69.1; 435/70.1; 435/320.1; 435/172.3; 530/300; 530/350; 536/23.1; 424/192.1

(58) Field of Search ......................... 435/7.1, 7.2, 7.21, 435/69.1, 70.1, 320.1, 172.3; 530/300, 350; 536/23.1; 424/192.1

(56) References Cited

U.S. PATENT DOCUMENTS

| | | | | |
|---|---|---|---|---|
| 5,514,578 | A | 5/1996 | Hogness et al. | 435/240.2 |
| 5,532,157 | A | 7/1996 | Fink | 435/240.2 |
| 5,573,944 | A | 11/1996 | Kirschner et al. | 435/252.3 |
| 5,639,616 | A | 6/1997 | Liao et al. | 435/7.1 |
| 5,750,353 | A | 5/1998 | Kopin et al. | 435/7.21 |

FOREIGN PATENT DOCUMENTS

| | | |
|---|---|---|
| CA | 2135253 | 5/1996 |
| WO | WO 97/11159 | 9/1996 |
| WO | WO 98/46995 | 10/1998 |
| WO | WO 99/09024 | 2/1999 |

OTHER PUBLICATIONS

Bertin, B. et al., "Cellular signaling by an agonist–activated receptor/Gs–alpha fusion protein", *Proc. Natl. Acad. Sci. USA,* 1994, 91, 8827–8831.

Seifert, R. et al., Different effects of Gs alpha splice variants on beta–2–adrenoreceptor–mediated signaling, *J. Biol. Chem.,* 1998, 273, 5109–5116.

Wise, A. et al., "Rescue of functional interaations between the alpha–2A–adrenoreceptor and acylation–resistant forms of Gil–alpha aby expressing the proteins from chimerica open reading frames," *J. Biol. Chem.,* 1997, 272, 24673–24678.

Burt, A.R., et al., "Agonist occupation of an alpha–2A–adrenoreceptor–Gil–alpha fusion protein results in activation of both receptor–linked and endogenous Gi proteins", *J. Biol. Chem.,* 1997, 283, 10367–10375.

Alla, S.A. et al., "Extracellular domains of the bradykinin B2 receptor involved in ligand binding and agonist sensing defined by anti–peptide antibodies," *J. Biol. Chem.,* 1996, 271, 1748–1755.

Advenier, C. et al., "Effects on the isolated human bronchus of SR 48968, a potent and selective nonpeptide antagonist of the neurokinin A ($NK_2$) receptors," *Am. Rev. Respir. Dis.,* 1992, 146(5, Pt. 1), 1177–1181.

Alexander, W.S. et al., "Point mutations within the dimer interfact homology domain of c–Mpl induce constitutive receptor activity and tumorigenicity," *EMBO J.,* 1995, 14(22), 5569–5578.

Arvanitikis, L. et al., "Human herpesvirus KSHV encodes a constitutively active G–protein–coupled receptor linked to cell proliferation," *Nature,* 1997, 385, 347–349.

Barker, E.L. et al., "Constitutively active 5–hydroxytryptamine$_{2C}$ receptors reveal novel inverse agonist activity of receptor ligands," *J. Biol. Chem.,* 1994, 169(16), 11687–11690.

Baxter, G., "5–$HT_2$ receptors: a family re–united?" *Trends Pharmacol. Sci.,* 1995, 16, 105–110.

Besmer, P. et al., "A new acute transforming feline retrovirus and relationship of its oncogene v–kit with the protein kinase gene family," *Nature,* 1986, 320, 415–421.

Blin, N. et al., "Mapping of single amino acid residues required for selective activation of $G_{q/11}$ by the m3 muscarinic acetylcholine receptor," *J. Biol. Chem.,* 1995, 270, 17741–17748.

Bond, R.A. et al., "Inverse agonists and G–protein–coupled receptors," in *Receptor–Based Drug Design,* Leff, P. (ed.), New York, M. Dekker, 1998, 363–377.

Boone, C. et al., "Mutations that alter the third cytoplasmic loop of the a–factor receptor lead to a constitutive and hypersensitive phenotype," *Proc. Natl. Acad. Sci. USA,* 1993, 90(21), 9921–9925.

(List continued on next page.)

*Primary Examiner*—Gary Kunz
*Assistant Examiner*—Nirmal S. Basi
(74) *Attorney, Agent, or Firm*—Cozen O'Connor; Ann A. Wieczorek; Michael P. Straher

(57) ABSTRACT

Disclosed herein are techniques for directly identifying candidate compounds as agonists, partial agonists and/or, most preferably, inverse agonists, to endogenous, constitutively activated orphan G protein-coupled receptors. Such directly identified compounds can be utilized, most preferably, in pharmaceutical compositions

3 Claims, 34 Drawing Sheets

OTHER PUBLICATIONS

Burstein, E.S. et al., "Constitutive activation of chimeric m2/m5 muscarinic receptors and delineation of G–protein coupling selectivity domains," *Biochem. Pharmacol.* 1996, 51(4), 539–544.

Burstein, E.S. et al., "Amino acid side chains that define muscarinic receptor/G–protein coupling. Studies of the third intracellular loop," *J. Biol. Chem.,* 1996, 271(6), 2882–2885.

Burstein, E.S. et al., "Constitutive activation of muscarinic receptors by the G–protein $G_q$," *FEBS Lett.,* 1995, 363(3), 261–263.

Bylund, D., "International union of pharmacology nomenclature of adrenoceptors," *Pharmacol. Rev.,* 1994, 46, 121–136.

Casey, C. et al., "Constitutively active mutant 5–$HT_{2A}$ serotonin receptors: inverse agonist activity of classical 5$HT_{2A}$ antagonists," *Soc. Neurosci.,* 1996, Abstract #699.10.

Cheatham, B. et al., "Substitution of the erbB–2 oncoprotein transmembrane domain activates the insulin receptor and modulates the action of insulin–receptor substrate 1," *Proc. Natl. Acad. Sci. USA,* 1993, 90, 7336–7340.

Chen, J. et al., "Tethered Ligand Library for Discovery of Peptide Agonists," *J. Biol. Chem.,* 1995, 270, 23398–23401.

Chen, T.S. et al., "Microbial hydroxylation and glucuronidation of the angiotensin II (AII) receptor antagonist MK 954," *J. Antibiot.* (*Tokyo*), 1993, 46(1), 131–134.

Chen, W. et al., "A colorimetric assay for measuring activation of $G_s$– and $G_q$–coupled signaling pathways," *Anal. Biochem.,* 1995, 226(2), 349–354.

Chidiac, P. et al., "Inverse agonist activity of β–adrenergic antagonists," *J. Pharm. Exp. Ther.,* 1994, 45, 490–499.

Clozel, M. et al., "In vivo pharmacology of Ro 46–2005, the first synthetic nonpeptide endothelin receptor antagonist: implications for endothelin physiology," *J. Cardiovas. Pharmacol.,* 1993, 22(Suppl. 8), S377–S379.

Collesi, C. et al., "A splicing variant of the RON transcript induces constitutive tyrosine kinase activity and an invasive phenotype," *Mol. Cell. Biol.,* 1996, 16(2), 5518–5526.

Cooper, C.S. et al., "Molecular cloning of a new transforming gene from a chemically transformed human cell line," *Nature,* 1984, 311, 29–33.

De Dios, I. et al., "Effect of L–364,718 (CCK Receptor Antagonist) on Exocrine Pancreatic Secretion of Hydrocortison–Treated Rats," *Pancreas,* 1994, 9(2), 212–218.

Desbios–Mouthon, C. et al., "Deletion of $Asn^{281}$ in the α–subunit of the human insulin receptor causes constitutive activation of the receptor and insulin desensitization," *J. Clin. Endocrinol. Metab.,* 1996, 81(2), 719–727.

Di Renzo, M.F. et al., "Expression of the Met/HGF receptor in normal and neoplastic human tissues," *Oncogene,* 1991, 6(11), 1997–2003.

Di Renzo, M.F. et al., "Overexpression of the c–MET/HGF receptor gene in human thyroid carcinomas," *Oncogene,* 1992, 7, 2549–2553.

Duprez, L. et al., "Germline mutations of the thyrotropin receptor gene cause non–autoimmune autosomal dominant hyperethyroidism," *Nature Genetics,* 1994, 7, 396–401.

Eggericksx, D. et al., "Molecular Cloning of an Orphan G–Protein–Coupled Receptor that Constitutively Activates Adenylate Cyclase," *Biochem. J.,* 1995, 309, 837–843.

Evans, B.E. et al., "Orally Active, Nonpeptide Oxytocin Antagonists," *J. Med. Chem.,* 1992, 35, 3919–3927.

Fu, M. et al., "Functional autoimmune epitope on $\alpha_1$–adrenergic receptors in patients with malignant hypertension," *Lancet,* 1994, 344, 1660–1663.

Furitsu, T. et al., "Identification of Mutations in the Coding Sequence of the Proto–oncogene c–kit in a Human Mast Cell Leukemia Cell Line Causing Ligand–independent Activation of c–kit Product," *J. Clin. Invest.,* 1993, 92, 1736–1744.

Gellai, M. et al., "Nonpeptide Endothelin Receptor Antagonists V: Prevention and Reversal of Acute Renal Failure in the Rat by SB 209670," *J. Pharm. Exp. Therap.,* 1995, 275(1), 200–206.

Gitter, B. et al., "Pharmacological Characterization of LY303870: A Novel Potent and Selective Nonpeptide Substance P (Neurokinin–1) Receptor Antagonist," *J. Pharm. Exp. Therp.,* 1995, 275(2), 737–744.

Gouilleux–Gruart, V. et al., "STAT–Related Transcription Factors are Constitutively Activated in Peripheral Blood Cells from Acute Leukemia Patients," *Blood,* 1996, 87(5), 1692–1697.

Hansson, J.H. et al., "Hypertension caused by a truncated epithelial sodium channel γ subunit: genetic heterogeneity of Liddle syndrome," *Nat. Genet.,* 1995, 11(1), 76–82.

Hasegawa, H. et al., "Two Isoforms of the Prostaglandin E Receptor EP3 Subtype Different in Agonist–independent Constitutive Activity," *J. Biol. Chem.,* 1996, 271(4), 1857–1860.

Hendler, F. et al., "Human Squamous Cell Lung Cancers Express Increased Epidermal Growth Factor Receptors," *J. Clin. Invest.,* 1984, 74, 647–651.

Herrick–Davis, K. et al., "Constitutively Active 5HT2C Serotonin Receptor Created by Site–Directed Mutagenesis," *Soc. Neurosci.,* 1996 Abstract No. 699.18.

Hieble, J., "International union of pharmacology. X. Recommendation for nomenclature of 1–adrenoceptors," *Pharm. Rev.,* 1995, 47, 267–270.

Hill, S., "Distribution, Properties, and Functional Characteristics of Three Classes of Histamine Receptor," *Am. Soc. Pharm. Exp. Therap.,* 1990, 42(1), 45–83.

Högger, P. et al., "Activating and Inactivating Mutations in—and C–terminal i3 Loop Junctions of Muscarinic Acetylcholine Hm1 Receptors," *J. Biol. Chem.,* 1995, 270(13), 7405–7410.

Ikeda, H. et al., "Expression and Functional Role of the Proto–oncogene c–kit in Acute Myeloblastic Leukemia Cells," *Blood,* 1991, 78(11), 2962–2968.

Imura, R. et al., "Inhibition by HS–142–1, a novel nonpeptide atrial natriuretic peptide antagonist of microbial origin, of atrial natriuretic peptide–induced relaxation of isolated rabbit aorta through the blockade of guanylyl cyclase–linked receptors," *Mol. Pharm.,* 1992, 42, 982–990.

Jakubik, J. et al., "Constitutive activity of the $M_1$–$M_4$ subtypes of muscarinic receptors in transfected CHO cells and of muscarinic receptors in the heart cells revealed by negative antagonists," *FEBS Letts.,* 1995, 377, 275–279.

Kjelsberg, M.A. et al., "Constitutive activation of the $\alpha_{1B}$–adrenergic receptor by all amino acid substitutions at a single site," *J. Biol. Chem.,* 1992, 267(3), 1430–1433.

Knapp, R. et al., "Molecular biology and pharmacology of cloned opioid receptors," *FASEB J.,* 1995, 9, 516–525.

Kosugi, S. et al., "Characterization of heterogeneous mutations causing constitutive activation of the luteinizing hormone receptor in familial male precocious puberty," *Human Mol. Genetics,* 1995, 4(2), 183–188.

Kosugi, S. et al., "Identification of Thyroid–Stimulating Antibody–Specific Interaction Sites in the N–Terminal Region of the Thyrotropin Receptor," *Mol. Endocrinology,* 1993, 7, 114–130.

Kraus, M. et al., "Demonstration of ligand–dependent signaling by the erbB–3 tyrosine kinase and its constitutive activation in human breast tumor cells," *Proc. Natl. Acad. Sci. USA,* 1993, 90, 2900–2904.

Kudlacz, E. et al., "In Vitro and In Vivo Characterization of MDL 105,212A, a Nonpeptide NK–1/NK–2 Tachykinin Receptor Antagonist," *J. Pharm. Exp. Therap.,* 1996, 277(2), 840–851.

Kuriu, A., et al., "Proliferation of Human Myeloid Leukemia Cell Line Associated with the Tyrosine–Phosphorylation and Activation of the Proto–oncogene c–kit Product," *Blood,* 1991, 78(11), 2834–2840.

Labbé–Jullié, C. et al., "Effect of the nonpeptide neurotensin antagonist, SR 48692, and two enantiomeric analogs, SR 48527 and SR 49711, on neurotension binding and contractile responses in guinea pig ileum and colon," *J. Pharm. Exp. Therap.,* 1994, 271(1), 267–276.

Latronico, A. et al., "A novel mutation of the luteinizing hormone receptor gene causing male gonadotropin–independent precocious puberty," *J. Clin. Endocrinol. Metabl.,* 1995, 80(8), 2490–2494.

Laue, L. et al., "Genetic heterogeneity of constitutively activating mutations of the human luteinizing hormone receptor in familial male–limited precocious puberty," *Proc. Natl. Acad. Sci USA,* 1995, 92, 1906–1910.

Løvlie, R. et al., "$Ca^{2+}$–sensing receptor gene (PACR1) mutation T151M in isolated autosomal dominant hypoparathyroidism," *Hum. Genet,* 1996, 98, 129–133.

Lefkowitz, R. et al., "Constitutive activity of receptors coupled to guanine nucleotide regulatory proteins," *Trends Pharmacol. Sci.,* 1993, 14, 303–307.

Libermann, T. et al., "Amplification, enhanced expression and possible rearrangement of EGF receptor gene in primary human brain tumours of glial origin," *Nature,* 1985, 313, 144–147.

Liu, C. et al., "Overexpression of c–met proto–oncogene but not epidermal growth factor receptor or c–erbB–2 in primary human colorectal carcinomas," *Oncogene,* 1992, 7, 181–185.

Liu, J. et al., "Molecular mechanisms involved in muscarinic acetylcholine receptor–mediated G protein activation studied by insertion mutagenesis," *J. Biol. Chem.,* 1996, 271(11), 6172–6178.

Lonardo, F. et al., "The normal erbB–2 product is an atypical receptor–like tyrosine kinase with constitutive activity in the absence of ligand," *New Biologist,* 1990, 2(11), 992–1003.

Maenhaut, C. et al., "RDC8 codes for an adenosine A2 receptor with physiological constitutive activity," *Biochem. Biophys. Res. Comm.,* 1990, 173(3), 1169–1178.

Mann, J. et al., "Increased serotonin$_2$ and β–adrenergic receptor binding in the frontal cortices of suicide victims," *Arch. Gen. Psychiatry,* 1986, 43, 954–959.

Martone, R.L. et al., "Human CRF receptor chimeras: Mapping of ligand binding determinants," 26th Meeting of the Society of Neuroscience, Washington, D.C. Nov. 16–21, 1996, Abstract No. 609.8.

Magnusson, Y. et al., "Autoimmunity in idiopathic dilated cardiomyopathy," *Circulation,* 1994, 89, 2760–2767.

Matus–Leibovitch, N. et al., "Truncation of the thyrotropin–releasing hormone receptor carboxyl tail causes constitutive activity and leads to impaired responsiveness in Xenopus Oocytes and AtT20 Cells," *J. Biol. Chem.,* 1995, 270(3), 1041–1047.

Myles, G.M. et al., "Tyrosine 569 in the c–Fms juxtamembrane domain is essential for kinase activity and macrophage colony–stimulating factor–dependent internalization," *Mol. Cell. Biol.,* 1994, 14(7), 4843–4854.

Nanevicz, T. et al., "Thrombin receptor activating mutations," *J. Biol. Chem.,* 1996, 271(2), 702–706.

Natali, P.G. et al., "Expression of the c–Met/HGF receptor in human melanocytic neoplasms: demonstration of the relationship to malignant melanoma tumour progression," *Br. J. Cancer,* 1993, 68, 746–749.

Neilson, K.M. et al., "Constitutive activation of fibroblast growth factor receptor–2 by a point mutation associated with Crouzon syndrome," *J. Biol. Chem.,* 1995, 270(44), 26037–26040.

Oda, S. et al., "Pharmacological profile of HS–142–1, a novel nonpeptide atrial natriuretic peptide (ANP) antagonist of microbial origin. II. Restoration by HS–142–1 of ANP–induced inhibition of aldosterone production in adrenal glomerulosa cells," *J. Pharm. Exp. Ther.,* 1992, 263(1), 241–245.

O'Dowd, B.F. et al., "Site–directed mutagenesis of the cytoplasmic domains of the human β2–adrenergic receptor," *J. Biol. Chem.,* 1988, 263(31), 15985–15992.

Offermans, S. et al., "$G\alpha_{15}$ and $G\alpha_{16}$ Couple a Wide Variety of Receptors to Phospholipase C," *J. Biol. Chem.,* 1995, 270, 15175–15180.

Palkowitz, A.D. et al., "Structural evolution and pharmacology of a novel series of triacid angiotensin II receptor antagonists," *J. Med. Chem.,* 1994, 37, 4508–4521.

Parent, J. et al., "Mutations of two adjacent amino acids generate inactive and constitutively active forms of the human platelet–activating factor receptor," *J. Biol. Chem.,* 1996, 271(14), 7949–7955.

Parfitt, A.M. et al., "Hypercalcemia due to constitutive activity of the parathyroid hormone (PTH)/PTH–related peptide receptor: comparison with primary hypoparathyroidism," *J. Clin. Endocr. Metabl.,* 1996, 81, 3584–3588.

Parma, J. et al., "Somatic mutations in the thyrotropin receptor gene cause hyperfunctioning thyroid adenomas," *Nature,* 1993, 365, 649–651.

Pei, G. et al., "A constitutive active mutant $\beta_2$–adrenergic receptor is constitutively desensitized and phosphorylated," *Proc. Natl. Acad. Sci. USA,* 1994, 91, 2699–2702.

Pendley, C.E. et al., "The gastrin/cholecystokinin–B receptor antagonist L–365,260 reduces basal acid secretion and prevents gastrointestinal damage induced by aspirin, ethanol and cysteamine in the rat," *J. Pharmacol. Exp. Ther.,* 1993, 265(3), 1348–1354.

Peroutka, S., "Serotonin receptor subtypes. Their evolution and clinical relevance," *CNS Drugs,* 1995, 4 (*Suppl. 1*), 18–27.

Pettibone, D.J. et al., "Development and pharmacological assessment of novel peptide and nonpeptide oxytocin antagonists," *Regul. Pept.,* 1993, 45, 289–293.

Prat, M.P. et al., "The receptor encoded by the human c–Met oncogene is expressed in hepatocytes, epithelial cells and solid tumors," *Int. J. Cancer,* 1991, 49, 323–328.

Prezeua, L. et al., "Changes in the carboxy–terminal domain of metabotropic glutamate receptor 1 by alternate splicing generate receptors with differing agonist–independent activity," *Mol. Pharmacol.,* 1996, 49, 422–429.

Rakovska, A. et al., "Effect of loxiglumide (CR 1505) on CCK–induced contractions and $^3$H–acetylcholine release from guinea–pig gallbaldder," *Neuropeptides,* 1993, 25(5), 271–276.

Ren, Q. et al., "Constitutive active mutants of the $\alpha_2$–adrenergic receptor," *J. Biol. Chem.,* 1993, 268, 16483–16487.

Reynolds, E.E. et al., "Pharmacological characterization of PD 156707, an orally active $ET_A$ receptor antagonist," *J. Pharmacol. Exp. Ther.,* 1995, 273(3), 1410–1417.

Robbins, L.S. et al., "Pigmentation phenotypes of variant extension locus alleles result from point mutations that alter MSH receptor function," *Cell,* 1993, 72, 827–834.

Rong, S. et al., "Met expression and sarcoma tumorigenicity," *Cancer,* 1993, 53(22), 5355–5360.

Samama, P. et al., "A mutation–induced activation state of the β2–adrenergic receptor," *J. Biol. Chem.,* 1993, 268(7), 4625–4636.

Sautel, M. et al., "Neuropeptide Y and the nonpeptide antagonist BIBP 3226 share an overlapping binding site at the human Y1 receptor," *Am. Soc. Pharm. Exp. Ther.,* 1996, 50, 285–292.

Sawutz, D.G. et al., "Pharmacology and structure–activity relationships of the nonpeptide bradykinin receptor antagonist WIN 64338," *Can. J. Physiol. Pharmacol.,* 1995, 73, 805–811.

Scheer, A. et al., "Constitutively active G protein–coupled receptors: potential mechanisms of receptor activation," *J. Rec. Signal Transduct. Res.,* 1997, 17(1–3), 57–73.

Scheer, A. et al., "The activation process of the $\alpha_{1B}$–adrenergic receptor: Potential role of protonation and hydrophobicity of a highly conserved aspartate," *Proc. Natl. Acad. Sci. USA,* 1997, 94, 808–813.

Schwinn, D.A. et al., "Cloning and pharmacological characterization of human Alpha–1 adrenergic receptors: sequence corrections and direct comparison with other species homologues," *J. Pharmacol.,* 1995, 272(1), 134–142.

Schild, L. et al., "A mutation in the epithelial sodium channel causing Liddle disease increases channel activity in the *Xenopus laevis* oocyte expression system," *Proc. Natl. Acad. Sci. USA,* 1995, 92, 5699–5703.

Seeman, P. et al., "Dopamine receptor pharmacology," *Trends Pharmacol. Sci.,* 1994, 15, 264–270.

Seeman, P. et al., "Dopamine D4 receptors elevated in schizophrenia," *Nature,* 1993, 365, 441–445.

Serradeil–Le Gale, C. et al., "Biochemical and pharmacological properties of SR 49059, a new, potent, nonpeptide antagonist of rat and human vasopressin $V_{1a}$ receptors," *J. Clin. Invest.,* 1993, 92, 224–231.

Sharif, M. et al., "Malignant transformation by G protein–coupled hormone receptors," *Mol. Cell. Endocrinology,* 1994, 100, 115–119.

Showers, M.O. et al., "Activation of the erythropoietin receptor by the Friend spleen focus–forming virus gp55 glycoprotein induces constitutive protein tyrosine phosphorylation," *Blood,* 1992, 80(12), 3070–3078.

Skinner, R.H. et al., "Direct measurement of the binding of RAS to neurofibromin using scintillation proximity assay," *Anal. Biochem.,* 1994, 223, 259–265.

Slamon, D.J. et al., "Human breast cancer: correlation of relapse and survival with amplification of the HER–2/neu oncogene," *Science,* 1987, 235, 177–181.

Slamon, D. et al., "Studies of the HER–2/neu proto–oncogene in human breast and ovarian cancer," *Science,* 1989, 244, 707–712.

Salomon, Y. et al., "A highly sensitive adenylate cyclase assay," *Anal. Biochem.,* 1974, 58, 541–548.

Spiegel, A.M., "Defects in G protein–coupled signal transduction in human disease," *Ann. Rev. Physiol.,* 1995, 58, 143–170.

ter Laak, A. et al., "Modelling and mutation studies on the histamine $H_1$–receptor agonist binding site reveal different binding modes for $H_1$–agonists: $Asp^{116}$ (TM3) has a constitutive role in receptor stimulation," *J. Computer–Aided Mol. Design,* 1995, 9, 319–330.

Tiberi, M. et al., "High agonist–independent activity is a distinguishing feature of the dopamine D1B receptor subtype," *J. Biol. Chem.,* 1994, 269(45), 27925–27931.

Tsujimura, T. et al., "Constitutive activation of c–kit in FMA3 murine mastocytoma cells caused by deletion of seven amino acids at the juxtamembrane domain," *Blood,* 1996, 87(1), 273–283.

Wang, Z. et al., "Constitutive $\mu$ opioid receptor activation as a regulatory mechanism underlying narcotic tolerance and dependence," *Life Sci.,* 1994, 54(20), 339–350.

Watowich, S.S. et al., "Homodimerization and constitutive activation of the erythropoietin receptor," *Proc. Natl. Acad. Sci USA,* 1992, 89, 2140–2144.

Weber–Nordt, R.M. et al., "Constitutive activation of STAT proteins in primary lymphoid and myeloid leukemia cells and in Epstein–Barr virus (EBV)–related lymphoma cell lines," *Blood,* 1996, 88(3), 809–816.

Webster, M.K. et al., "Constitutive activation of fibroblast growth factor receptor 3 by the transmembrane point mutation found in achondroplasia," *EMBO J.,* 1996, 14, 520–527.

Xu, Y. et al., "Characterization of epidermal growth factor receptor gene expression in malignant and normal human cell lines," *Proc. Natl. Acad. Sci. USA,* 1984, 81, 7308–7312.

Yamada, K. et al., "Substitution of the insulin receptor transmembrane domain with the c–neu/erbB2 transmembrane domain constitutively activates the insulin receptor kinas in vitro," *J. Biol. Chem.,* 1992, 267(18), 12452–12461.

Zhang, S. et al., "Identification of Dynorphins as Endogenous Ligands for an Opioid Receptor–Like Orphan Receptor," *J. Biol. Chem.,* 1995, 270, 22772–22776.

Zhen, Z. et al., "Structural and functional domains critical for constitutive activation of the HGF–receptor (Met)," *Oncogene,* 1994, 9, 1691–1697.

Gantz, I. et al., "Molecular Cloning of a Novel Melanocortin Receptor," *J. Biol. Chem.,* 1993, 268(11), 8246–8250.

Heiber, M. et al., "Isolation of Three Novel Human Genes Encoding G Protein–Coupled Receptors," *DNA and Cell Biology,* 1995, 14(1), 25–35.

Howard, A.D. et al., "A Receptor in Pituitary and Hypothalamus That Functions in Growth Hormone Release," *Science,* 1996, 273, 974–977.

Iismaa, T.P. et al., "Isolation and Chromosomal Localization of a Novel Human G–Protein–Coupled Receptor (GPR3) Expressed Predominantly in the Central Nervous System," *Genomics,* 1994, 24, 391–394.

Itoh, H. et al., "Molecular cloning and sequence determination of cDNAs for α subunits of the guanine nucleotide–binding proteins $G_s$, $G_i$, and $G_o$ from rat brain," *Proc. Natl. Acad. Sci. USA,* 1986, 83, 3776–3780.

Jensen et al., "mRNA Profiling of Rat Islet Tumors Reveals Nkx 6.1 as a β–Cell–specific Homeodomain Transcription Factor," *J. Biol. Chem.,* 1996, 271(31), 18749–18758.

Konig et al., "Method for Identifying Ligands That Bind to Cloned $G_s$– or $G_i$–Coupled Receptors," *Mol. Cell. Neuro.,* 1991, 2, 331–337.

Leonard, J. et al., "The LIM family transcription factor Isl–1 requires cAMP response element binding protein to promote somatostatin expression in pancreatic islet cells," *Proc. Natl. Acad. Sci. USA,* 1992, 89, 6257–6251.

Marchese, A. et al., "Cloning of Human Genes Encoding Novel G Protein–Coupled Receptors," *Genomics,* 1994, 23, 609–618.

Marks, D.L. et al., "Simultaneous Visualization of Two Cellular mRNA Species in Individual Neurons by Use of a New Double in Situ Hybridization Method," *Mol. & Cell. Neuro.,* 1992, 3, 395–405.

O'Dowd, B., et al., "Cloning and chromosomal mapping of four putative novel human G–protein–coupled receptor genes," *Gene,* 1997, 187, 75–81.

Sakurai T. et al., "Orexins and Orexin Receptors: A Family of Hypothalamic Neuropeptides and G Protein–Coupled Receptors that Regulate Feeding Behavior," *Cell,* 1998, 92, 573–585.

Song, Z.–H. et al., "Molecular Cloning and Chromosomal Localization of Human Genes Encoding Three Closely Related G Protein–Coupled Receptors," *Genomics,* 1995, 28, 347–349.

Suzuki, M. et al., "Regulatable Promoters for Use in Gene Therapy Applications: Modification of the 5'–Flanking Region of the CFTR Gene with Multiple cAMP Response Elements to Support Basal, Low–Level Gene Expression that can be Unregulated by Exogenous Agents that Raise Intracellular Levels of cAMP," *Human Gene Therapy,* 1996, 7, 1883–1893.

Xu, Y. et al., "Identification of Human OGR1, a Novel G Protein–Coupled Receptor That Maps to Chromosome 14," *Genomics,* 1996, 35, 397–402.

Gdaniec, M., et al., "Crystal and molecular structure of 3–(4–chlor=benzoylimino)–5,6–dihydro–3H–imidazo[2, 1–c]–1,2,4–dithiazole," *Chemical Abstracts XP–002177674,* 1986, 111(20), 1 page.

Gdaniec, M., et al., "Crystal and molecular structure of 3–(4–chlorobenzoylimino)–5,6–dih ydro–3H–imidazo[2, 1–c]–1,2,4–dithiazole," *Chemical Abstracts XP–002177676,* 1989, 19(3), 1 page.

Saczewaki, F., "Synthesis, transformations and tuberculostatic activity of 1–(N–aroylthiocarbamoyl)imidazolidine–2–thiones," *Chemical Abstracts XP–002177673,* 1993, 121(7), 1 page.

Saczewski, F., "Synthesis, transformations and tuberculostatic activity ofl–aroylthiocarbamoyl)imidazolidine–2–thiones," *Chemical Abstracts XP–002177675,* 1993, 1 page.

Saczewski, F., et al., "Synthesis and transformations of 3–benzoylimino–5,6–dihydro–3H–imidazo[2,1–c][1,2,4] dithiazole," *Communications,* Sep. 1986, 751–753.

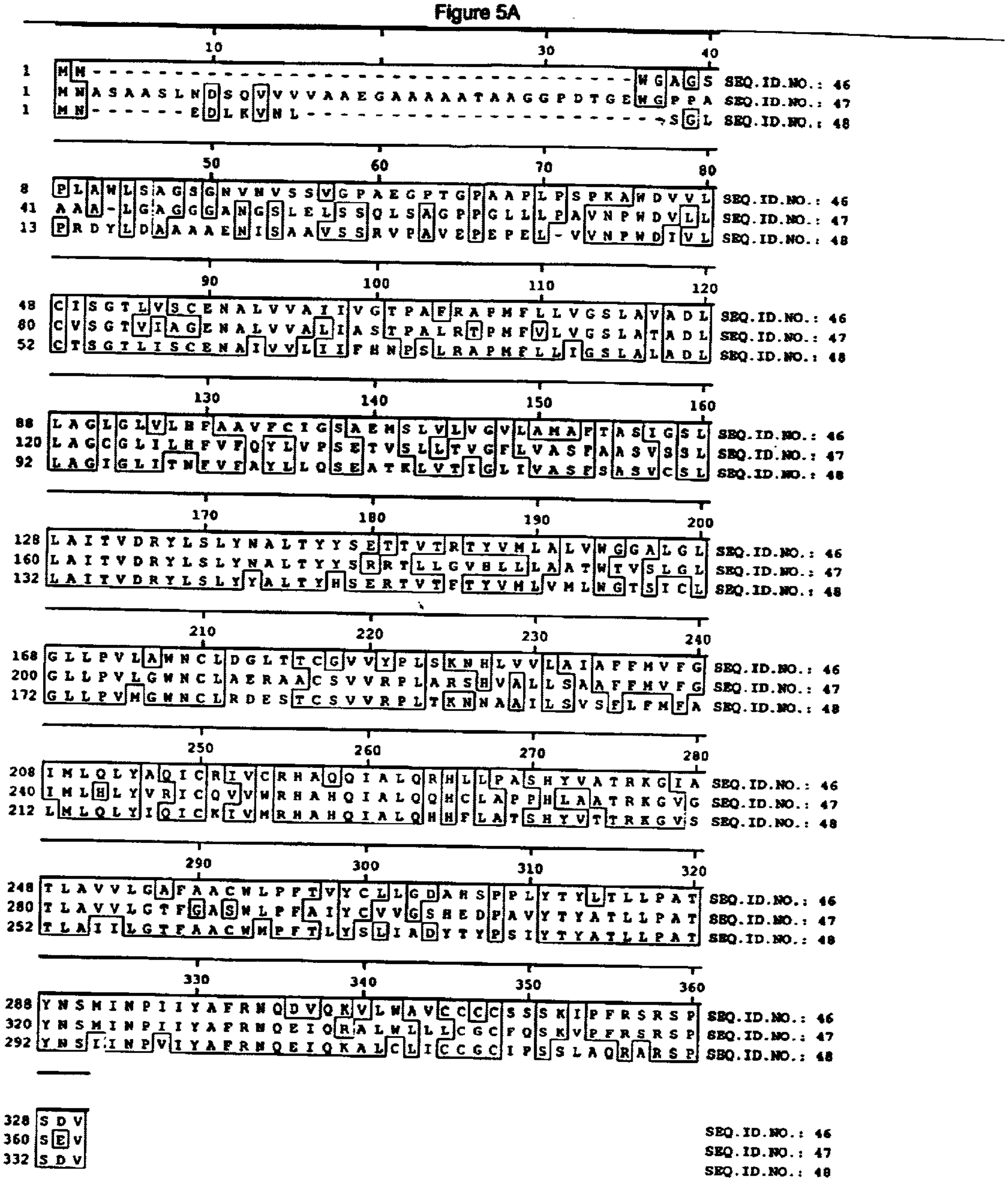

Figure 5A

```
              10                      30               40
1   M N - - - - - - - - - - - - - - - - - - - - - - - W G A G S      SEQ.ID.NO.: 46
1   M N A S A A S L N D S Q V V V A A E G A A A A A T A A G G P D T G E W G P P A   SEQ.ID.NO.: 47
1   M N - - - - - E D L K V N L - - - - - - - - - - - - - - - - - → S G L          SEQ.ID.NO.: 48

              50              60              70              80
8   P L A W L S A G S G N V H V S S V G P A E G P T G P A A P L P S P K A W D V V L   SEQ.ID.NO.: 46
41  A A A - L G A G G A N G S L E L S S Q L S A G P P G L L P A V N P W D V L L      SEQ.ID.NO.: 47
13  P R D Y L D A A A A E N I S A A V S S R V P A V E P E P E L - V V N P W D I V L   SEQ.ID.NO.: 48

              90             100             110             120
48  C I S G T L V S C E N A L V V A I I V G T P A F R A P M F L L V G S L A V A D L   SEQ.ID.NO.: 46
80  C V S G T V I A G E N A L V V A L I A S T P A L R T P M F V L V G S L A T A D L   SEQ.ID.NO.: 47
52  C T S G T L I S C E N A I V V L I I F H N P S L R A P M F L L I G S L A L A D L   SEQ.ID.NO.: 48

             130             140             150             160
88  L A G L G L V L H F A A V F C I G S A E H S L V L G V L A M A F T A S I G S L    SEQ.ID.NO.: 46
120 L A G C G L I L H F V F Q T L V P S E T V S L L T V G F L V A S F A S V S S L    SEQ.ID.NO.: 47
92  L A G I G L I T M F V F A Y L Q S E A T K L V T I G L I V A S F S H S V C S L    SEQ.ID.NO.: 48

             170             180             190             200
128 L A I T V D R Y L S L Y N A L T Y Y S E T V T R T Y V M L A L V W G G A L G L    SEQ.ID.NO.: 46
160 L A I T V D R Y L S L Y N A L T Y Y S R R T L L G V H L L A A T W T V S L G L    SEQ.ID.NO.: 47
132 L A I T V D R Y L S L Y A L T Y H S E R T V T F T Y V M L V M L W G T S I C L    SEQ.ID.NO.: 48

             210             220             230             240
168 G L L P V L A W N C L D G L T C G V V Y P L S K N H L V V L A I A F F M V F G    SEQ.ID.NO.: 46
200 G L L P V L G W N C L A E R A A C S V V R P L A R S H V A L L S A A F F M V F G   SEQ.ID.NO.: 47
172 G L L P V H G W N C L R D E S T C S V V R P L T K N N A A I L S V S F L F M F A   SEQ.ID.NO.: 48

             250             260             270             280
208 I M L Q L Y A Q I C R I V C R H A Q Q I A L Q R H L L P A S H Y V A T R K G I A   SEQ.ID.NO.: 46
240 I M L H L Y V R I C Q V V W R H A H Q I A L Q Q H C L A P P H L A A T R K G V G   SEQ.ID.NO.: 47
212 L M L Q L Y I Q I C K I V M R H A H Q I A L Q H H F L A T S H Y V T T R K G V S   SEQ.ID.NO.: 48

             290             300             310             320
248 T L A V V L G A F A A C W L P F T V Y C L L G D A H S P L Y T Y L T L L P A T     SEQ.ID.NO.: 46
280 T L A V V L G T F G A S W L P F A I Y C V V G S H E D P A V Y T Y A T L L P A T   SEQ.ID.NO.: 47
252 T L A I I L G T F A A C W M P F T L Y S L I A D Y T Y P S I Y T Y A T L L P A T   SEQ.ID.NO.: 48

             330             340             350             360
288 Y N S M I N P I I Y A F R N Q D V Q K V L W A V C C C S S S K I P F R S R S P     SEQ.ID.NO.: 46
320 Y N S M I N P I I Y A F R N Q E I Q R A L W L L L C G C F Q S K V P F R S R S P   SEQ.ID.NO.: 47
292 Y N S I I N P V I Y A F R N Q E I Q K A L C L I C C G C I P S S L A Q R A R S P   SEQ.ID.NO.: 48

328 S D V                                                             SEQ.ID.NO.: 46
360 S E V                                                             SEQ.ID.NO.: 47
332 S D V                                                             SEQ.ID.NO.: 48
```

Figure 5B

```
                    10                  20                  30                  40
  1  M N E S R W T E W R I L N M S S G I V N V S E R H S C P L G F G H Y S V V D V C   SEQ.ID.NO.: 19
  1  M N S T - - - - - - - - L D - - - - - - G N Q S S H P F C L L A F G Y - - - - - - -   SEQ.ID.NO.: 15

                    50                  60                  70                  80
 41  I F E T V V I V L L T F L I I - - - - - - - - - A G N L T V I F V F H C A P L L H   SEQ.ID.NO.: 19
 22  - L E T V N F C L L E V L I I V F L T V L I I S G N I I V I F V F H C A P L L N   SEQ.ID.NO.: 15

                    90                  100                 110                 120
 73  H Y T T S Y F I Q T M A Y A D L F V G V S C L V P T L S L L H Y S T G V H E S L   SEQ.ID.NO.: 19
 61  H H T T S Y F I Q T M A Y A D L F V G V S C V V P S L S L L H H P L P V E E S L   SEQ.ID.NO.: 15

                    130                 140                 150                 160
113  T C Q V F G Y I I S V L K S V S M A C L A C I S V D R Y L A I T K P L S Y N Q L   SEQ.ID.NO.: 19
101  T C Q I F G F V V S V L K S V S M A S L A C I S I D R Y I A I T K P L T Y N T L   SEQ.ID.NO.: 15

                    170                 180                 190                 200
153  V T P C R L R I C I I L I W I Y S C L I F L P S F F G W G K P G Y H G D I F E W   SEQ.ID.NO.: 19
141  V T P W R L R L C I F L I W L Y S T L V F L P S F F H W G K P G Y H G D V F Q W   SEQ.ID.NO.: 15

                    210                 220                 230                 240
193  C A T S W L T S A Y F T G F I V C L L Y A P A A F V V C F T Y F H I F K I C R Q   SEQ.ID.NO.: 19
181  C A E S W H T D S Y F T L F I V M M L Y A P A A L I V C F T Y F N I F R I C Q Q   SEQ.ID.NO.: 15

                    250                 260                 270                 280
233  H T K E I N D R R A R F P S H E V D S S R E T G H S P D R R Y A M V L F R I T S   SEQ.ID.NO.: 19
221  H T K D I S E R Q A R F S S Q S G E T G - E V Q A C P D K R Y A M V L F R I T S   SEQ.ID.NO.: 15

                    290                 300                 310                 320
273  V F Y M L W L P Y I I Y F L L E S S R V L D N P T L S F L T T W L A I S N S F C   SEQ.ID.NO.: 19
260  V F Y I L W L P Y I I Y F L L E S S T G H S N R F A S F L T T W L A I S N S F C   SEQ.ID.NO.: 15

                    330                 340                 350                 360
313  N C V I Y S L S N S V F R L G L R R L S E T M C T S C M C V K D Q E A Q E P - -   SEQ.ID.NO.: 19
300  N C V I Y S L S N S V F Q R G L K R L S G A M C T S C - - A S Q T T A N D P Y T   SEQ.ID.NO.: 15

                    370
351  - K P R K R A N S C S I                                                          SEQ.ID.NO.: 19
338  V R S K G P L N G C H I                                                          SEQ.ID.NO.: 15
```

VTA

Substantia Nigra
(compacta)

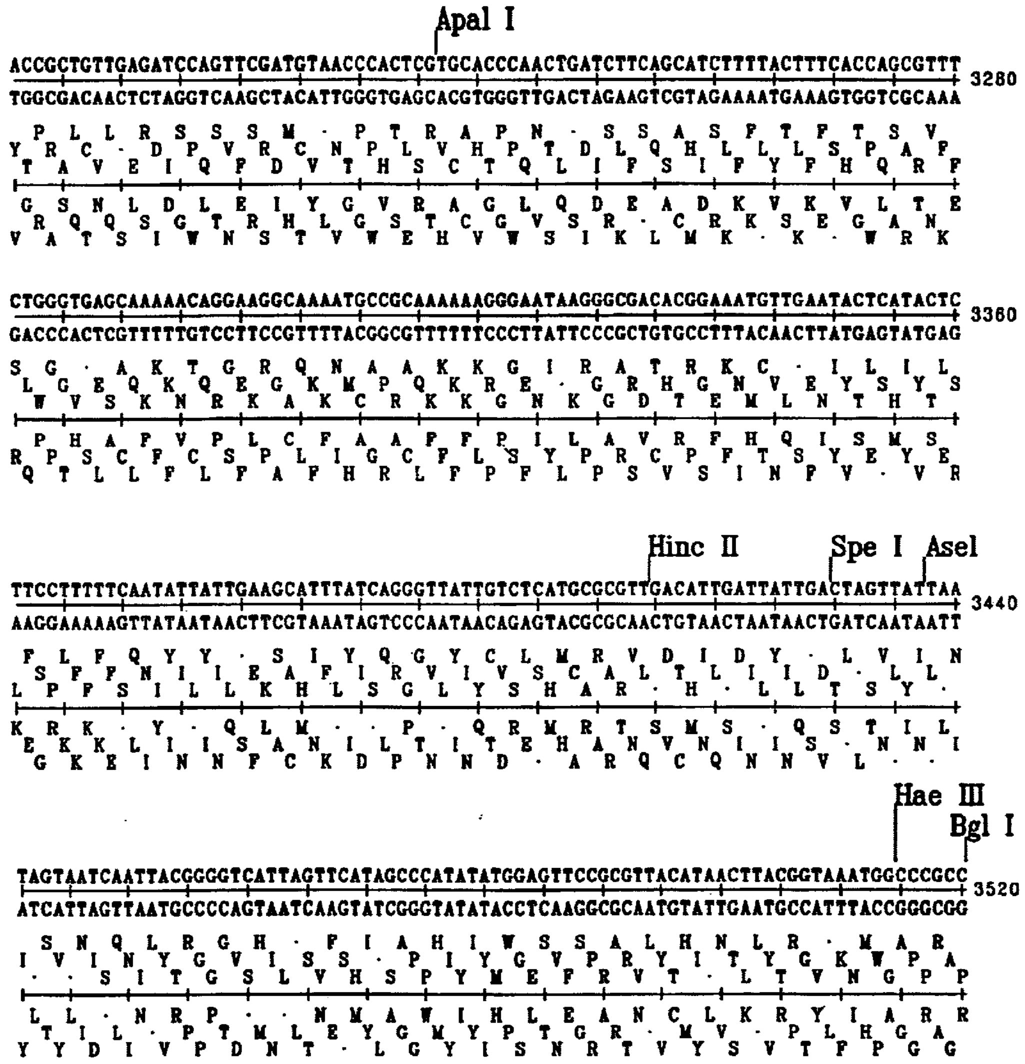

FIG. 18J

```
                                                 Apa1 I
ACCGCTGTTGAGATCCAGTTCGATGTAACCCACTCGTGCACCCAACTGATCTTCAGCATCTTTTACTTTCACCAGCGTTT
                                                                                  3280
TGGCGACAACTCTAGGTCAAGCTACATTGGGTGAGCACGTGGGTTGACTAGAAGTCGTAGAAAATGAAAGTGGTCGCAAA
      P  L  L  R  S  S  S  M  .  P  T  R  A  P  N  .  S  S  A  S  F  T  F  T  S  V
   Y  R  C  .  D  P  V  R  C  N  P  L  V  H  P  T  D  L  Q  H  L  L  L  S  P  A  F
      T  A  V  E  I  Q  F  D  V  T  H  S  C  T  Q  L  I  F  S  I  F  Y  F  H  Q  R  F
      G  S  N  L  D  L  E  I  Y  G  V  R  A  G  L  Q  D  E  A  D  K  V  K  V  L  T  E
   V  A  T  S  I  W  N  S  T  V  W  E  H  V  W  S  I  K  L  M  K  .  K  .  W  R  K
      R  Q  Q  S  G  T  R  H  L  G  S  T  C  G  V  S  R  .  C  R  K  S  E  G  A  N

CTGGGTGAGCAAAAACAGGAAGGCAAAATGCCGCAAAAAAGGGAATAAGGGCGACACGGAAATGTTGAATACTCATACTC
                                                                                  3360
GACCCACTCGTTTTTGTCCTTCCGTTTTACGGCGTTTTTTCCCTTATTCCCGCTGTGCCTTTACAACTTATGAGTATGAG
   S  G  .  A  K  T  G  R  Q  N  A  A  K  K  G  I  R  A  T  R  K  C  .  I  L  L  L
      L  G  E  Q  K  Q  E  G  K  M  P  Q  K  R  E  .  G  R  H  G  N  V  E  Y  S  Y  S
   W  V  S  K  N  R  K  A  K  C  R  K  K  G  N  K  G  D  T  E  M  L  N  T  H  T
      R  P  S  C  F  C  S  P  L  I  G  C  F  L  S  Y  P  R  C  P  F  T  S  Y  E  Y  E
   P  H  A  P  V  P  L  C  F  A  A  F  F  P  I  L  A  V  R  F  H  Q  I  S  M  S
      Q  T  L  L  F  L  P  A  F  H  R  L  F  P  F  L  P  S  V  S  I  N  P  V  .  V  R

                                           Hinc II        Spe I Ase I
TTCCTTTTTCAATATTATTGAAGCATTTATCAGGGTTATTGTCTCATGCGCGTTGACATTGATTATTGACTAGTTATTAA
                                                                                  3440
AAGGAAAAAGTTATAATAACTTCGTAAATAGTCCCAATAACAGAGTACGCGCAACTGTAACTAATAACTGATCAATAATT
      F  L  F  Q  Y  Y  .  S  I  Y  Q  G  Y  C  L  M  R  V  D  I  D  Y  .  L  V  L  N
   L  P  F  S  I  L  L  K  H  L  S  G  L  Y  S  H  A  R  .  H  .  L  L  T  S  Y  .
      S  F  F  N  I  I  L  E  A  F  I  R  Q  V  I  V  S  C  A  L  T  L  I  I  D  .  L  L
   K  R  K  .  Y  .  Q  L  M  .  .  P  .  Q  R  M  R  T  S  M  S  .  Q  S  T  L  L
      E  K  K  L  I  I  N  S  A  N  I  L  T  I  T  E  H  A  N  V  N  I  S  .  N  N  I
   G  K  E  I  N  N  F  C  K  D  P  N  N  D  .  A  R  Q  C  Q  N  N  V  L  .  .

                                                                      Hae III
                                                                       Bgl I
TAGTAATCAATTACGGGGTCATTAGTTCATAGCCCATATATGGAGTTCCGCGTTACATAACTTACGGTAAATGGCCCGCC
                                                                                  3520
ATCATTAGTTAATGCCCCAGTAATCAAGTATCGGGTATATACCTCAAGGCGCAATGTATTGAATGCCATTTACCGGGCGG
         S  N  Q  L  R  G  H  .  F  I  A  H  I  W  S  S  A  L  H  N  L  R  .  M  A  R
   I  V  I  N  Y  G  V  I  S  S  .  P  I  Y  G  V  P  R  Y  I  T  Y  G  K  W  P  A
      .  .  S  I  T  G  S  L  V  H  S  P  Y  M  E  F  R  V  T  .  L  T  V  N  G  P  P
      L  L  .  N  R  P  .  .  N  M  A  W  I  H  L  E  A  N  C  L  K  R  Y  I  A  R  R
   T  I  L  .  P  T  M  L  E  Y  G  M  Y  P  T  G  R  .  M  V  .  P  L  H  G  C
      Y  Y  D  I  V  P  D  N  T  .  L  G  Y  I  S  N  R  T  V  Y  S  V  T  F  P  G  G
```

```
                                    Aat II
ACTCACGGGGATTTCCAAGTCTCCACCCCATTGACGTCAATGGGAGTTTGTTTTGGCACCAAAATCAACGGGACTTTCCA  3920
TGAGTGCCCCTAAAGGTTCAGAGCTGGGGTAACTGCAGTTACCCTCAAACAAAACCGTGGTTTTAGTTGCCCTGAAAGGT
  T  H  G  D  F  Q  V  S  T  P  L  T  S  M  G  V  C  F  G  T  K  I  N  G  T  P  Q
   L  T  G  I  S  K  S  P  P  H  ·  R  Q  W  E  F  V  L  A  P  K  S  T  G  L  S
    D  S  R  G  F  P  S  L  H  P  I  D  V  N  G  S  L  F  W  H  Q  N  Q  R  D  F  P
  V  ·  P  S  K  W  T  E  V  G  N  V  D  I  P  T  Q  K  P  V  L  I  L  P  V  K  W
   S  V  P  I  E  L  D  G  G  W  Q  R  ·  H  S  N  T  K  A  G  F  D  V  P  S  E  L
    E  R  P  N  G  L  R  W  G  M  S  T  L  P  L  K  N  Q  C  W  F  ·  R  S  K  G

                                         Rsa I                             Sac I
AAATGTCGTAACAACTCCGCCCCATTGACGCAAATGGGCGGTAGGCGTGTACGGTGGGAGGTCTATATAAGCAGAGCTCT 4000
TTTACAGCATTGTTGAGGCGGGGTAACTGCGTTTACCCGCCATCCGCACATGCCACCCTCCAGATATATTCGTCTCGAGA
  N  V  V  T  T  P  P  H  ·  R  K  W  A  V  G  V  Y  G  G  R  S  I  ·  A  E  L
   K  M  S  ·  Q  L  R  P  I  D  A  N  G  R  ·  A  C  T  V  G  G  L  Y  K  Q  S  S
    F  T  T  V  V  G  G  W  Q  R  L  H  A  T  P  T  Y  P  P  L  D  I  Y  A  S  S  E
   F  I  D  Y  C  S  R  G  M  S  A  F  P  R  Y  A  H  V  T  P  P  R  Y  L  C  L  E
    F  H  R  L  L  E  A  G  N  V  C  I  P  P  L  R  T  R  H  S  T  ·  I  L  L  A  R

                           Age I
CTGGCTAACTAGAGAACCCACTGCTTAACTGGCTTATCGAAATTAATACGACTCACTATAGGGAGACCC
GACCGATTGATCTCTTGGGTGACGAATTGACCGAATAGCTTTAATTATGCTGAGTGATATCCCTCTGGG         4069
  S  G  ·  L  E  N  P  L  L  N  W  L  I  E  I  N  T  T  H  Y  R  E  T
   L  A  N  ·  R  T  H  C  L  T  G  L  S  K  L  I  R  L  T  I  G  R  P
    W  L  T  R  E  P  T  A  ·  L  A  Y  R  N  ·  Y  D  S  L  ·  G  D  P
  P  ·  S  S  F  G  S  S  L  Q  S  I  S  I  L  V  V  ·  ·  L  S  V  W
   R  A  L  ·  L  V  V  Q  K  V  P  K  D  F  N  I  R  S  V  I  P  L  G
    Q  S  Y  L  S  G  V  A  ·  S  A  ·  R  F  ·  Y  S  E  S  Y  P  S  G
```

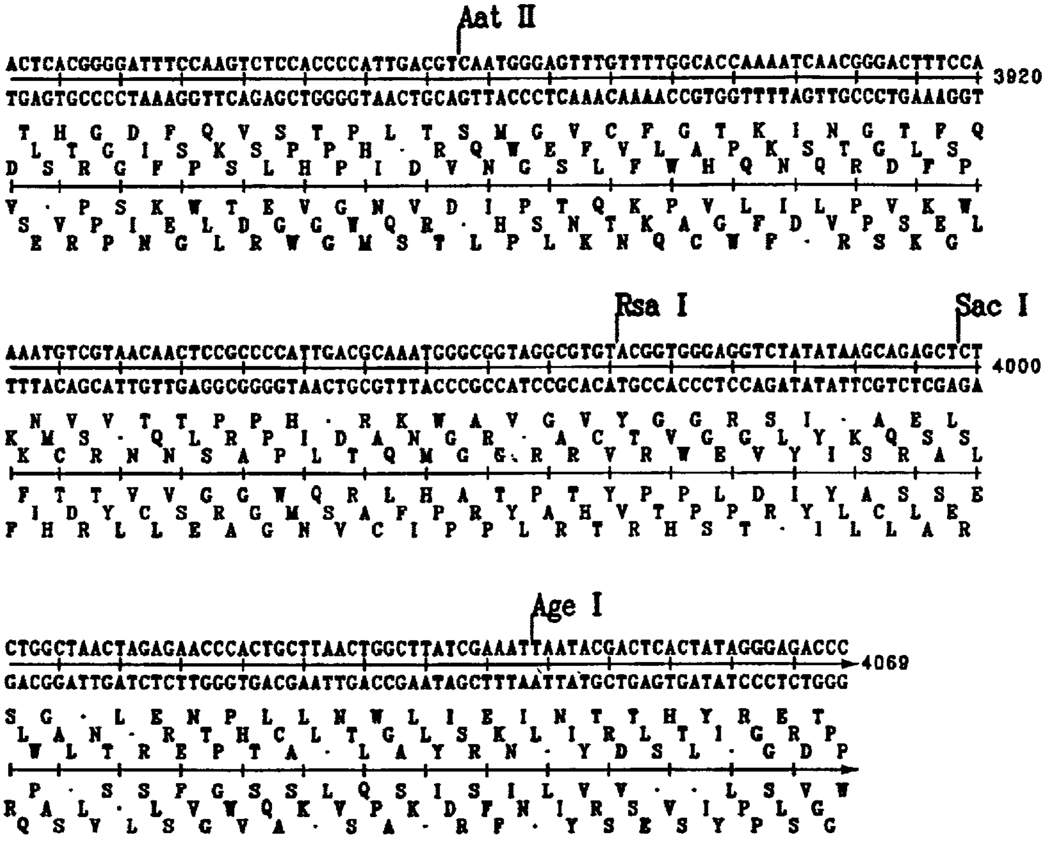

*FIG. 18L*

```
SEQUENCE LISTING

<160> NUMBER OF SEQ ID NOS: 60

<210> SEQ ID NO 1
<211> LENGTH: 26
<212> TYPE: DNA
<213> ORGANISM: Artificial Sequence
<220> FEATURE:
<223> OTHER INFORMATION: Oligonucleotide

<400> SEQUENCE: 1

ggaggatcca tggcctggtt ctcagc                                        26


<210> SEQ ID NO 2
<211> LENGTH: 29
<212> TYPE: DNA
<213> ORGANISM: Artificial Sequence
<220> FEATURE:
<223> OTHER INFORMATION: Oligonucleotide

<400> SEQUENCE: 2

cacaagctta grccrtccmg rcarttcca                                     29


<210> SEQ ID NO 3
<211> LENGTH: 30
<212> TYPE: DNA
<213> ORGANISM: Artificial Sequence
<220> FEATURE:
<223> OTHER INFORMATION: Oligonucleotide

<400> SEQUENCE: 3

ggagaagctt ctggcggcga tgaacgctag                                    30


<210> SEQ ID NO 4
<211> LENGTH: 28
<212> TYPE: DNA
<213> ORGANISM: Artificial Sequence
<220> FEATURE:
<223> OTHER INFORMATION: Oligonucleotide

<400> SEQUENCE: 4

acaggatcca ggtggctgct agcaagag                                      28


<210> SEQ ID NO 5
<211> LENGTH: 30
<212> TYPE: DNA
<213> ORGANISM: Artificial Sequence
<220> FEATURE:
<223> OTHER INFORMATION: Oligonucleotide

<400> SEQUENCE: 5
```

-continued cttaagctta aaatgaacga agacccgaag 30

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide

<400> SEQUENCE: 6
ggaggatccc cagagcatca ctagcat 27

<210> SEQ ID NO 7
<211> LENGTH: 530
<212> TYPE: DNA
<213> ORGANISM: Rattus rattus

<400> SEQUENCE: 7
ggaggatcca tggcctggtt ctcagccggc tcaggcagtg tgaatgtgag catagaccca 60
gcagaggaac ctacaggccc agctacactg ctgccctctc ccagggcctg ggatgtggtg 120
ctgtgcatct caggcaccct ggtgtcctgc gagaatgctc tggtgatggc catcattgtg 180
ggcacgcctg ccttccgcgc ccccatgttc ctgctggtgg gcagcttggc cgtagcagac 240
ctgctggcag gcctgggcct ggtcctgcac ttcgctgctg acttctgtat tggctcacca 300
gagatgagct tggtgctggt tggcgtgcta gcaacggcct ttactgccag catcggcagc 360
ctgctggcca tcaccgttga ccgctacctt tccctgtaca acgccctcac ctactactca 420
gagacaacag taactcgaac ctacgtgatg ctggccttgg tgtgggtggg tgccctgggc 480
ctggggctgg ttcccgtgct ggcctggaac tgccgggacg gtctaagctt 530

<210> SEQ ID NO 8
<211> LENGTH: 601
<212> TYPE: DNA
<213> ORGANISM: Rattus rattus

<400> SEQUENCE: 8
aagcttctgg cggcgatgaa cgctagcgcc gccgcgctca acgagtccca ggtggtggca 60
gtagcggccg agggagcggc agctgcggct acagcagcag ggacaccgga caccagcgaa 120
tggggacctc cggcagcatc cgcggcgctg ggaggcggcg gaggacctaa cgggtcactg 180
gagctgtctt cgcagctgcc cgcaggaccc tcaggacttc tgctttcggc agtgaatccc 240
tgggatgtgc tgctgtgcgt gtcggggact gtgatcgcag gcgaaaatgc gctggtggtg 300
gcgctcatcg catccactcc cgcgctgcgc acgcccatgt ttgtgctcgt gggtagtctg 360
gccactgctg acctgctggc gggctgtggc ctcatcctac acttcgtgtt ccagtacgtg 420
gtgccctcgg agactgtgag cctgctcatg gtgggcttcc tggtggcgtc cttcgccgcc 480
tcagtcagca gcctgctcgc tatcacagtg gaccgttacc tgtcccttta caacgcgctc 540
acctactact cgcgccggac cctgttgggc gtgcacctct tgctagcagc cacctggatc 600
c 601

<210> SEQ ID NO 9
<211> LENGTH: 510
<212> TYPE: DNA
<213> ORGANISM: Rattus rattus

<400> SEQUENCE: 9

-continued

```
aagcttaaaa tgaacgaaga cccgaaggtc aatttaagcg ggctgcctcg ggactgtata     60

gaagctggta ctccggagaa catctcagcc gctgtcccct cccagggctc tgttgtggag    120

tcagaacccg agctcgttgt caacccctgg gacattgtct tgtgcagctc aggaaccctc    180

atctgctgtg aaaatgccgt cgtggtcctt atcatcttcc acagccccag cctgcgagca    240

cccatgttcc tgctgatagg cagcctggct cttgcagacc tgctggctgg tctgggactc    300

atcatcaatt ttgtttttgc ctacctgctt cagtcagaag ccaccaagct ggtcacaatt    360

ggactcattg tcgcctcttt ctctgcctct gtctgcagtt tgctggctat cactgtggac    420

cgctacctct cgctgtatta cgccctgacg taccactccg agaggaccgt cacctttacc    480

tatgtcatgc tagtgatgct ctggggatcc                                     510


<210> SEQ ID NO 10
<211> LENGTH: 24
<212> TYPE: DNA
<213> ORGANISM: Artificial Sequence
<220> FEATURE:
<223> OTHER INFORMATION: Oligonucleotide

<400> SEQUENCE: 10

cttaagcttg tggcatttgg tact                                            24


<210> SEQ ID NO 11
<211> LENGTH: 28
<212> TYPE: DNA
<213> ORGANISM: Artificial Sequence
<220> FEATURE:
<223> OTHER INFORMATION: Oligonucleotide

<400> SEQUENCE: 11

tctggatcct tggccaggca gtggaagt                                        28


<210> SEQ ID NO 12
<211> LENGTH: 30
<212> TYPE: DNA
<213> ORGANISM: Artificial Sequence
<220> FEATURE:
<223> OTHER INFORMATION: PCR Primer

<400> SEQUENCE: 12

gagaattcac tcctgagctc aagatgaact                                      30


<210> SEQ ID NO 13
<211> LENGTH: 30
<212> TYPE: DNA
<213> ORGANISM: Artificial Sequence
<220> FEATURE:
<223> OTHER INFORMATION: PCR Primer

<400> SEQUENCE: 13

cgggatcccc gtaactgagc cacttcagat                                      30


<210> SEQ ID NO 14
<211> LENGTH: 1050
<212> TYPE: DNA
<213> ORGANISM: Homo sapiens

<400> SEQUENCE: 14

atgaactcca ccttggatgg taatcagagc agccaccctt tttgcctctt ggcatttggc     60

tatttggaaa ctgtcaattt ttgccttttg gaagtattga ttattgtctt tctaactgta    120

ttgattattt ctggcaacat cattgtgatt tttgtatttc actgtgcacc tttgttgaac    180
```

-continued

```
catcacacta caagttattt tatccagact atggcatatg ctgacctttt tgttggggtg    240

agctgcgtgg tcccttcttt atcactcctc catcaccccc ttccagtaga ggagtccttg    300

acttgccaga tatttggttt tgtagtatca gttctgaaga gcgtctccat ggcttctctg    360

gcctgtatca gcattgatag atacattgcc attactaaac ctttaaccta taatactctg    420

gttacaccct ggagactacg cctgtgtatt ttcctgattt ggctatactc gaccctggtc    480

ttcctgcctt cctttttcca ctggggcaaa cctggatatc atggagatgt gtttcagtgg    540

tgtgcggagt cctggcacac cgactcctac ttcaccctgt tcatcgtgat gatgttatat    600

gccccagcag cccttattgt ctgcttcacc tatttcaaca tcttccgcat ctgccaacag    660

cacacaaagg atatcagcga aaggcaagcc cgcttcagca gccagagtgg ggagactggg    720

gaagtgcagg cctgtcctga taagcgctat gccatggtcc tgtttcgaat cactagtgta    780

ttttacatcc tctggttgcc atatatcatc tacttcttgt tggaaagctc cactggccac    840

agcaaccgct tcgcatcctt cttgaccacc tggcttgcta ttagtaacag tttctgcaac    900

tgtgtaattt atagtctctc caacagtgta ttccaaagag gactaaagcg cctctcaggg    960

gctatgtgta cttcttgtgc aagtcagact acagccaacg acccttacac agttagaagc   1020

aaaggccctc ttaatggatg tcatatctga                                    1050


<210> SEQ ID NO 15
<211> LENGTH: 349
<212> TYPE: PRT
<213> ORGANISM: Homo sapiens

<400> SEQUENCE: 15

Met Asn Ser Thr Leu Asp Gly Asn Gln Ser Ser His Pro Phe Cys Leu
1               5                   10                  15

Leu Ala Phe Gly Tyr Leu Glu Thr Val Asn Phe Cys Leu Leu Glu Val
            20                  25                  30

Leu Ile Ile Val Phe Leu Thr Val Leu Ile Ile Ser Gly Asn Ile Ile
        35                  40                  45

Val Ile Phe Val Phe His Cys Ala Pro Leu Leu Asn His His Thr Thr
    50                  55                  60

Ser Tyr Phe Ile Gln Thr Met Ala Tyr Ala Asp Leu Phe Val Gly Val
65                  70                  75                  80

Ser Cys Val Val Pro Ser Leu Ser Leu Leu His His Pro Leu Pro Val
                85                  90                  95

Glu Glu Ser Leu Thr Cys Gln Ile Phe Gly Phe Val Val Ser Val Leu
            100                 105                 110

Lys Ser Val Ser Met Ala Ser Leu Ala Cys Ile Ser Ile Asp Arg Tyr
        115                 120                 125

Ile Ala Ile Thr Lys Pro Leu Thr Tyr Asn Thr Leu Val Thr Pro Trp
    130                 135                 140

Arg Leu Arg Leu Cys Ile Phe Leu Ile Trp Leu Tyr Ser Thr Leu Val
145                 150                 155                 160

Phe Leu Pro Ser Phe Phe His Trp Gly Lys Pro Gly Tyr His Gly Asp
                165                 170                 175

Val Phe Gln Trp Cys Ala Glu Ser Trp His Thr Asp Ser Tyr Phe Thr
            180                 185                 190

Leu Phe Ile Val Met Met Leu Tyr Ala Pro Ala Ala Leu Ile Val Cys
        195                 200                 205

Phe Thr Tyr Phe Asn Ile Phe Arg Ile Cys Gln Gln His Thr Lys Asp
```

-continued

```
    210                 215                 220

Ile Ser Glu Arg Gln Ala Arg Phe Ser Ser Gln Ser Gly Glu Thr Gly
225                 230                 235                 240

Glu Val Gln Ala Cys Pro Asp Lys Arg Tyr Ala Met Val Leu Phe Arg
                245                 250                 255

Ile Thr Ser Val Phe Tyr Ile Leu Trp Leu Pro Tyr Ile Ile Tyr Phe
            260                 265                 270

Leu Leu Glu Ser Ser Thr Gly His Ser Asn Arg Phe Ala Ser Phe Leu
        275                 280                 285

Thr Thr Trp Leu Ala Ile Ser Asn Ser Phe Cys Asn Cys Val Ile Tyr
    290                 295                 300

Ser Leu Ser Asn Ser Val Phe Gln Arg Gly Leu Lys Arg Leu Ser Gly
305                 310                 315                 320

Ala Met Cys Thr Ser Cys Ala Ser Gln Thr Thr Ala Asn Asp Pro Tyr
                325                 330                 335

Thr Val Arg Ser Lys Gly Pro Leu Asn Gly Cys His Ile
            340                 345


<210> SEQ ID NO 16
<211> LENGTH: 30
<212> TYPE: DNA
<213> ORGANISM: Artificial Sequence
<220> FEATURE:
<223> OTHER INFORMATION: PCR Primer

<400> SEQUENCE: 16

aggaagcttt aaatttccaa gccatgaatg                                    30


<210> SEQ ID NO 17
<211> LENGTH: 31
<212> TYPE: DNA
<213> ORGANISM: Artificial Sequence
<220> FEATURE:
<223> OTHER INFORMATION: PCR Primer

<400> SEQUENCE: 17

accgaattca gattacattt gatttactat g                                  31


<210> SEQ ID NO 18
<211> LENGTH: 1086
<212> TYPE: DNA
<213> ORGANISM: Homo sapiens

<400> SEQUENCE: 18

atgaatgaat ccaggtggac tgaatggagg atcctgaaca tgagcagtgg cattgtgaat     60

gtgtccgagc gtcactcctg cccacttgga tttggccact acagtgtggt ggatgtctgc    120

atcttcgaga cagtggttat tgtgttgctg acatttctga tcattgctgg gaatctaaca    180

gttatctttg tctttcattg tgctccactg ttacatcatt atactaccag ctatttcatt    240

cagacgatgg catatgctga tcttttcgtt ggagttagct gcttggttcc tactctgtca    300

cttctccact actccacagg tgtccacgag tcattgactt gccaggtttt tggatatatc    360

atctcagttc taaaaagtgt ttctatggca tgtcttgctt gcatcagtgt ggatcgttat    420

cttgcaataa ccaagcctct ttcctacaat caactggtca ccccttgtcg cttgagaatt    480

tgcattattt tgatctggat ctactcctgc ctaattttct tgccttcctt ttttggctgg    540

gggaaacctg gttaccatgg tgacattttt gaatggtgtg ccacgtcttg gctcaccagt    600

gcctatttta ctggctttat tgtttgttta ctttatgctc ctgctgcctt tgttgtctgc    660
```

-continued

```
ttcacttact tccacatttt caaaatttgc cgtcagcaca ccaaagagat aaatgaccga    720

agagcccgat tccctagtca tgaggtagat tcttccagag agactggaca cagccctgac    780

cgtcgctacg ccatggtttt gtttaggata accagtgtat tttatatgct gtggctcccc    840

tatataattt actttcttct agaaagctcc cgggtcttgg acaatccaac tctgtccttc    900

ttaacaacct ggcttgcaat aagtaatagt ttttgtaact gtgtaatata cagcctctcc    960

aacagcgttt tccggctagg cctccgaaga ctgtctgaga caatgtgcac atcctgtatg   1020

tgtgtgaagg atcaggaagc acaagaaccc aaacctagga aacgggctaa ttcttgctcc   1080

atttga                                                              1086


<210> SEQ ID NO 19
<211> LENGTH: 361
<212> TYPE: PRT
<213> ORGANISM: Homo sapiens

<400> SEQUENCE: 19

Met Asn Glu Ser Arg Trp Thr Glu Trp Arg Ile Leu Asn Met Ser Ser
1               5                   10                  15

Gly Ile Val Asn Val Ser Glu Arg His Ser Cys Pro Leu Gly Phe Gly
            20                  25                  30

His Tyr Ser Val Val Asp Val Cys Ile Phe Glu Thr Val Val Ile Val
        35                  40                  45

Leu Leu Thr Phe Leu Ile Ile Ala Gly Asn Leu Thr Val Ile Phe Val
    50                  55                  60

Phe His Cys Ala Pro Leu Leu His His Tyr Thr Thr Ser Tyr Phe Ile
65                  70                  75                  80

Gln Thr Met Ala Tyr Ala Asp Leu Phe Val Gly Val Ser Cys Leu Val
                85                  90                  95

Pro Thr Leu Ser Leu Leu His Tyr Ser Thr Gly Val His Glu Ser Leu
            100                 105                 110

Thr Cys Gln Val Phe Gly Tyr Ile Ile Ser Val Leu Lys Ser Val Ser
        115                 120                 125

Met Ala Cys Leu Ala Cys Ile Ser Val Asp Arg Tyr Leu Ala Ile Thr
    130                 135                 140

Lys Pro Leu Ser Tyr Asn Gln Leu Val Thr Pro Cys Arg Leu Arg Ile
145                 150                 155                 160

Cys Ile Ile Leu Ile Trp Ile Tyr Ser Cys Leu Ile Phe Leu Pro Ser
                165                 170                 175

Phe Phe Gly Trp Gly Lys Pro Gly Tyr His Gly Asp Ile Phe Glu Trp
            180                 185                 190

Cys Ala Thr Ser Trp Leu Thr Ser Ala Tyr Phe Thr Gly Phe Ile Val
        195                 200                 205

Cys Leu Leu Tyr Ala Pro Ala Ala Phe Val Val Cys Phe Thr Tyr Phe
    210                 215                 220

His Ile Phe Lys Ile Cys Arg Gln His Thr Lys Glu Ile Asn Asp Arg
225                 230                 235                 240

Arg Ala Arg Phe Pro Ser His Glu Val Asp Ser Ser Arg Glu Thr Gly
                245                 250                 255

His Ser Pro Asp Arg Arg Tyr Ala Met Val Leu Phe Arg Ile Thr Ser
            260                 265                 270

Val Phe Tyr Met Leu Trp Leu Pro Tyr Ile Ile Tyr Phe Leu Leu Glu
        275                 280                 285
```

-continued

```
Ser Ser Arg Val Leu Asp Asn Pro Thr Leu Ser Phe Leu Thr Thr Trp
    290                 295                 300

Leu Ala Ile Ser Asn Ser Phe Cys Asn Cys Val Ile Tyr Ser Leu Ser
305                 310                 315                 320

Asn Ser Val Phe Arg Leu Gly Leu Arg Arg Leu Ser Glu Thr Met Cys
                325                 330                 335

Thr Ser Cys Met Cys Val Lys Asp Gln Glu Ala Gln Glu Pro Lys Pro
            340                 345                 350

Arg Lys Arg Ala Asn Ser Cys Ser Ile
        355                 360


<210> SEQ ID NO 20
<211> LENGTH: 32
<212> TYPE: DNA
<213> ORGANISM: Artificial Sequence
<220> FEATURE:
<223> OTHER INFORMATION: PCR Primer

<400> SEQUENCE: 20

agcgaattct gcccacccca cgccgaggtg ct                                    32


<210> SEQ ID NO 21
<211> LENGTH: 30
<212> TYPE: DNA
<213> ORGANISM: Artificial Sequence
<220> FEATURE:
<223> OTHER INFORMATION: PCR Primer

<400> SEQUENCE: 21

tgcggatccg ccagctcttg agcctgcaca                                       30


<210> SEQ ID NO 22
<211> LENGTH: 1382
<212> TYPE: DNA
<213> ORGANISM: Homo sapiens

<400> SEQUENCE: 22

ggccttatct ttccagtcgt ccagcatgct ctgcccaccc cacgccgagg tgcactgacc      60

atgagcctca actcctccct cagctgcagg aaggagctga gtaatctcac tgaggaggag     120

ggtggcgaag gggcgtcat catcacccag ttcatcgcca tcattgtcat caccattttt      180

gtctgcctgg gaaacctggt catcgtggtc accttgtaca agaagtccta cctcctcacc     240

ctcagcaaca agttcgtctt cagcctgact ctgtccaact tcctgctgtc cgtgttggtg     300

ctgccttttg tggtgacgag ctccatccgc agggaatgga tctttggtgt agtgtggtgc     360

aacttctctg ccctcctcta cctgctgatc agctctgcca gcatgctaac cctcggggtc     420

attgccatcg accgctacta tgctgtcctg taccccatgg tgtaccccat gaagatcaca     480

gggaaccggg ctgtgatggc acttgtctac atctggcttc actcgctcat cggctgcctg     540

ccacccctgt ttggttggtc atccgtggag tttgacgagt tcaaatggat gtgtgtggct     600

gcttggcacc gggagcctgg ctacacggcc ttctggcaga tctggtgtgc cctcttcccc     660

tttctggtca tgctggtgtg ctatggcttc atcttccgcg tggccagggt caaggcacgc     720

aaggtgcact gtggcacagt cgtcatcgtg gaggaggatg ctcagaggac cgggaggaag     780

aactccagca cctccacctc ctcttcaggc agcaggagga atgcctttca gggtgtggtc     840

tactcggcca accagtgcaa agccctcatc accatcctgg tggtcctcgg tgccttcatg     900

gtcacctggg gcccctacat ggttgtcatc gcctctgagg ccctctgggg gaaaagctcc     960
```

-continued

```
gtctccccga gcctggagac ttgggccaca tggctgtcct ttgccagcgc tgtctgccac   1020

cccctgatct atggactctg gaacaagaca gttcgcaaag aactactggg catgtgcttt   1080

ggggaccggt attatcggga accatttgtg caacgacaga ggacttccag gctcttcagc   1140

atttccaaca ggatcacaga cctgggcctg tccccacacc tcactgcgct catggcaggt   1200

ggacagcccc tggggcacag cagcagcacg ggggacactg gcttcagctg ctcccaggac   1260

tcaggtaacc tgcgtgcttt ataagcctct cacctgtcgc gttttccctg tgttgcgttt   1320

cccccgtgtc gcgtttcccc tgtgcaggct caagagctgg cggaggggca tttcccacgg   1380

tg                                                                  1382


<210> SEQ ID NO 23
<211> LENGTH: 407
<212> TYPE: PRT
<213> ORGANISM: Homo sapiens

<400> SEQUENCE: 23

Met Ser Leu Asn Ser Ser Leu Ser Cys Arg Lys Glu Leu Ser Asn Leu
1               5                   10                  15

Thr Glu Glu Glu Gly Gly Glu Gly Gly Val Ile Ile Thr Gln Phe Ile
            20                  25                  30

Ala Ile Ile Val Ile Thr Ile Phe Val Cys Leu Gly Asn Leu Val Ile
        35                  40                  45

Val Val Thr Leu Tyr Lys Lys Ser Tyr Leu Leu Thr Leu Ser Asn Lys
    50                  55                  60

Phe Val Phe Ser Leu Thr Leu Ser Asn Phe Leu Leu Ser Val Leu Val
65                  70                  75                  80

Leu Pro Phe Val Val Thr Ser Ser Ile Arg Arg Glu Trp Ile Phe Gly
                85                  90                  95

Val Val Trp Cys Asn Phe Ser Ala Leu Leu Tyr Leu Leu Ile Ser Ser
            100                 105                 110

Ala Ser Met Leu Thr Leu Gly Val Ile Ala Ile Asp Arg Tyr Tyr Ala
        115                 120                 125

Val Leu Tyr Pro Met Val Tyr Pro Met Lys Ile Thr Gly Asn Arg Ala
    130                 135                 140

Val Met Ala Leu Val Tyr Ile Trp Leu His Ser Leu Ile Gly Cys Leu
145                 150                 155                 160

Pro Pro Leu Phe Gly Trp Ser Ser Val Glu Phe Asp Glu Phe Lys Trp
                165                 170                 175

Met Cys Val Ala Ala Trp His Arg Glu Pro Gly Tyr Thr Ala Phe Trp
            180                 185                 190

Gln Ile Trp Cys Ala Leu Phe Pro Phe Leu Val Met Leu Val Cys Tyr
        195                 200                 205

Gly Phe Ile Phe Arg Val Ala Arg Val Lys Ala Arg Lys Val His Cys
    210                 215                 220

Gly Thr Val Val Ile Val Glu Glu Asp Ala Gln Arg Thr Gly Arg Lys
225                 230                 235                 240

Asn Ser Ser Thr Ser Thr Ser Ser Ser Gly Ser Arg Arg Asn Ala Phe
                245                 250                 255

Gln Gly Val Val Tyr Ser Ala Asn Gln Cys Lys Ala Leu Ile Thr Ile
            260                 265                 270

Leu Val Val Leu Gly Ala Phe Met Val Thr Trp Gly Pro Tyr Met Val
        275                 280                 285

Val Ile Ala Ser Glu Ala Leu Trp Gly Lys Ser Ser Val Ser Pro Ser
```

-continued

```
    290                 295                 300

Leu Glu Thr Trp Ala Thr Trp Leu Ser Phe Ala Ser Ala Val Cys His
305                 310                 315                 320

Pro Leu Ile Tyr Gly Leu Trp Asn Lys Thr Val Arg Lys Glu Leu Leu
                325                 330                 335

Gly Met Cys Phe Gly Asp Arg Tyr Tyr Arg Glu Pro Phe Val Gln Arg
            340                 345                 350

Gln Arg Thr Ser Arg Leu Phe Ser Ile Ser Asn Arg Ile Thr Asp Leu
        355                 360                 365

Gly Leu Ser Pro His Leu Thr Ala Leu Met Ala Gly Gly Gln Pro Leu
    370                 375                 380

Gly His Ser Ser Ser Thr Gly Asp Thr Gly Phe Ser Cys Ser Gln Asp
385                 390                 395                 400

Ser Gly Asn Leu Arg Ala Leu
                405


<210> SEQ ID NO 24
<211> LENGTH: 30
<212> TYPE: DNA
<213> ORGANISM: Artificial Sequence
<220> FEATURE:
<223> OTHER INFORMATION: PCR Primer

<400> SEQUENCE: 24

ggaagcttca ggcccaaaga tggggaacat                                     30


<210> SEQ ID NO 25
<211> LENGTH: 30
<212> TYPE: DNA
<213> ORGANISM: Artificial Sequence
<220> FEATURE:
<223> OTHER INFORMATION: PCR Primer

<400> SEQUENCE: 25

gtggatccac ccgcggagga cccaggctag                                     30


<210> SEQ ID NO 26
<211> LENGTH: 1697
<212> TYPE: DNA
<213> ORGANISM: Homo sapiens

<400> SEQUENCE: 26

actcccaaag tgctgggctt acaggtgtaa gccatcatgt ccagccgttc agatattcta     60

gttgaattgg agttggtggg ctagtacacc ttctaaatta aatgagtaaa ggatttagaa    120

tggtgcctga cacacagtag gtgctacatt catgttagct actattataa acctttcctg    180

cctctgactt tcagggtctt gcccaccacc agcgatgccc agcccttggt agagcttgaa    240

ccaccttcta taaacaggat ggcggtggag agacaggccc agtccctgag cccatgagga    300

gtgtggcccc ttcaggccca aagatgggga acatcactgc agacaactcc tcgatgagct    360

gtaccatcga ccataccatc caccagacgc tggccccggt ggtctatgtt accgtgctgg    420

tggtgggctt cccggccaac tgcctgtccc tctacttcgg ctacctgcag atcaaggccc    480

ggaacgagct gggcgtgtac ctgtgcaacc tgacggtggc cgacctcttc tacatctgct    540

cgctgccctt ctggctgcag tacgtgctgc agcacgacaa ctggtctcac ggcgacctgt    600

cctgccaggt gtgcggcatc ctcctgtacg agaacatcta catcagcgtg ggcttcctct    660

gctgcatctc cgtggaccgc tacctggctg tggcccatcc cttccgcttc caccagttcc    720
```

-continued

```
ggaccctgaa ggcggccgtc ggcgtcagcg tggtcatctg ggccaaggag ctgctgacca    780

gcatctactt cctgatgcac gaggaggtca tcgaggacga gaaccagcac cgcgtgtgct    840

ttgagcacta ccccatccag gcatggcagc gcgccatcaa ctactaccgc ttcctggtgg    900

gcttcctctt ccccatctgc ctgctgctgg cgtcctacca gggcatcctg cgcgccgtgc    960

gccggagcca cggcacccag aagagccgca aggaccagat ccagcggctg gtgctcagca   1020

ccgtggtcat cttcctggcc tgcttcctgc cctaccacgt gttgctgctg gtgcgcagcg   1080

tctgggaggc cagctgcgac ttcgccaagg gcgttttcaa cgcctaccac ttctccctcc   1140

tgctcaccag cttcaactgc gtcgccgacc ccgtgctcta ctgcttcgtc agcgagacca   1200

cccaccggga cctggcccgc ctccgcgggg cctgcctggc cttcctcacc tgctccagga   1260

ccggccgggc cagggaggcc tacccgctgg gtgcccccga ggcctccggg aaaagcgggg   1320

cccagggtga ggagcccgag ctgttgacca agctccaccc ggccttccag accccctaact  1380

cgccagggtc gggcgggttc cccacgggca ggttggccta gcctgggtcc tccgcgggtg   1440

gctccacgtg aggcctgagc cttcagccca cgggcctcag ggcctgccgc ctcctgcttc   1500

cctcgctgcg gaggcaggga agcccctgta actccggaag cctgctctcg cttgctgagc   1560

ccgctgggac cgccgagggt gggaataagc cccggttggc tcgtgggaat aagccgtgtc   1620

ctctgccgcg gctgcgatgt ggccacgctg ggctgctggg tcgggggaaa acagtgaact   1680

gcgtcccctg gcctgct                                                  1697
```

<210> SEQ ID NO 27
<211> LENGTH: 365
<212> TYPE: PRT
<213> ORGANISM: Homo sapiens

<400> SEQUENCE: 27

```
Met Gly Asn Ile Thr Ala Asp Asn Ser Ser Met Ser Cys Thr Ile Asp
1               5                   10                  15

His Thr Ile His Gln Thr Leu Ala Pro Val Val Tyr Val Thr Val Leu
            20                  25                  30

Val Val Gly Phe Pro Ala Asn Cys Leu Ser Leu Tyr Phe Gly Tyr Leu
        35                  40                  45

Gln Ile Lys Ala Arg Asn Glu Leu Gly Val Tyr Leu Cys Asn Leu Thr
    50                  55                  60

Val Ala Asp Leu Phe Tyr Ile Cys Ser Leu Pro Phe Trp Leu Gln Tyr
65                  70                  75                  80

Val Leu Gln His Asp Asn Trp Ser His Gly Asp Leu Ser Cys Gln Val
                85                  90                  95

Cys Gly Ile Leu Leu Tyr Glu Asn Ile Tyr Ile Ser Val Gly Phe Leu
            100                 105                 110

Cys Cys Ile Ser Val Asp Arg Tyr Leu Ala Val Ala His Pro Phe Arg
        115                 120                 125

Phe His Gln Phe Arg Thr Leu Lys Ala Ala Val Gly Val Ser Val Val
    130                 135                 140

Ile Trp Ala Lys Glu Leu Leu Thr Ser Ile Tyr Phe Leu Met His Glu
145                 150                 155                 160

Glu Val Ile Glu Asp Glu Asn Gln His Arg Val Cys Phe Glu His Tyr
                165                 170                 175

Pro Ile Gln Ala Trp Gln Arg Ala Ile Asn Tyr Tyr Arg Phe Leu Val
            180                 185                 190

Gly Phe Leu Phe Pro Ile Cys Leu Leu Leu Ala Ser Tyr Gln Gly Ile
```

-continued

```
        195                 200                 205

Leu Arg Ala Val Arg Arg Ser His Gly Thr Gln Lys Ser Arg Lys Asp
    210                 215                 220

Gln Ile Gln Arg Leu Val Leu Ser Thr Val Val Ile Phe Leu Ala Cys
225                 230                 235                 240

Phe Leu Pro Tyr His Val Leu Leu Leu Val Arg Ser Val Trp Glu Ala
                245                 250                 255

Ser Cys Asp Phe Ala Lys Gly Val Phe Asn Ala Tyr His Phe Ser Leu
            260                 265                 270

Leu Leu Thr Ser Phe Asn Cys Val Ala Asp Pro Val Leu Tyr Cys Phe
        275                 280                 285

Val Ser Glu Thr Thr His Arg Asp Leu Ala Arg Leu Arg Gly Ala Cys
    290                 295                 300

Leu Ala Phe Leu Thr Cys Ser Arg Thr Gly Arg Ala Arg Glu Ala Tyr
305                 310                 315                 320

Pro Leu Gly Ala Pro Glu Ala Ser Gly Lys Ser Gly Ala Gln Gly Glu
                325                 330                 335

Glu Pro Glu Leu Leu Thr Lys Leu His Pro Ala Phe Gln Thr Pro Asn
            340                 345                 350

Ser Pro Gly Ser Gly Gly Phe Pro Thr Gly Arg Leu Ala
        355                 360                 365


<210> SEQ ID NO 28
<211> LENGTH: 20
<212> TYPE: DNA
<213> ORGANISM: Artificial Sequence
<220> FEATURE:
<223> OTHER INFORMATION: PCR Primer

<400> SEQUENCE: 28

ctggtcctgc actttgctgc                                                   20


<210> SEQ ID NO 29
<211> LENGTH: 23
<212> TYPE: DNA
<213> ORGANISM: Artificial Sequence
<220> FEATURE:
<223> OTHER INFORMATION: PCR Primer

<400> SEQUENCE: 29

agcatcacat aggtccgtgt cac                                               23


<210> SEQ ID NO 30
<211> LENGTH: 24
<212> TYPE: DNA
<213> ORGANISM: Artificial Sequence
<220> FEATURE:
<223> OTHER INFORMATION: PCR Primer

<400> SEQUENCE: 30

accagaaagg gtgtgggtac actg                                              24


<210> SEQ ID NO 31
<211> LENGTH: 20
<212> TYPE: DNA
<213> ORGANISM: Artificial Sequence
<220> FEATURE:
<223> OTHER INFORMATION: PCR Primer

<400> SEQUENCE: 31

ggaacgaaag ggcactttgg                                                   20
```

-continued

<210> SEQ ID NO 32
<211> LENGTH: 20
<212> TYPE: DNA
<213> ORGANISM: Artificial Sequence
<220> FEATURE:
<223> OTHER INFORMATION: PCR Primer

<400> SEQUENCE: 32
gctgcctcgg gattatttag 20

<210> SEQ ID NO 33
<211> LENGTH: 23
<212> TYPE: DNA
<213> ORGANISM: Artificial Sequence
<220> FEATURE:
<223> OTHER INFORMATION: PCR Primer

<400> SEQUENCE: 33
gcctattagc aggaacatgg gtg 23

<210> SEQ ID NO 34
<211> LENGTH: 18
<212> TYPE: DNA
<213> ORGANISM: Artificial Sequence
<220> FEATURE:
<223> OTHER INFORMATION: Antisense Sequence

<400> SEQUENCE: 34
gctagcgttc atcgccgc 18

<210> SEQ ID NO 35
<211> LENGTH: 18
<212> TYPE: DNA
<213> ORGANISM: Artificial Sequence
<220> FEATURE:
<223> OTHER INFORMATION: Missense Sequence

<400> SEQUENCE: 35
ctggactgta tcgccccg 18

<210> SEQ ID NO 36
<211> LENGTH: 32
<212> TYPE: DNA
<213> ORGANISM: Artificial Sequence
<220> FEATURE:
<223> OTHER INFORMATION: Sense Sequence

<400> SEQUENCE: 36
gatctctaga atgatgtggg gtgcaggcag cc 32

<210> SEQ ID NO 37
<211> LENGTH: 35
<212> TYPE: DNA
<213> ORGANISM: Artificial Sequence
<220> FEATURE:
<223> OTHER INFORMATION: Antisense Sequence

<400> SEQUENCE: 37
ctagggtacc cggacatcac tgggggagcg ggatc 35

<210> SEQ ID NO 38
<211> LENGTH: 31
<212> TYPE: DNA
<213> ORGANISM: Artificial Sequence
<220> FEATURE:

-continued

<223> OTHER INFORMATION: Sense Sequence

<400> SEQUENCE: 38
gatctctaga atgcagggtg caaatccggc c 31

<210> SEQ ID NO 39
<211> LENGTH: 35
<212> TYPE: DNA
<213> ORGANISM: Artificial Sequence
<220> FEATURE:
<223> OTHER INFORMATION: Antisense Sequence

<400> SEQUENCE: 39
ctagggtacc cggacctcgc tgggagacct ggaac 35

<210> SEQ ID NO 40
<211> LENGTH: 22
<212> TYPE: DNA
<213> ORGANISM: Artificial Sequence
<220> FEATURE:
<223> OTHER INFORMATION: PCR Primer

<400> SEQUENCE: 40
atgtggaacg cgacgcccag cg 22

<210> SEQ ID NO 41
<211> LENGTH: 22
<212> TYPE: DNA
<213> ORGANISM: Artificial Sequence
<220> FEATURE:
<223> OTHER INFORMATION: PCR Primer

<400> SEQUENCE: 41
tcatgtatta atactagatt ct 22

<210> SEQ ID NO 42
<211> LENGTH: 38
<212> TYPE: DNA
<213> ORGANISM: Artificial Sequence
<220> FEATURE:
<223> OTHER INFORMATION: PCR Primer

<400> SEQUENCE: 42
taccatgtgg aacgcgacgc ccagcgaaga gccggggt 38

<210> SEQ ID NO 43
<211> LENGTH: 39
<212> TYPE: DNA
<213> ORGANISM: Artificial Sequence
<220> FEATURE:
<223> OTHER INFORMATION: PCR Primer

<400> SEQUENCE: 43
cggaattcat gtattaatac tagattctgt ccaggcccg 39

<210> SEQ ID NO 44
<211> LENGTH: 1101
<212> TYPE: DNA
<213> ORGANISM: Homo sapiens

<400> SEQUENCE: 44
atgtggaacg cgacgcccag cgaagagccg gggttcaacc tcacactggc cgacctggac 60
tgggatgctt cccccggcaa cgactcgctg ggcgacgagc tgctgcagct cttccccgcg 120
ccgctgctgg cgggcgtcac agccacctgc gtggcactct tcgtggtggg tatcgctggc 180

-continued

```
aacctgctca ccatgctggt ggtgtcgcgc ttccgcgagc tgcgcaccac caccaacctc    240

tacctgtcca gcatggcctt ctccgatctg ctcatcttcc tctgcatgcc cctggacctc    300

gttcgcctct ggcagtaccg gccctggaac ttcggcgacc tcctctgcaa actcttccaa    360

ttcgtcagtg agagctgcac ctacgccacg gtgctcacca tcacagcgct gagcgtcgag    420

cgctacttcg ccatctgctt cccactccgg gccaaggtgg tggtcaccaa ggggcgggtg    480

aagctggtca tcttcgtcat ctgggccgtg gccttctgca gcgccgggcc catcttcgtg    540

ctagtcgggg tggagcacga gaacggcacc gacccttggg acaccaacga gtgccgcccc    600

accgagtttg cggtgcgctc tggactgctc acggtcatgg tgtgggtgtc cagcatcttc    660

ttcttccttc ctgtcttctg tctcacggtc ctctacagtc tcatcggcag gaagctgtgg    720

cggaggaggc gcggcgatgc tgtcgtgggt gcctcgctca gggaccagaa ccacaagcaa    780

accgtgaaaa tgctggctgt agtggtgttt gccttcatcc tctgctggct cccctttccac    840

gtagggcgat atttattttc caaatccttt gagcctggct ccttggagat tgctcagatc    900

agccagtact gcaacctcgt gtcctttgtc ctcttctacc tcagtgctgc catcaacccc    960

attctgtaca acatcatgtc caagaagtac cgggtggcag tgttcagact tctgggattc   1020

gaacccttct cccagagaaa gctctccact ctgaaagatg aaagttctcg ggcctggaca   1080

gaatctagta ttaatacatg a                                            1101
```

<210> SEQ ID NO 45
<211> LENGTH: 366
<212> TYPE: PRT
<213> ORGANISM: Homo sapiens

<400> SEQUENCE: 45

```
Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205
```

-continued

Leu Leu Thr Val Met Val Trp Val Ser Ser Ile Phe Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Ala Val Val Val Phe Ala Phe
            260                 265                 270

Ile Leu Cys Trp Leu Pro Phe His Val Gly Arg Tyr Leu Phe Ser Lys
        275                 280                 285

Ser Phe Glu Pro Gly Ser Leu Glu Ile Ala Gln Ile Ser Gln Tyr Cys
    290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
                325                 330                 335

Leu Leu Gly Phe Glu Pro Phe Ser Gln Arg Lys Leu Ser Thr Leu Lys
            340                 345                 350

Asp Glu Ser Ser Arg Ala Trp Thr Glu Ser Ser Ile Asn Thr
        355                 360                 365

<210> SEQ ID NO 46
<211> LENGTH: 330
<212> TYPE: PRT
<213> ORGANISM: Homo sapiens

<400> SEQUENCE: 46

Met Met Trp Gly Ala Gly Ser Pro Leu Ala Trp Leu Ser Ala Gly Ser
1               5                   10                  15

Gly Asn Val Asn Val Ser Ser Val Gly Pro Ala Glu Gly Pro Thr Gly
            20                  25                  30

Pro Ala Ala Pro Leu Pro Ser Pro Lys Ala Trp Asp Val Val Leu Cys
        35                  40                  45

Ile Ser Gly Thr Leu Val Ser Cys Glu Asn Ala Leu Val Val Ala Ile
    50                  55                  60

Ile Val Gly Thr Pro Ala Phe Arg Ala Pro Met Phe Leu Leu Val Gly
65                  70                  75                  80

Ser Leu Ala Val Ala Asp Leu Leu Ala Gly Leu Gly Leu Val Leu His
                85                  90                  95

Phe Ala Ala Val Phe Cys Ile Gly Ser Ala Glu Met Ser Leu Val Leu
            100                 105                 110

Val Gly Val Leu Ala Met Ala Phe Thr Ala Ser Ile Gly Ser Leu Leu
        115                 120                 125

Ala Ile Thr Val Asp Arg Tyr Leu Ser Leu Tyr Asn Ala Leu Thr Tyr
    130                 135                 140

Tyr Ser Glu Thr Thr Val Thr Arg Thr Tyr Val Met Leu Ala Leu Val
145                 150                 155                 160

Trp Gly Gly Ala Leu Gly Leu Gly Leu Leu Pro Val Leu Ala Trp Asn
                165                 170                 175

Cys Leu Asp Gly Leu Thr Thr Cys Gly Val Val Tyr Pro Leu Ser Lys
            180                 185                 190

Asn His Leu Val Val Leu Ala Ile Ala Phe Phe Met Val Phe Gly Ile
        195                 200                 205

Met Leu Gln Leu Tyr Ala Gln Ile Cys Arg Ile Val Cys Arg His Ala

-continued

```
    210                 215                 220

Gln Gln Ile Ala Leu Gln Arg His Leu Leu Pro Ala Ser His Tyr Val
225                 230                 235                 240

Ala Thr Arg Lys Gly Ile Ala Thr Leu Ala Val Val Leu Gly Ala Phe
                245                 250                 255

Ala Ala Cys Trp Leu Pro Phe Thr Val Tyr Cys Leu Leu Gly Asp Ala
            260                 265                 270

His Ser Pro Pro Leu Tyr Thr Tyr Leu Thr Leu Leu Pro Ala Thr Tyr
        275                 280                 285

Asn Ser Met Ile Asn Pro Ile Ile Tyr Ala Phe Arg Asn Gln Asp Val
    290                 295                 300

Gln Lys Val Leu Trp Ala Val Cys Cys Cys Cys Ser Ser Ser Lys Leu
305                 310                 315                 320

Pro Phe Arg Ser Arg Ser Pro Ser Asp Val
                325                 330


<210> SEQ ID NO 47
<211> LENGTH: 362
<212> TYPE: PRT
<213> ORGANISM: Homo sapiens

<400> SEQUENCE: 47

Met Asn Ala Ser Ala Ala Ser Leu Asn Asp Ser Gln Val Val Val Val
1               5                   10                  15

Ala Ala Glu Gly Ala Ala Ala Ala Ala Thr Ala Ala Gly Gly Pro Asp
            20                  25                  30

Thr Gly Glu Trp Gly Pro Pro Ala Ala Ala Ala Leu Gly Ala Gly Gly
        35                  40                  45

Gly Ala Asn Gly Ser Leu Glu Leu Ser Ser Gln Leu Ser Ala Gly Pro
    50                  55                  60

Pro Gly Leu Leu Leu Pro Ala Val Asn Pro Trp Asp Val Leu Leu Cys
65                  70                  75                  80

Ser Val Gly Thr Val Ile Ala Gly Glu Asn Ala Leu Val Val Ala Leu
                85                  90                  95

Ile Ala Ser Thr Pro Ala Leu Arg Thr Pro Met Phe Val Leu Val Gly
            100                 105                 110

Ser Leu Ala Thr Ala Asp Leu Leu Ala Gly Cys Gly Leu Ile Leu His
        115                 120                 125

Phe Val Phe Gln Tyr Leu Val Pro Ser Glu Thr Val Ser Leu Leu Thr
    130                 135                 140

Val Gly Phe Leu Val Ala Ser Phe Ala Ala Ser Val Ser Ser Leu Leu
145                 150                 155                 160

Ala Ile Thr Val Asp Arg Tyr Leu Ser Leu Tyr Asn Ala Leu Thr Tyr
                165                 170                 175

Tyr Ser Arg Arg Thr Leu Leu Gly Val His Leu Leu Leu Ala Ala Thr
            180                 185                 190

Trp Thr Val Ser Leu Gly Leu Gly Leu Leu Pro Val Leu Gly Trp Asn
        195                 200                 205

Cys Leu Ala Glu Arg Ala Ala Cys Ser Val Val Arg Pro Leu Ala Arg
    210                 215                 220

Ser His Val Ala Leu Leu Ser Ala Ala Phe Phe Met Val Phe Gly Ile
225                 230                 235                 240

Met Leu His Leu Tyr Val Arg Ile Cys Gln Val Val Trp Arg His Ala
                245                 250                 255
```

-continued

His Gln Ile Ala Leu Gln Gln His Cys Leu Ala Pro Pro His Leu Ala
260 265 270

Ala Thr Arg Lys Gly Val Gly Thr Leu Ala Val Val Leu Gly Thr Phe
275 280 285

Gly Ala Ser Trp Leu Pro Phe Ala Ile Tyr Cys Val Val Gly Ser His
290 295 300

Glu Asp Pro Ala Val Tyr Thr Tyr Ala Thr Leu Leu Pro Ala Thr Tyr
305 310 315 320

Asn Ser Met Ile Asn Pro Ile Ile Tyr Ala Phe Arg Asn Gln Glu Ile
325 330 335

Gln Arg Ala Leu Trp Leu Leu Leu Cys Gly Cys Phe Gln Ser Lys Val
340 345 350

Pro Phe Arg Ser Arg Ser Pro Ser Glu Val
355 360

<210> SEQ ID NO 48
<211> LENGTH: 334
<212> TYPE: PRT
<213> ORGANISM: Homo sapiens

<400> SEQUENCE: 48

Met Asn Glu Asp Leu Lys Val Asn Leu Ser Gly Leu Pro Arg Asp Tyr
1 5 10 15

Leu Asp Ala Ala Ala Ala Glu Asn Ile Ser Ala Ala Val Ser Ser Arg
20 25 30

Val Pro Ala Val Glu Pro Glu Pro Glu Leu Val Val Asn Pro Trp Asp
35 40 45

Ile Val Leu Cys Thr Ser Gly Thr Leu Ile Ser Cys Glu Asn Ala Ile
50 55 60

Val Val Leu Ile Ile Phe His Asn Pro Ser Leu Arg Ala Pro Met Phe
65 70 75 80

Leu Leu Ile Gly Ser Leu Ala Leu Ala Asp Leu Leu Ala Gly Ile Gly
85 90 95

Leu Ile Thr Asn Phe Val Phe Ala Tyr Leu Leu Gln Ser Glu Ala Thr
100 105 110

Lys Leu Val Thr Ile Gly Leu Ile Val Ala Ser Phe Ser Ala Ser Val
115 120 125

Cys Ser Leu Leu Ala Ile Thr Val Asp Arg Tyr Leu Ser Leu Tyr Tyr
130 135 140

Ala Leu Thr Tyr His Ser Glu Arg Thr Val Thr Phe Thr Tyr Val Met
145 150 155 160

Leu Val Met Leu Trp Gly Thr Ser Gly Leu Leu Pro Val Met Gly Trp
165 170 175

Asn Cys Leu Arg Asp Glu Ser Thr Cys Ser Val Val Arg Pro Leu Thr
180 185 190

Lys Asn Asn Ala Ala Ile Leu Ser Val Ser Phe Leu Phe Met Phe Ala
195 200 205

Ile Cys Leu Leu Met Leu Gln Leu Tyr Ile Gln Ile Cys Lys Ile Val
210 215 220

Met Arg His Ala His Gln Ile Ala Leu Gln His His Phe Leu Ala Thr
225 230 235 240

Ser His Tyr Val Thr Thr Arg Lys Gly Val Ser Thr Leu Ala Ile Ile
245 250 255

Leu Gly Thr Phe Ala Ala Cys Trp Met Pro Phe Thr Leu Tyr Ser Leu
260 265 270

-continued

```
Ile Ala Asp Tyr Thr Tyr Pro Ser Ile Tyr Thr Tyr Ala Thr Leu Leu
        275                 280                 285

Pro Ala Thr Tyr Asn Ser Ile Ile Asn Pro Val Ile Tyr Ala Phe Arg
    290                 295                 300

Asn Gln Glu Ile Gln Lys Ala Leu Cys Leu Ile Cys Cys Gly Cys Ile
305                 310                 315                 320

Pro Ser Ser Leu Ala Gln Arg Ala Arg Ser Pro Ser Asp Val
                325                 330


<210> SEQ ID NO 49
<211> LENGTH: 234
<212> TYPE: PRT
<213> ORGANISM: Homo sapiens

<400> SEQUENCE: 49

Met Asn Leu Asn Ser Cys Leu Phe Gly Glu Thr Val Leu Leu Leu Ile
1               5                   10                  15

Ile Gly Asn Val Ile Phe Val Phe His Cys Ala Pro Leu Leu His Thr
            20                  25                  30

Thr Ser Tyr Phe Ile Gln Thr Met Ala Tyr Ala Asp Leu Phe Val Gly
        35                  40                  45

Val Ser Cys Val Pro Leu Ser Leu Leu His Val Glu Ser Leu Thr Cys
    50                  55                  60

Gln Phe Gly Ser Val Leu Lys Ser Val Ser Met Ala Leu Ala Cys Ile
65                  70                  75                  80

Ser Asp Arg Tyr Ala Ile Thr Lys Pro Leu Tyr Asn Leu Val Thr Pro
                85                  90                  95

Arg Leu Arg Cys Ile Leu Ile Trp Tyr Ser Leu Phe Leu Pro Ser Phe
            100                 105                 110

Phe Trp Gly Lys Pro Gly Tyr His Gly Asp Phe Trp Cys Ala Ser Trp
        115                 120                 125

Thr Tyr Phe Thr Phe Ile Val Leu Tyr Ala Pro Ala Ala Val Cys Phe
    130                 135                 140

Thr Tyr Phe Ile Phe Ile Cys Gln His Thr Lys Ile Arg Ala Arg Phe
145                 150                 155                 160

Ser Glu Pro Asp Arg Tyr Ala Met Val Leu Phe Arg Ile Thr Ser Val
                165                 170                 175

Phe Tyr Leu Trp Leu Pro Tyr Ile Ile Tyr Phe Leu Leu Glu Ser Ser
            180                 185                 190

Asn Ser Phe Leu Thr Thr Trp Leu Ala Ile Ser Asn Ser Phe Cys Asn
        195                 200                 205

Cys Val Ile Tyr Ser Leu Ser Asn Ser Val Phe Gly Leu Arg Leu Ser
    210                 215                 220

Met Cys Thr Ser Cys Ala Pro Asn Cys Ile
225                 230


<210> SEQ ID NO 50
<211> LENGTH: 361
<212> TYPE: PRT
<213> ORGANISM: Homo sapiens

<400> SEQUENCE: 50

Met Asn Glu Ser Arg Trp Thr Glu Trp Arg Ile Leu Asn Met Ser Ser
1               5                   10                  15

Gly Ile Val Asn Val Ser Glu Arg His Ser Cys Pro Leu Gly Phe Gly
            20                  25                  30
```

-continued

```
His Tyr Ser Val Val Asp Val Cys Ile Phe Glu Thr Val Val Ile Val
        35                  40                  45

Leu Leu Thr Phe Leu Ile Ile Ala Gly Asn Leu Thr Val Ile Phe Val
    50                  55                  60

Phe His Cys Ala Pro Leu Leu His His Tyr Thr Thr Ser Tyr Phe Ile
65                  70                  75                  80

Gln Thr Met Ala Tyr Ala Asp Leu Phe Val Gly Val Ser Cys Leu Val
                85                  90                  95

Pro Thr Leu Ser Leu Leu His Tyr Ser Thr Gly Val His Glu Ser Leu
            100                 105                 110

Thr Cys Gln Val Phe Gly Tyr Ile Ile Ser Val Leu Lys Ser Val Ser
        115                 120                 125

Met Ala Cys Leu Ala Cys Ile Ser Val Asp Arg Tyr Leu Ala Ile Thr
    130                 135                 140

Lys Pro Leu Ser Tyr Asn Gln Leu Val Thr Pro Cys Arg Leu Arg Ile
145                 150                 155                 160

Cys Ile Ile Leu Ile Trp Ile Tyr Ser Cys Leu Ile Phe Leu Pro Ser
                165                 170                 175

Phe Phe Gly Trp Gly Lys Pro Gly Tyr His Gly Asp Ile Phe Glu Trp
            180                 185                 190

Cys Ala Thr Ser Trp Leu Thr Ser Ala Tyr Phe Thr Gly Phe Ile Val
        195                 200                 205

Cys Leu Leu Tyr Ala Pro Ala Ala Phe Val Val Cys Phe Thr Tyr Phe
    210                 215                 220

His Ile Phe Lys Ile Cys Arg Gln His Thr Lys Glu Ile Asn Asp Arg
225                 230                 235                 240

Arg Ala Arg Phe Pro Ser His Glu Val Asp Ser Ser Arg Glu Thr Gly
                245                 250                 255

His Ser Pro Asp Arg Arg Tyr Ala Met Val Leu Phe Arg Ile Thr Ser
            260                 265                 270

Val Phe Tyr Met Leu Trp Leu Pro Tyr Ile Ile Tyr Phe Leu Leu Glu
        275                 280                 285

Ser Ser Arg Val Leu Asp Asn Pro Thr Leu Ser Phe Leu Thr Thr Trp
    290                 295                 300

Leu Ala Ile Ser Asn Ser Phe Cys Asn Cys Val Ile Tyr Ser Leu Ser
305                 310                 315                 320

Asn Ser Val Phe Arg Leu Gly Leu Arg Arg Leu Ser Glu Thr Met Cys
                325                 330                 335

Thr Ser Cys Met Cys Val Lys Asp Gln Glu Ala Gln Glu Pro Lys Pro
            340                 345                 350

Arg Lys Arg Ala Asn Ser Cys Ser Ile
        355                 360


<210> SEQ ID NO 51
<211> LENGTH: 349
<212> TYPE: PRT
<213> ORGANISM: Homo sapiens

<400> SEQUENCE: 51

Met Asn Ser Thr Leu Asp Gly Asn Gln Ser Ser His Pro Phe Cys Leu
1               5                   10                  15

Leu Ala Phe Gly Tyr Leu Glu Thr Val Asn Phe Cys Leu Leu Glu Val
            20                  25                  30

Leu Ile Ile Val Phe Leu Thr Val Leu Ile Ile Ser Gly Asn Ile Ile
```

-continued

```
        35                  40                  45

Val Ile Phe Val Phe His Cys Ala Pro Leu Leu Asn His His Thr Thr
    50                  55                  60

Ser Tyr Phe Ile Gln Thr Met Ala Tyr Ala Asp Leu Phe Val Gly Val
65                  70                  75                  80

Ser Cys Val Val Pro Ser Leu Ser Leu Leu His His Pro Leu Pro Val
                85                  90                  95

Glu Glu Ser Leu Thr Cys Gln Ile Phe Gly Phe Val Val Ser Val Leu
            100                 105                 110

Lys Ser Val Ser Met Ala Ser Leu Ala Cys Ile Ser Ile Asp Arg Tyr
        115                 120                 125

Ile Ala Ile Thr Lys Pro Leu Thr Tyr Asn Thr Leu Val Thr Pro Trp
    130                 135                 140

Arg Leu Arg Leu Cys Ile Phe Leu Ile Trp Leu Tyr Ser Thr Leu Val
145                 150                 155                 160

Phe Leu Pro Ser Phe Phe His Trp Gly Lys Pro Gly Tyr His Gly Asp
                165                 170                 175

Val Phe Gln Trp Cys Ala Glu Ser Trp His Thr Asp Ser Tyr Phe Thr
            180                 185                 190

Leu Phe Ile Val Met Met Leu Tyr Ala Pro Ala Ala Leu Ile Val Cys
        195                 200                 205

Phe Thr Tyr Phe Asn Ile Phe Arg Ile Cys Gln Gln His Thr Lys Asp
    210                 215                 220

Ile Ser Glu Arg Gln Ala Arg Phe Ser Ser Gln Ser Gly Glu Thr Gly
225                 230                 235                 240

Glu Val Gln Ala Cys Pro Asp Lys Lys Tyr Ala Met Val Leu Phe Arg
                245                 250                 255

Ile Thr Ser Val Phe Tyr Ile Leu Trp Leu Pro Tyr Ile Ile Tyr Phe
            260                 265                 270

Leu Leu Glu Ser Ser Thr Gly His Ser Asn Arg Phe Ala Ser Phe Leu
        275                 280                 285

Thr Thr Trp Leu Ala Ile Ser Asn Ser Phe Cys Asn Cys Val Ile Tyr
    290                 295                 300

Ser Leu Ser Asn Ser Val Phe Gln Arg Gly Leu Lys Arg Leu Ser Gly
305                 310                 315                 320

Ala Met Cys Thr Ser Cys Ala Ser Gln Thr Thr Ala Asn Asp Pro Tyr
                325                 330                 335

Thr Val Arg Ser Lys Gly Pro Leu Asn Gly Cys His Ile
            340                 345
```

<210> SEQ ID NO 52
<211> LENGTH: 4069
<212> TYPE: DNA
<213> ORGANISM: Homo sapiens

<400> SEQUENCE: 52

```
aagcttgata tcgaattcct gcagcccggg ggatccacta gttctagagc ggccgccacc     60

gcggtggagc tccagctttt gttcccttta gtgagggtta attgcgcgct agaggatctt    120

tgtgaaggaa ccttacttct gtggtgtgac ataattggac aaactaccta cagagattta    180

aagctctaag gtaaatataa aatttttaag tgtataatgt gttaaactac tgattctaat    240

tgtttgtgta ttttagattc caacctatgg aactgatgaa tgggagcagt ggtggaatgc    300

ctttaatgag gaaaacctgt tttgctcaga agaaatgcca tctagtgatg atgaggctac    360
```

-continued

```
tgctgactct caacattcta ctcctccaaa aaagaagaga aaggtagaag accccaagga    420
ctttccttca gaattgctaa gttttttgag tcatgctgtg tttagtaata gaactcttgc    480
ttgctttgct atttacacca caaaggaaaa agctgcactg ctatacaaga aaattatgga    540
aaaatattct gtaaccttta taagtaggca taacagttat aatcataaca tactgttttt    600
tcttactcca cacaggcata gagtgtctgc tattaataac tatgctcaaa aattgtgtac    660
ctttagcttt ttaatttgta aaggggttaa taaggaatat ttgatgtata gtgccttgac    720
tagagatcat aatcagccat accacatttg tagaggtttt acttgcttta aaaaacctcc    780
cacacctccc cctgaacctg aaacataaaa tgaatgcaat tgttgttgtt aacttgttta    840
ttgcagctta taatggttac aaataaagca atagcatcac aaatttcaca aataaagcat    900
ttttttcact gcattctagt tgtggtttgt ccaaactcat caatgtatct tatcatgtct    960
agatcttccg aaatgtgtgt cagttagggt gtggaaagtc cccaggctcc ccagcaggca   1020
gaagtatgca aagcatgcat ctcaattagt cagcaaccag gtgtggaaag tccccaggct   1080
ccccagcagg cagaagtatg caaagcatgc atctcaatta gtcagcaacc atagtcccgc   1140
ccctaactcc gcccatcccg cccctaactc cgcccagttc cgcccattct ccgccccatg   1200
gctgactaat tttttttatt tatgcagagg ccgaggccgc ctcggcctct gagctattcc   1260
agaagtagtg aggaggcttt tttggaggcc taggcttttg caaaaagctc cctcgagagc   1320
ttggcgtaat catggtcata gctgtttcct gtgtgaaatt gttatccgct cacaattcca   1380
cacaacatac gagccggaag cataaagtgt aaagcctggg gtgcctaatg agtgagctaa   1440
ctcacattaa ttgcgttgcg ctcactgccc gctttccagt cgggaaacct gtcgtgccag   1500
ctgcattaat gaatcggcca acgcgcgggg agaggcggtt tgcgtattgg gcgctcttcc   1560
gcttcctcgc tcactgactc gctgcgctcg gtcgttcggc tgcggcgagc ggtatcagct   1620
cactcaaagg cggtaatacg gttatccaca gaatcagggg ataacgcagg aaagaacatg   1680
tgagcaaaag gccagcaaaa ggccaggaac cgtaaaaagg ccgcgttgct ggcgtttttc   1740
cataggctcc gcccccctga cgagcatcac aaaaatcgac gctcaagtca gaggtggcga   1800
aacccgacag gactataaag ataccaggcg tttccccctg gaagctccct cgtgcgctct   1860
cctgttccga ccctgccgct taccggatac ctgtccgcct ttctcccttc gggaagcgtg   1920
gcgctttctc aatgctcacg ctgtaggtat ctcagttcgg tgtaggtcgt tcgctccaag   1980
ctgggctgtg tgcacgaacc ccccgttcag cccgaccgct gcgccttatc cggtaactat   2040
cgtcttgagt ccaacccggt aagacacgac ttatcgccac tggcagcagc cactggtaac   2100
aggattagca gagcgaggta tgtaggcggt gctacagagt tcttgaagtg gtggcctaac   2160
tacggctaca ctagaaggac agtatttggt atctgcgctc tgctgaagcc agttaccttc   2220
ggaaaaagag ttggtagctc ttgatccggc aaacaaacca ccgctggtag cggtggtttt   2280
tttgtttgca agcagcagat tacgcgcaga aaaaaaggat ctcaagaaga tcctttgatc   2340
ttttctacgg ggtctgacgc tcagtggaac gaaaactcac gttaagggat tttggtcatg   2400
agattatcaa aaaggatctt cacctagatc cttttaaatt aaaaatgaag ttttaaatca   2460
atctaaagta tatatgagta aacttggtct gacagttacc aatgcttaat cagtgaggca   2520
cctatctcag cgatctgtct atttcgttca tccatagttg cctgactccc cgtcgtgtag   2580
ataactacga tacgggaggg cttaccatct ggccccagtg ctgcaatgat accgcgagac   2640
ccacgctcac cggctccaga tttatcagca ataaaccagc cagccggaag ggccgagcgc   2700
agaagtggtc ctgcaacttt atccgcctcc atccagtcta ttaattgttg ccgggaagct   2760
```

-continued agagtaagta gttcgccagt taatagtttg cgcaacgttg ttgccattgc tacaggcatc 2820
gtggtgtcac gctcgtcgtt tggtatggct tcattcagct ccggttccca acgatcaagg 2880
cgagttacat gatcccccat gttgtgcaaa aaagcggtta gctccttcgg tcctccgatc 2940
gttgtcagaa gtaagttggc cgcagtgtta tcactcatgg ttatggcagc actgcataat 3000
tctcttactg tcatgccatc cgtaagatgc ttttctgtga ctggtgagta ctcaaccaag 3060
tcattctgag aatagtgtat gcggcgaccg agttgctctt gcccggcgtc aacacgggat 3120
aataccgcgc cacatagcag aactttaaaa gtgctcatca ttggaaaacg ttcttcgggg 3180
cgaaaactct caaggatctt accgctgttg agatccagtt cgatgtaacc cactcgtgca 3240
cccaactgat cttcagcatc ttttactttc accagcgttt ctgggtgagc aaaaacagga 3300
aggcaaaatg ccgcaaaaaa gggaataagg gcgacacgga aatgttgaat actcatactc 3360
ttcctttttc aatattattg aagcatttat cagggttatt gtctcatgcg cgttgacatt 3420
gattattgac tagttattaa tagtaatcaa ttacggggtc attagttcat agcccatata 3480
tggagttccg cgttacataa cttacggtaa atggcccgcc tggctgaccg cccaacgacc 3540
cccgcccatt gacgtcaata atgacgtatg ttcccatagt aacgccaata gggactttcc 3600
attgacgtca atgggtggac tatttacggt aaactgccca cttggcagta catcaagtgt 3660
atcatatgcc aagtacgccc cctattgacg tcaatgacgg taaatggccc gcctggcatt 3720
atgcccagta catgacctta tgggactttc ctacttggca gtacatctac gtattagtca 3780
tcgctattac catggtgatg cggttttggc agtacatcaa tgggcgtgga tagcggtttg 3840
actcacgggg atttccaagt ctccacccca ttgacgtcaa tgggagtttg ttttggcacc 3900
aaaatcaacg ggactttcca aaatgtcgta acaactccgc cccattgacg caaatgggcg 3960
gtaggcgtgt acggtgggag gtctatataa gcagagctct ctggctaact agagaaccca 4020
ctgcttaact ggcttatcga aattaatacg actcactata gggagaccc 4069

<210> SEQ ID NO 53
<211> LENGTH: 4069
<212> TYPE: DNA
<213> ORGANISM: Homo sapiens

<400> SEQUENCE: 53
gggtctccct atagtgagtc gtattaattt cgataagcca gttaagcagt gggttctcta 60
gttagccaga gagctctgct tatatagacc tcccaccgta cacgcctacc gcccatttgc 120
gtcaatgggg cggagttgtt acgacatttt ggaaagtccc gttgattttg gtgccaaaac 180
aaactcccat tgacgtcaat ggggtggaga cttggaaatc cccgtgagtc aaaccgctat 240
ccacgcccat tgatgtactg ccaaaaccgc atcaccatgg taatagcgat gactaatacg 300
tagatgtact gccaagtagg aaagtcccat aaggtcatgt actgggcata atgccaggcg 360
ggccatttac cgtcattgac gtcaataggg ggcgtacttg gcatatgata cacttgatgt 420
actgccaagt gggcagttta ccgtaaatag tccacccatt gacgtcaatg gaaagtccct 480
attggcgtta ctatgggaac atacgtcatt attgacgtca atgggcgggg gtcgttgggc 540
ggtcagccag gcgggccatt taccgtaagt tatgtaacgc ggaactccat atatgggcta 600
tgaactaatg accccgtaat tgattactat taataactag tcaataatca atgtcaacgc 660
gcatgagaca ataaccctga taaatgcttc aataatattg aaaaaggaag agtatgagta 720
ttcaacattt ccgtgtcgcc cttattccct tttttgcggc attttgcctt cctgtttttg 780

-continued

```
ctcacccaga aacgctggtg aaagtaaaag atgctgaaga tcagttgggt gcacgagtgg    840
gttacatcga actggatctc aacagcggta agatccttga gagttttcgc cccgaagaac    900
gttttccaat gatgagcact tttaaagttc tgctatgtgg cgcggtatta tcccgtgttg    960
acgccgggca agagcaactc ggtcgccgca tacactattc tcagaatgac ttggttgagt   1020
actcaccagt cacagaaaag catcttacgg atggcatgac agtaagagaa ttatgcagtg   1080
ctgccataac catgagtgat aacactgcgg ccaacttact tctgacaacg atcggaggac   1140
cgaaggagct aaccgctttt ttgcacaaca tgggggatca tgtaactcgc cttgatcgtt   1200
gggaaccgga gctgaatgaa gccataccaa acgacgagcg tgacaccacg atgcctgtag   1260
caatggcaac aacgttgcgc aaactattaa ctggcgaact acttactcta gcttcccggc   1320
aacaattaat agactggatg gaggcggata aagttgcagg accacttctg cgctcggccc   1380
ttccggctgg ctggtttatt gctgataaat ctggagccgg tgagcgtggg tctcgcggta   1440
tcattgcagc actggggcca gatggtaagc cctcccgtat cgtagttatc tacacgacgg   1500
ggagtcaggc aactatggat gaacgaaata gacagatcgc tgagataggt gcctcactga   1560
ttaagcattg gtaactgtca gaccaagttt actcatatat actttagatt gatttaaaac   1620
ttcattttta atttaaaagg atctaggtga agatcctttt tgataatctc atgaccaaaa   1680
tcccttaacg tgagttttcg ttccactgag cgtcagaccc cgtagaaaag atcaaaggat   1740
cttcttgaga tccttttttt ctgcgcgtaa tctgctgctt gcaaacaaaa aaaccaccgc   1800
taccagcggt ggtttgtttg ccggatcaag agctaccaac tctttttccg aaggtaactg   1860
gcttcagcag agcgcagata ccaaatactg tccttctagt gtagccgtag ttaggccacc   1920
acttcaagaa ctctgtagca ccgcctacat acctcgctct gctaatcctg ttaccagtgg   1980
ctgctgccag tggcgataag tcgtgtctta ccgggttgga ctcaagacga tagttaccgg   2040
ataaggcgca gcggtcgggc tgaacggggg gttcgtgcac acagcccagc ttggagcgaa   2100
cgacctacac cgaactgaga tacctacagc gtgagcattg agaaagcgcc acgcttcccg   2160
aagggagaaa ggcggacagg tatccggtaa gcggcagggt cggaacagga gagcgcacga   2220
gggagcttcc agggggaaac gcctggtatc tttatagtcc tgtcgggttt cgccacctct   2280
gacttgagcg tcgatttttg tgatgctcgt caggggggcg gagcctatgg aaaaacgcca   2340
gcaacgcggc ctttttacgg ttcctggcct tttgctggcc ttttgctcac atgttctttc   2400
ctgcgttatc ccctgattct gtggataacc gtattaccgc ctttgagtga gctgataccg   2460
ctcgccgcag ccgaacgacc gagcgcagcg agtcagtgag cgaggaagcg gaagagcgcc   2520
caatacgcaa accgcctctc cccgcgcgtt ggccgattca ttaatgcagc tggcacgaca   2580
ggtttcccga ctggaaagcg ggcagtgagc gcaacgcaat taatgtgagt tagctcactc   2640
attaggcacc ccaggcttta cactttatgc ttccggctcg tatgttgtgt ggaattgtga   2700
gcggataaca atttcacaca ggaaacagct atgaccatga ttacgccaag ctctcgaggg   2760
agctttttgc aaaagcctag gcctccaaaa aagcctcctc actacttctg gaatagctca   2820
gaggccgagg cggcctcggc ctctgcataa ataaaaaaaa ttagtcagcc atggggcgga   2880
gaatgggcgg aactgggcgg agttaggggc gggatgggcg gagttagggg cgggactatg   2940
gttgctgact aattgagatg catgctttgc atacttctgc ctgctgggga gcctggggac   3000
tttccacacc tggttgctga ctaattgaga tgcatgcttt gcatacttct gcctgctggg   3060
gagcctgggg actttccaca ccctaactga cacacatttc ggaagatcta gacatgataa   3120
gatacattga tgagtttgga caaaccacaa ctagaatgca gtgaaaaaaa tgctttattt   3180
```

-continued

```
gtgaaatttg tgatgctatt gctttatttg taaccattat aagctgcaat aaacaagtta   3240
acaacaacaa ttgcattcat tttatgtttc aggttcaggg ggaggtgtgg gaggtttttt   3300
aaagcaagta aaacctctac aaatgtggta tggctgatta tgatctctag tcaaggcact   3360
atacatcaaa tattccttat taacccctttt acaaattaaa aagctaaagg tacacaattt   3420
ttgagcatag ttattaatag cagacactct atgcctgtgt ggagtaagaa aaaacagtat   3480
gttatgatta taactgttat gcctacttat aaaggttaca gaatattttt ccataatttt   3540
cttgtatagc agtgcagctt tttcctttgt ggtgtaaata gcaaagcaag caagagttct   3600
attactaaac acagcatgac tcaaaaaact tagcaattct gaaggaaagt ccttggggtc   3660
ttctaccttt ctcttctttt ttggaggagt agaatgttga gagtcagcag tagcctcatc   3720
atcactagat ggcatttctt ctgagcaaaa caggttttcc tcattaaagg cattccacca   3780
ctgctcccat tcatcagttc cataggttgg aatctaaaat acacaaacaa ttagaatcag   3840
tagtttaaca cattatacac ttaaaaattt tatatttacc ttagagcttt aaatctctgt   3900
aggtagtttg tccaattatg tcacaccaca gaagtaaggt tccttcacaa agatcctcta   3960
gcgcgcaatt aaccctcact aaagggaaca aaagctggag ctccaccgcg gtggcggccg   4020
ctctagaact agtggatccc ccgggctgca ggaattcgat atcaagctt               4069
```

<210> SEQ ID NO 54
<211> LENGTH: 1273
<212> TYPE: PRT
<213> ORGANISM: Homo sapiens

<400> SEQUENCE: 54

```
Lys Leu Asp Ile Glu Phe Leu Gln Pro Gly Gly Ser Thr Ser Ser Arg
1               5                   10                  15

Ala Ala Ala Thr Ala Val Glu Leu Gln Leu Leu Phe Pro Leu Val Arg
            20                  25                  30

Val Asn Cys Ala Leu Glu Asp Leu Cys Glu Gly Thr Leu Leu Leu Trp
        35                  40                  45

Cys Asp Ile Ile Gly Gln Thr Thr Tyr Arg Asp Leu Lys Leu Gly Lys
    50                  55                  60

Tyr Lys Ile Phe Lys Cys Ile Met Cys Thr Thr Asp Ser Asn Cys Leu
65                  70                  75                  80

Cys Ile Leu Asp Ser Asn Leu Trp Asn Met Gly Ala Val Val Glu Cys
                85                  90                  95

Leu Gly Lys Pro Val Leu Leu Arg Arg Asn Ala Ile Gly Tyr Cys Leu
            100                 105                 110

Ser Thr Phe Tyr Ser Ser Lys Lys Glu Glu Lys Gly Arg Arg Pro Gln
        115                 120                 125

Gly Leu Ser Phe Arg Ile Ala Lys Phe Phe Glu Ser Cys Cys Val Asn
    130                 135                 140

Ser Cys Leu Leu Cys Tyr Leu His His Lys Gly Lys Ser Cys Thr Ala
145                 150                 155                 160

Ile Gln Glu Asn Tyr Gly Lys Ile Phe Cys Asn Leu Tyr Lys Ala Gln
                165                 170                 175

Leu His Thr Val Phe Ser Tyr Ser Thr Gln Ala Ser Val Cys Tyr Leu
            180                 185                 190

Cys Ser Lys Ile Val Tyr Leu Leu Phe Asn Leu Arg Gly Gly Ile Phe
        195                 200                 205

Asp Val Cys Leu Asp Arg Ser Ser Ala Ile Pro His Leu Arg Phe Tyr
```

-continued

```
    210                 215                 220

Leu Leu Lys Thr Ser His Thr Ser Pro Thr Asn Ile Lys Met Gln Leu
225                 230                 235                 240

Leu Leu Leu Thr Cys Leu Leu Gln Leu Ile Met Val Thr Asn Lys Ala
                245                 250                 255

Ile Ala Ser Gln Ile Ser Gln Ile Lys His Phe Phe His Cys Ile Leu
            260                 265                 270

Val Val Val Cys Pro Asn Ser Ser Met Tyr Leu Ile Met Ser Arg Ser
        275                 280                 285

Ser Glu Met Cys Val Ser Gly Val Glu Ser Pro Gln Ala Pro Gln Gln
    290                 295                 300

Ala Glu Val Cys Lys Ala Cys Ile Ser Ile Ser Gln Gln Pro Gly Val
305                 310                 315                 320

Glu Ser Pro Gln Ala Pro Gln Gln Ala Glu Val Cys Lys Ala Cys Ile
                325                 330                 335

Ser Ile Ser Gln Gln Pro Ser Arg Pro Leu Arg Pro Ser Arg Pro Leu
            340                 345                 350

Arg Pro Val Pro Pro Ile Leu Arg Pro Met Ala Asp Phe Phe Leu Phe
        355                 360                 365

Met Gln Arg Pro Arg Pro Pro Arg Pro Leu Ser Tyr Ser Arg Ser Ser
    370                 375                 380

Glu Glu Ala Phe Leu Glu Ala Ala Phe Ala Lys Ser Ser Leu Glu Ser
385                 390                 395                 400

Leu Ala Ser Trp Ser Leu Phe Pro Val Asn Cys Tyr Pro Leu Thr Ile
                405                 410                 415

Pro His Asn Ile Arg Ala Gly Ser Ile Lys Cys Lys Ala Trp Gly Ala
            420                 425                 430

Val Ser Leu Thr Leu Ile Ala Leu Arg Ser Leu Pro Ala Phe Gln Ser
        435                 440                 445

Gly Asn Leu Ser Cys Gln Leu His Ile Gly Gln Arg Ala Gly Arg Gly
    450                 455                 460

Gly Leu Arg Ile Gly Arg Ser Ser Ala Ser Ser Leu Thr Asp Ser Leu
465                 470                 475                 480

Arg Ser Val Val Arg Leu Arg Arg Ala Val Ser Ala His Ser Lys Ala
                485                 490                 495

Val Ile Arg Leu Ser Thr Glu Ser Gly Asp Asn Ala Gly Lys Asn Met
            500                 505                 510

Ala Lys Gly Gln Gln Lys Ala Arg Asn Arg Lys Lys Ala Ala Leu Leu
        515                 520                 525

Ala Phe Phe His Arg Leu Arg Pro Pro Asp Glu His His Lys Asn Arg
    530                 535                 540

Arg Ser Ser Gln Arg Trp Arg Asn Pro Thr Gly Leu Arg Tyr Gln Ala
545                 550                 555                 560

Phe Pro Pro Gly Ser Ser Leu Val Arg Ser Pro Val Pro Thr Leu Pro
                565                 570                 575

Leu Thr Gly Tyr Leu Ser Ala Phe Leu Pro Ser Gly Ser Val Ala Leu
            580                 585                 590

Ser Gln Cys Ser Arg Cys Arg Tyr Leu Ser Ser Val Val Val Arg Ser
        595                 600                 605

Lys Leu Gly Cys Val His Glu Pro Pro Val Gln Pro Asp Arg Cys Ala
    610                 615                 620

Leu Ser Gly Asn Tyr Arg Leu Glu Ser Asn Pro Val Arg His Asp Leu
625                 630                 635                 640
```

-continued

```
Ser Pro Leu Ala Ala Ala Thr Gly Asn Arg Ile Ser Arg Ala Arg Tyr
            645                 650                 655

Val Gly Gly Ala Thr Glu Phe Leu Lys Trp Trp Pro Asn Tyr Gly Tyr
        660                 665                 670

Thr Arg Arg Thr Val Phe Gly Ile Cys Ala Leu Leu Lys Pro Val Thr
    675                 680                 685

Phe Gly Lys Arg Val Gly Ser Ser Ser Gly Lys Gln Thr Thr Ala Gly
    690                 695                 700

Ser Gly Gly Phe Phe Val Cys Lys Gln Gln Ile Thr Arg Arg Lys Lys
705                 710                 715                 720

Gly Ser Gln Glu Asp Pro Leu Ile Phe Ser Thr Gly Ser Asp Ala Gln
            725                 730                 735

Trp Asn Glu Asn Ser Arg Gly Ile Leu Val Met Arg Leu Ser Lys Arg
        740                 745                 750

Ile Phe Thr Ile Leu Leu Asn Lys Ser Phe Lys Ser Ile Ser Ile Tyr
    755                 760                 765

Glu Thr Trp Ser Asp Ser Tyr Gln Cys Leu Ile Ser Glu Ala Pro Ile
    770                 775                 780

Ser Ala Ile Cys Leu Phe Arg Ser Ser Ile Val Ala Leu Pro Val Val
785                 790                 795                 800

Ile Thr Thr Ile Arg Glu Gly Leu Pro Ser Gly Pro Ser Ala Ala Met
            805                 810                 815

Ile Pro Arg Asp Pro Arg Ser Pro Ala Pro Asp Leu Ser Ala Ile Asn
        820                 825                 830

Gln Pro Ala Gly Arg Ala Glu Arg Arg Ser Gly Pro Ala Thr Leu Ser
    835                 840                 845

Ala Ser Ile Gln Ser Ile Asn Cys Cys Arg Glu Ala Arg Val Ser Ser
    850                 855                 860

Ser Pro Val Asn Ser Leu Arg Asn Val Val Ala Ile Ala Thr Gly Ile
865                 870                 875                 880

Val Val Ser Arg Ser Ser Phe Gly Met Ala Ser Phe Ser Ser Gly Ser
            885                 890                 895

Gln Arg Ser Arg Arg Val Thr Ser Pro Met Leu Cys Lys Lys Ala Val
        900                 905                 910

Ser Ser Phe Gly Pro Pro Ile Val Val Arg Ser Lys Leu Ala Ala Val
    915                 920                 925

Leu Ser Leu Met Val Met Ala Ala Leu His Asn Ser Leu Thr Val Met
    930                 935                 940

Pro Ser Val Arg Cys Phe Ser Val Thr Gly Glu Tyr Ser Thr Lys Ser
945                 950                 955                 960

Phe Glu Cys Met Arg Arg Pro Ser Cys Ser Cys Pro Ala Ser Thr Arg
            965                 970                 975

Asp Asn Thr Ala Pro His Ser Arg Thr Leu Lys Val Leu Ile Ile Gly
        980                 985                 990

Lys Arg Ser Ser Gly Arg Lys Leu  Ser Arg Ile Leu Pro  Leu Leu Arg
    995                 1000                1005

Ser Ser  Ser Met Pro Thr Arg  Ala Pro Asn Ser Ser  Ala Ser Phe
    1010                1015                1020

Thr Phe  Thr Ser Val Ser Gly  Ala Lys Thr Gly Arg  Gln Asn Ala
    1025                1030                1035

Ala Lys  Lys Gly Ile Arg Ala  Thr Arg Lys Cys Ile  Leu Ile Leu
    1040                1045                1050
```

-continued

```
Phe Leu Phe Gln Tyr Tyr Ser Ile Tyr Gln Gly Tyr Cys Leu Met
    1055                1060                1065

Arg Val Asp Ile Asp Tyr Leu Val Ile Asn Ser Asn Gln Leu Arg
    1070                1075                1080

Gly His Phe Ile Ala His Ile Trp Ser Ser Ala Leu His Asn Leu
    1085                1090                1095

Arg Met Ala Arg Leu Ala Asp Arg Pro Thr Thr Pro Ala His Arg
    1100                1105                1110

Gln Arg Met Phe Pro Arg Gln Gly Leu Ser Ile Asp Val Asn Gly
    1115                1120                1125

Trp Thr Ile Tyr Gly Lys Leu Pro Thr Trp Gln Tyr Ile Lys Cys
    1130                1135                1140

Ile Ile Cys Gln Val Arg Pro Leu Leu Thr Ser Met Thr Val Asn
    1145                1150                1155

Gly Pro Pro Gly Ile Met Pro Ser Thr Pro Tyr Gly Thr Phe Leu
    1160                1165                1170

Leu Gly Ser Thr Ser Thr Tyr Ser Ser Leu Leu Pro Trp Cys Gly
    1175                1180                1185

Phe Gly Ser Thr Ser Met Gly Val Asp Ser Gly Leu Thr His Gly
    1190                1195                1200

Asp Phe Gln Val Ser Thr Pro Leu Thr Ser Met Gly Val Cys Phe
    1205                1210                1215

Gly Thr Lys Ile Asn Gly Thr Phe Gln Asn Val Val Thr Thr Pro
    1220                1225                1230

Pro His Arg Lys Trp Ala Val Gly Val Tyr Gly Gly Arg Ser Ile
    1235                1240                1245

Ala Glu Leu Ser Gly Leu Glu Asn Pro Leu Leu Asn Trp Leu Ile
    1250                1255                1260

Glu Ile Asn Thr Thr His Tyr Arg Glu Thr
    1265                1270


<210> SEQ ID NO 55
<211> LENGTH: 1310
<212> TYPE: PRT
<213> ORGANISM: Homo sapiens

<400> SEQUENCE: 55

Ser Leu Ile Ser Asn Ser Cys Ser Pro Gly Asp Pro Leu Val Leu Glu
1               5                   10                  15

Arg Pro Pro Pro Arg Trp Ser Ser Ser Phe Cys Ser Leu Gly Leu Ile
            20                  25                  30

Ala Arg Arg Ile Phe Val Lys Glu Pro Tyr Phe Cys Gly Val Thr Leu
        35                  40                  45

Asp Lys Leu Pro Thr Glu Ile Ser Ser Lys Val Asn Ile Lys Phe Leu
    50                  55                  60

Ser Val Cys Val Lys Leu Leu Ile Leu Ile Val Cys Val Phe Ile Pro
65                  70                  75                  80

Thr Tyr Gly Thr Asp Glu Trp Glu Gln Trp Trp Asn Ala Phe Asn Glu
                85                  90                  95

Glu Asn Leu Phe Cys Ser Glu Glu Met Pro Ser Ser Asp Asp Glu Ala
            100                 105                 110

Thr Ala Asp Ser Gln His Ser Thr Pro Pro Lys Lys Lys Arg Lys Val
        115                 120                 125

Glu Asp Pro Lys Asp Phe Pro Ser Glu Leu Leu Ser Phe Leu Ser His
    130                 135                 140
```

-continued

```
Ala Val Phe Ser Asn Arg Thr Leu Ala Cys Phe Ala Ile Tyr Thr Thr
145                 150                 155                 160

Lys Glu Lys Ala Ala Leu Leu Tyr Lys Lys Ile Met Glu Lys Tyr Ser
                165                 170                 175

Val Thr Phe Ile Ser Arg His Asn Ser Tyr Asn His Asn Ile Leu Phe
            180                 185                 190

Phe Leu Thr Pro His Arg His Arg Val Ser Ala Ile Asn Asn Tyr Ala
        195                 200                 205

Gln Lys Leu Cys Thr Phe Ser Phe Leu Ile Cys Lys Gly Val Asn Lys
    210                 215                 220

Glu Tyr Leu Met Tyr Ser Ala Leu Thr Arg Asp His Asn Gln Pro Tyr
225                 230                 235                 240

His Ile Cys Arg Gly Phe Thr Cys Phe Lys Lys Pro Pro Thr Pro Pro
                245                 250                 255

Pro Glu Pro Glu Thr Asn Glu Cys Asn Cys Cys Cys Leu Val Tyr Cys
            260                 265                 270

Ser Leu Trp Leu Gln Ile Lys Gln His His Lys Phe His Lys Ser Ile
        275                 280                 285

Phe Phe Thr Ala Phe Leu Trp Phe Val Gln Thr His Gln Cys Ile Leu
    290                 295                 300

Ser Cys Leu Asp Leu Pro Lys Cys Val Ser Val Arg Val Trp Lys Val
305                 310                 315                 320

Pro Arg Leu Pro Ser Arg Gln Lys Tyr Ala Lys His Ala Ser Gln Leu
                325                 330                 335

Val Ser Asn Gln Val Trp Lys Val Pro Arg Leu Pro Ser Arg Gln Lys
            340                 345                 350

Tyr Ala Lys His Ala Ser Gln Leu Val Ser Asn His Ser Pro Ala Pro
        355                 360                 365

Asn Ser Ala His Pro Ala Pro Asn Ser Ala Gln Phe Arg Pro Phe Ser
    370                 375                 380

Ala Pro Trp Leu Thr Asn Phe Phe Tyr Leu Cys Arg Gly Arg Gly Arg
385                 390                 395                 400

Leu Gly Leu Ala Ile Pro Glu Val Val Arg Arg Leu Phe Trp Arg Pro
                405                 410                 415

Arg Leu Leu Gln Lys Ala Pro Ser Arg Ala Trp Arg Asn His Gly His
            420                 425                 430

Ser Cys Phe Leu Cys Glu Ile Val Ile Arg Ser Gln Phe His Thr Thr
        435                 440                 445

Tyr Glu Pro Glu Ala Ser Val Lys Pro Gly Val Pro Asn Glu Ala Asn
    450                 455                 460

Ser His Leu Arg Cys Ala His Cys Pro Leu Ser Ser Arg Glu Thr Cys
465                 470                 475                 480

Arg Ala Ser Cys Ile Asn Glu Ser Ala Asn Ala Arg Gly Glu Ala Val
                485                 490                 495

Cys Val Leu Gly Ala Leu Pro Leu Pro Arg Ser Leu Thr Arg Cys Ala
            500                 505                 510

Arg Ser Phe Gly Cys Gly Glu Arg Tyr Gln Leu Thr Gln Arg Arg Tyr
        515                 520                 525

Gly Tyr Pro Gln Asn Gln Gly Ile Thr Gln Glu Arg Thr Cys Glu Gln
    530                 535                 540

Lys Ala Ser Lys Arg Pro Gly Thr Val Lys Arg Pro Arg Cys Trp Arg
545                 550                 555                 560
```

-continued

```
Phe Ser Ile Gly Ser Ala Pro Leu Thr Ser Ile Thr Lys Ile Asp Ala
                565                 570                 575

Gln Val Arg Gly Gly Glu Thr Arg Gln Asp Tyr Lys Asp Thr Arg Arg
            580                 585                 590

Phe Pro Leu Glu Ala Pro Ser Cys Ala Leu Leu Phe Arg Pro Cys Arg
        595                 600                 605

Leu Pro Asp Thr Cys Pro Pro Phe Ser Leu Arg Glu Ala Trp Arg Phe
    610                 615                 620

Leu Asn Ala His Ala Val Gly Ile Ser Val Arg Cys Arg Ser Phe Ala
625                 630                 635                 640

Pro Ser Trp Ala Val Cys Thr Asn Pro Pro Phe Ser Pro Thr Ala Ala
                645                 650                 655

Pro Tyr Pro Val Thr Ile Val Leu Ser Pro Thr Arg Asp Thr Thr Tyr
            660                 665                 670

Arg His Trp Gln Gln Pro Leu Val Thr Gly Leu Ala Glu Arg Gly Met
        675                 680                 685

Ala Val Leu Gln Ser Ser Ser Gly Gly Leu Thr Thr Ala Thr Leu Glu
    690                 695                 700

Gly Gln Tyr Leu Val Ser Ala Leu Cys Ser Gln Leu Pro Ser Glu Lys
705                 710                 715                 720

Glu Leu Val Ala Leu Asp Pro Ala Asn Lys Pro Pro Leu Val Ala Val
                725                 730                 735

Val Phe Leu Phe Ala Ser Ser Arg Leu Arg Ala Glu Lys Lys Asp Leu
            740                 745                 750

Lys Lys Ile Leu Ser Phe Leu Arg Gly Leu Thr Leu Ser Gly Thr Lys
        755                 760                 765

Thr His Val Lys Gly Phe Trp Ser Asp Tyr Gln Lys Gly Ser Ser Pro
    770                 775                 780

Arg Ser Phe Ile Lys Asn Glu Val Leu Asn Gln Ser Lys Val Tyr Met
785                 790                 795                 800

Ser Lys Leu Gly Leu Thr Val Thr Asn Ala Ser Val Arg His Leu Ser
                805                 810                 815

Gln Arg Ser Val Tyr Phe Val His Pro Leu Pro Asp Ser Pro Ser Cys
            820                 825                 830

Arg Leu Arg Tyr Gly Arg Ala Tyr His Leu Ala Pro Val Leu Gln Tyr
        835                 840                 845

Arg Glu Thr His Ala His Arg Leu Gln Ile Tyr Gln Gln Thr Ser Gln
    850                 855                 860

Pro Glu Gly Pro Ser Ala Glu Val Val Leu Gln Leu Tyr Pro Pro Pro
865                 870                 875                 880

Ser Ser Leu Leu Ile Val Ala Gly Lys Leu Glu Val Val Arg Gln Leu
                885                 890                 895

Ile Val Cys Ala Thr Leu Leu Pro Leu Leu Gln Ala Ser Trp Cys His
            900                 905                 910

Ala Arg Arg Leu Val Trp Leu His Ser Ala Pro Val Pro Asn Asp Gln
        915                 920                 925

Gly Glu Leu His Asp Pro Pro Cys Cys Ala Lys Lys Arg Leu Ala Pro
    930                 935                 940

Ser Val Leu Arg Ser Leu Ser Glu Val Ser Trp Pro Gln Cys Tyr His
945                 950                 955                 960

Ser Trp Leu Trp Gln His Cys Ile Ile Leu Leu Leu Ser Cys His Pro
                965                 970                 975

Asp Ala Phe Leu Leu Val Ser Thr Gln Pro Ser His Ser Glu Asn Ser
```

-continued

```
            980                 985                 990

Val Cys Gly Asp Arg Val Ala Leu  Ala Arg Arg Gln His  Gly Ile Ile
        995                 1000                1005

Pro Arg  His Ile Ala Glu Leu  Lys Cys Ser Ser Leu  Glu Asn Val
    1010                 1015                 1020

Leu Arg  Gly Glu Asn Ser Gln  Gly Ser Tyr Arg Cys  Asp Pro Val
    1025                 1030                 1035

Arg Cys  Asn Pro Leu Val His  Pro Thr Asp Leu Gln  His Leu Leu
    1040                 1045                 1050

Leu Ser  Pro Ala Phe Leu Gly  Glu Gln Lys Gln Glu  Gly Lys Met
    1055                 1060                 1065

Pro Gln  Lys Arg Glu Gly Arg  His Gly Asn Val Glu  Tyr Ser Tyr
    1070                 1075                 1080

Ser Ser  Phe Phe Asn Ile Ile  Glu Ala Phe Ile Arg  Val Ile Val
    1085                 1090                 1095

Ser Cys  Ala Leu Thr Leu Ile  Ile Asp Leu Leu Ile  Val Ile Asn
    1100                 1105                 1110

Tyr Gly  Val Ile Ser Ser Pro  Ile Tyr Gly Val Pro  Arg Tyr Ile
    1115                 1120                 1125

Thr Tyr  Gly Lys Trp Pro Ala  Trp Leu Thr Ala Gln  Arg Pro Pro
    1130                 1135                 1140

Pro Ile  Asp Val Asn Asn Asp  Val Cys Ser His Ser  Asn Ala Asn
    1145                 1150                 1155

Arg Asp  Phe Pro Leu Thr Ser  Met Gly Gly Leu Phe  Thr Val Asn
    1160                 1165                 1170

Cys Pro  Leu Gly Ser Thr Ser  Ser Val Ser Tyr Ala  Lys Tyr Ala
    1175                 1180                 1185

Pro Tyr  Arg Gln Arg Met Ala  Arg Leu Ala Leu Cys  Pro Val His
    1190                 1195                 1200

Asp Leu  Met Gly Leu Ser Tyr  Leu Ala Val His Leu  Arg Ile Ser
    1205                 1210                 1215

His Arg  Tyr Tyr His Gly Asp  Ala Val Leu Ala Val  His Gln Trp
    1220                 1225                 1230

Ala Trp  Ile Ala Val Leu Thr  Gly Ile Ser Lys Ser  Pro Pro His
    1235                 1240                 1245

Arg Gln  Trp Glu Phe Val Leu  Ala Pro Lys Ser Thr  Gly Leu Ser
    1250                 1255                 1260

Lys Met  Ser Gln Leu Arg Pro  Ile Asp Ala Asn Gly  Arg Ala Cys
    1265                 1270                 1275

Thr Val  Gly Gly Leu Tyr Lys  Gln Ser Ser Leu Ala  Asn Arg Thr
    1280                 1285                 1290

His Cys  Leu Thr Gly Leu Ser  Lys Leu Ile Arg Leu  Thr Ile Gly
    1295                 1300                 1305

Arg Pro
    1310


<210> SEQ ID NO 56
<211> LENGTH: 1286
<212> TYPE: PRT
<213> ORGANISM: Homo sapiens

<400> SEQUENCE: 56

Gln Ala Tyr Arg Ile Pro Ala Ala Arg Gly Ile His Phe Ser Gly Arg
1               5                   10                  15
```

-continued

```
His Arg Gly Gly Ala Pro Ala Phe Val Pro Phe Ser Glu Gly Leu Arg
            20                  25                  30

Ala Arg Gly Ser Leu Arg Asn Leu Thr Ser Val Val His Asn Trp Thr
        35                  40                  45

Asn Tyr Leu Gln Arg Phe Lys Ala Leu Arg Ile Asn Phe Val Tyr Asn
    50                  55                  60

Val Leu Asn Tyr Phe Leu Phe Val Tyr Phe Arg Phe Gln Pro Met Glu
65                  70                  75                  80

Leu Met Asn Gly Ser Ser Gly Gly Met Pro Leu Met Arg Lys Thr Cys
                85                  90                  95

Phe Ala Gln Lys Lys Cys His Leu Val Met Met Arg Leu Leu Leu Thr
            100                 105                 110

Leu Asn Ile Leu Leu Leu Gln Lys Arg Arg Glu Arg Lys Thr Pro Arg
        115                 120                 125

Thr Phe Leu Gln Asn Cys Val Phe Val Met Leu Cys Leu Val Ile Glu
    130                 135                 140

Leu Leu Leu Ala Leu Leu Phe Thr Pro Gln Arg Lys Lys Leu His Cys
145                 150                 155                 160

Tyr Thr Arg Lys Leu Trp Lys Asn Ile Leu Pro Leu Val Gly Ile Thr
                165                 170                 175

Val Ile Ile Ile Thr Tyr Cys Phe Phe Leu Leu His Thr Gly Ile Glu
            180                 185                 190

Cys Leu Leu Leu Ile Thr Met Leu Lys Asn Cys Val Pro Leu Ala Phe
        195                 200                 205

Phe Val Lys Gly Leu Ile Arg Asn Ile Cys Ile Val Pro Leu Glu Ile
    210                 215                 220

Ile Ile Ser His Thr Thr Phe Val Glu Val Leu Leu Ala Leu Lys Asn
225                 230                 235                 240

Leu Pro His Leu Pro Leu Asn Leu Lys His Lys Met Asn Ala Ile Val
                245                 250                 255

Val Val Asn Leu Phe Ile Ala Ala Tyr Asn Gly Tyr Lys Ser Asn Ser
            260                 265                 270

Ile Thr Asn Phe Thr Asn Lys Ala Phe Phe Ser Leu His Ser Ser Cys
        275                 280                 285

Gly Leu Ser Lys Leu Ile Asn Val Ser Tyr His Val Ile Phe Arg Asn
    290                 295                 300

Val Cys Gln Leu Gly Cys Gly Lys Ser Pro Gly Ser Pro Ala Gly Arg
305                 310                 315                 320

Ser Met Gln Ser Met His Leu Asn Ser Ala Thr Arg Cys Gly Lys Ser
                325                 330                 335

Pro Gly Ser Pro Ala Gly Arg Ser Met Gln Ser Met His Leu Asn Ser
            340                 345                 350

Ala Thr Ile Val Pro Pro Leu Thr Pro Pro Ile Pro Pro Leu Thr Pro
        355                 360                 365

Pro Ser Ser Ala His Ser Pro Pro His Gly Leu Ile Phe Phe Ile Tyr
    370                 375                 380

Ala Glu Ala Glu Ala Ala Ser Ala Ser Glu Leu Phe Gln Lys Gly Gly
385                 390                 395                 400

Phe Phe Gly Gly Leu Gly Phe Cys Lys Lys Leu Pro Arg Glu Leu Gly
                405                 410                 415

Val Ile Met Val Ile Ala Val Ser Cys Val Lys Leu Leu Ser Ala His
            420                 425                 430

Asn Ser Thr Gln His Thr Ser Arg Lys His Lys Val Ser Leu Gly Cys
```

-continued

```
        435                 440                 445

Leu Met Ser Glu Leu Thr His Ile Asn Cys Val Ala Leu Thr Ala Arg
    450                 455                 460

Phe Pro Val Gly Lys Pro Val Val Pro Ala Ala Leu Met Asn Arg Pro
465                 470                 475                 480

Thr Arg Gly Glu Arg Arg Phe Ala Tyr Trp Ala Leu Phe Arg Phe Leu
                485                 490                 495

Ala His Leu Ala Ala Leu Gly Arg Ser Ala Ala Ala Ser Gly Ile Ser
            500                 505                 510

Ser Leu Lys Gly Gly Asn Thr Val Ile His Arg Ile Arg Gly Arg Arg
        515                 520                 525

Lys Glu His Val Ser Lys Arg Pro Ala Lys Gly Gln Glu Pro Lys Gly
    530                 535                 540

Arg Val Ala Gly Val Phe Pro Ala Pro Pro Pro Arg Ala Ser Gln Lys
545                 550                 555                 560

Ser Thr Leu Lys Ser Glu Val Ala Lys Pro Asp Arg Thr Ile Lys Ile
                565                 570                 575

Pro Gly Val Ser Pro Trp Lys Leu Pro Arg Ala Leu Ser Cys Ser Asp
            580                 585                 590

Pro Ala Ala Tyr Arg Ile Pro Val Arg Leu Ser Pro Phe Gly Lys Arg
        595                 600                 605

Gly Ala Phe Ser Met Leu Thr Leu Val Ser Gln Phe Gly Val Gly Arg
    610                 615                 620

Ser Leu Gln Ala Gly Leu Cys Ala Arg Thr Pro Arg Ser Ala Arg Pro
625                 630                 635                 640

Leu Arg Leu Ile Arg Leu Ser Ser Val Gln Pro Gly Lys Thr Arg Leu
                645                 650                 655

Ile Ala Thr Gly Ser Ser His Trp Gln Asp Gln Ser Glu Val Cys Arg
            660                 665                 670

Arg Cys Tyr Arg Val Leu Glu Val Val Ala Leu Arg Leu His Lys Asp
        675                 680                 685

Ser Ile Trp Tyr Leu Arg Ser Ala Glu Ala Ser Tyr Leu Arg Lys Lys
    690                 695                 700

Ser Trp Leu Leu Ile Arg Gln Thr Asn His Arg Trp Arg Trp Phe Phe
705                 710                 715                 720

Cys Leu Gln Ala Ala Asp Tyr Ala Gln Lys Lys Arg Ile Ser Arg Arg
                725                 730                 735

Ser Phe Asp Leu Phe Tyr Gly Val Arg Ser Val Glu Arg Lys Leu Thr
            740                 745                 750

Leu Arg Asp Phe Gly His Glu Ile Ile Lys Lys Asp Leu His Leu Asp
        755                 760                 765

Pro Phe Lys Leu Lys Met Lys Phe Ile Asn Leu Lys Tyr Ile Val Asn
    770                 775                 780

Leu Val Gln Leu Pro Met Leu Asn Gln Gly Thr Tyr Leu Ser Asp Leu
785                 790                 795                 800

Ser Ile Ser Phe Ile His Ser Cys Leu Thr Pro Arg Arg Val Asp Asn
                805                 810                 815

Tyr Asp Thr Gly Gly Leu Thr Ile Trp Pro Gln Cys Cys Asn Asp Thr
            820                 825                 830

Ala Arg Pro Thr Leu Thr Gly Ser Arg Phe Ile Ser Asn Lys Pro Ala
        835                 840                 845

Ser Arg Lys Gly Arg Ala Gln Lys Trp Ser Cys Asn Phe Ile Arg Leu
    850                 855                 860
```

-continued

```
His Pro Val Tyr Leu Leu Pro Gly Ser Ser Lys Phe Ala Ser Phe Ala
865                 870                 875                 880

Gln Arg Cys Cys His Cys Tyr Arg His Arg Gly Val Thr Leu Val Val
                885                 890                 895

Trp Tyr Gly Phe Ile Gln Leu Arg Phe Pro Thr Ile Lys Ala Ser Tyr
            900                 905                 910

Met Ile Pro His Val Val Gln Lys Ser Gly Leu Leu Arg Ser Ser Asp
        915                 920                 925

Arg Cys Gln Lys Val Gly Arg Ser Val Ile Thr His Gly Tyr Gly Ser
    930                 935                 940

Thr Ala Phe Ser Tyr Cys His Ala Ile Arg Lys Met Leu Phe Cys Asp
945                 950                 955                 960

Trp Val Leu Asn Gln Val Ile Leu Arg Ile Val Tyr Ala Ala Thr Glu
                965                 970                 975

Leu Leu Leu Pro Gly Val Asn Thr Gly Tyr Arg Ala Thr Gln Asn Phe
            980                 985                 990

Lys Ser Ala His His Trp Lys Thr  Phe Phe Gly Ala Lys  Thr Leu Lys
        995                 1000                1005

Asp Leu  Thr Ala Val Glu Ile  Gln Phe Asp Val Thr  His Ser Cys
    1010                 1015                 1020

Thr Gln  Leu Ile Phe Ser Ile  Phe Tyr Phe His Gln  Arg Phe Trp
    1025                 1030                 1035

Val Ser  Lys Asn Arg Lys Ala  Lys Cys Arg Lys Lys  Gly Asn Lys
    1040                 1045                 1050

Gly Asp  Thr Glu Met Leu Asn  Thr His Thr Leu Pro  Phe Ser Ile
    1055                 1060                 1065

Leu Leu  Lys His Leu Ser Gly  Leu Leu Ser His Ala  Arg His Leu
    1070                 1075                 1080

Leu Thr  Ser Tyr Ser Ile Thr  Gly Ser Leu Val His  Ser Pro Tyr
    1085                 1090                 1095

Met Glu  Phe Arg Val Thr Leu  Thr Val Asn Gly Pro  Pro Gly Pro
    1100                 1105                 1110

Pro Asn  Asp Pro Arg Pro Leu  Thr Ser Ile Met Thr  Tyr Val Pro
    1115                 1120                 1125

Ile Val  Thr Pro Ile Gly Thr  Phe His Arg Gln Trp  Val Asp Tyr
    1130                 1135                 1140

Leu Arg  Thr Ala His Leu Ala  Val His Gln Val Tyr  His Met Pro
    1145                 1150                 1155

Ser Thr  Pro Pro Ile Asp Val  Asn Asp Gly Lys Trp  Pro Ala Trp
    1160                 1165                 1170

His Tyr  Ala Gln Tyr Met Thr  Leu Trp Asp Phe Pro  Thr Trp Gln
    1175                 1180                 1185

Tyr Ile  Tyr Val Leu Val Ile  Ala Ile Thr Met Val  Met Arg Phe
    1190                 1195                 1200

Trp Gln  Tyr Ile Asn Gly Arg  Gly Arg Phe Asp Ser  Arg Gly Phe
    1205                 1210                 1215

Pro Ser  Leu His Pro Ile Asp  Val Asn Gly Ser Leu  Phe Trp His
    1220                 1225                 1230

Gln Asn  Gln Arg Asp Phe Pro  Lys Cys Arg Asn Asn  Ser Ala Pro
    1235                 1240                 1245

Leu Thr  Gln Met Gly Gly Arg  Arg Val Arg Trp Glu  Val Tyr Ile
    1250                 1255                 1260
```

-continued

```
Ser Arg  Ala Leu Trp Leu Thr  Arg Glu Pro Thr Ala  Leu Ala Tyr
    1265                 1270                 1275

Arg Asn  Tyr Asp Ser Leu Gly  Asp
    1280                 1285


<210> SEQ ID NO 57
<211> LENGTH: 1293
<212> TYPE: PRT
<213> ORGANISM: Homo sapiens

<400> SEQUENCE: 57

Trp Val Ser Leu Val Val Leu Ile Ser Ile Ser Gln Leu Ser Ser Gly
1               5                   10                  15

Phe Ser Ser Pro Glu Ser Ser Ala Tyr Ile Asp Leu Pro Pro Tyr Thr
            20                  25                  30

Pro Thr Ala His Leu Arg Gln Trp Gly Gly Val Val Thr Thr Phe Trp
        35                  40                  45

Lys Val Pro Leu Ile Leu Val Pro Lys Gln Thr Pro Ile Asp Val Asn
    50                  55                  60

Gly Val Glu Thr Trp Lys Ser Pro Val Lys Pro Leu Ser Thr Pro Ile
65                  70                  75                  80

Asp Val Leu Pro Lys Pro His His His Gly Asn Ser Asp Asp Tyr Val
                85                  90                  95

Asp Val Leu Pro Ser Arg Lys Val Pro Gly His Val Leu Gly Ile Met
            100                 105                 110

Pro Gly Gly Pro Phe Thr Val Ile Asp Val Asn Arg Gly Arg Thr Trp
        115                 120                 125

His Met Ile His Leu Met Tyr Cys Gln Val Gly Ser Leu Pro Ile Val
    130                 135                 140

His Pro Leu Thr Ser Met Glu Ser Pro Tyr Trp Arg Tyr Tyr Gly Asn
145                 150                 155                 160

Ile Arg His Tyr Arg Gln Trp Ala Gly Val Val Gly Arg Ser Ala Arg
                165                 170                 175

Arg Ala Ile Tyr Arg Lys Leu Cys Asn Ala Glu Leu His Ile Trp Ala
            180                 185                 190

Met Asn Pro Arg Asn Leu Leu Leu Ile Thr Ser Gln Ser Met Ser Thr
        195                 200                 205

Arg Met Arg Gln Pro Met Leu Gln Tyr Lys Arg Lys Ser Met Ser Ile
    210                 215                 220

Gln His Phe Arg Val Ala Leu Ile Pro Phe Phe Ala Ala Phe Cys Leu
225                 230                 235                 240

Pro Val Phe Ala His Pro Glu Thr Leu Val Lys Val Lys Asp Ala Glu
                245                 250                 255

Asp Gln Leu Gly Ala Arg Val Gly Tyr Ile Glu Leu Asp Leu Asn Ser
            260                 265                 270

Gly Lys Ile Leu Glu Ser Phe Arg Pro Glu Glu Arg Phe Pro Met Met
        275                 280                 285

Ser Thr Phe Lys Val Leu Leu Cys Gly Ala Val Leu Ser Arg Val Asp
    290                 295                 300

Ala Gly Gln Glu Gln Leu Gly Arg Arg Ile His Tyr Ser Gln Asn Asp
305                 310                 315                 320

Leu Val Glu Tyr Ser Pro Val Thr Glu Lys His Leu Thr Asp Gly Met
                325                 330                 335

Thr Val Arg Glu Leu Cys Ser Ala Ala Ile Thr Met Ser Asp Asn Thr
            340                 345                 350
```

-continued

```
Ala Ala Asn Leu Leu Leu Thr Thr Ile Gly Gly Pro Lys Glu Leu Thr
        355                 360                 365

Ala Phe Leu His Asn Met Gly Asp His Val Thr Arg Leu Asp Arg Trp
    370                 375                 380

Glu Pro Glu Leu Asn Glu Ala Ile Pro Asn Asp Glu Arg Asp Thr Thr
385                 390                 395                 400

Met Pro Val Ala Met Ala Thr Thr Leu Arg Lys Leu Leu Thr Gly Glu
                405                 410                 415

Leu Leu Thr Leu Ala Ser Arg Gln Gln Leu Ile Asp Trp Met Glu Ala
            420                 425                 430

Asp Lys Val Ala Gly Pro Leu Leu Arg Ser Ala Leu Pro Ala Gly Trp
        435                 440                 445

Phe Ile Ala Asp Lys Ser Gly Ala Gly Glu Arg Gly Ser Arg Gly Ile
    450                 455                 460

Ile Ala Ala Leu Gly Pro Asp Gly Lys Pro Ser Arg Ile Val Val Ile
465                 470                 475                 480

Tyr Thr Thr Gly Ser Gln Ala Thr Met Asp Glu Arg Asn Arg Gln Ile
                485                 490                 495

Ala Glu Ile Gly Ala Ser Leu Ile Lys His Trp Leu Ser Asp Gln Val
            500                 505                 510

Tyr Ser Tyr Ile Leu Ile Asp Leu Lys Leu His Phe Phe Lys Arg Ile
        515                 520                 525

Val Lys Ile Leu Phe Asp Asn Leu Met Thr Lys Ile Pro Arg Glu Phe
    530                 535                 540

Ser Phe His Ala Ser Asp Pro Val Glu Lys Ile Lys Gly Ser Ser Asp
545                 550                 555                 560

Pro Phe Phe Leu Arg Val Ile Cys Cys Leu Gln Thr Lys Lys Pro Pro
                565                 570                 575

Leu Pro Ala Val Val Cys Leu Pro Asp Gln Glu Leu Pro Thr Leu Phe
            580                 585                 590

Pro Lys Val Thr Gly Phe Ser Arg Ala Gln Ile Pro Asn Thr Val Leu
        595                 600                 605

Leu Val Pro Leu Gly His His Phe Lys Asn Ser Val Ala Pro Pro Thr
    610                 615                 620

Tyr Leu Ala Leu Leu Ile Leu Leu Pro Val Ala Ala Ala Ser Gly Asp
625                 630                 635                 640

Lys Ser Cys Leu Thr Gly Leu Asp Ser Arg Arg Leu Pro Asp Lys Ala
                645                 650                 655

Gln Arg Ser Gly Thr Gly Gly Ser Cys Thr Gln Pro Ser Leu Glu Arg
            660                 665                 670

Thr Thr Tyr Thr Glu Leu Arg Tyr Leu Gln Arg Glu His Glu Ser Ala
        675                 680                 685

Thr Leu Pro Glu Gly Arg Lys Ala Asp Arg Tyr Pro Val Ser Gly Arg
    690                 695                 700

Val Gly Thr Gly Glu Arg Thr Arg Glu Leu Pro Gly Gly Asn Ala Trp
705                 710                 715                 720

Tyr Leu Tyr Ser Pro Val Gly Phe Arg His Leu Leu Glu Arg Arg Phe
                725                 730                 735

Leu Cys Ser Ser Gly Gly Arg Ser Leu Trp Lys Asn Ala Ser Asn Ala
            740                 745                 750

Ala Phe Leu Arg Phe Leu Ala Phe Cys Trp Pro Phe Ala His Met Phe
        755                 760                 765
```

-continued

```
Phe Pro Ala Leu Ser Pro Asp Ser Val Asp Asn Arg Ile Thr Ala Phe
    770                 775                 780

Glu Ala Asp Thr Ala Arg Arg Ser Arg Thr Thr Glu Arg Ser Glu Ser
785                 790                 795                 800

Val Ser Glu Glu Ala Glu Glu Arg Pro Ile Arg Lys Pro Pro Leu Pro
                805                 810                 815

Ala Arg Trp Pro Ile His Cys Ser Trp His Asp Arg Phe Pro Asp Trp
            820                 825                 830

Lys Ala Gly Ser Glu Arg Asn Ala Ile Asn Val Ser Leu Thr His Ala
        835                 840                 845

Pro Gln Ala Leu His Phe Met Leu Pro Ala Arg Met Leu Cys Gly Ile
    850                 855                 860

Val Ser Gly Gln Phe His Thr Gly Asn Ser Tyr Asp His Asp Tyr Ala
865                 870                 875                 880

Lys Leu Ser Arg Glu Leu Phe Ala Lys Ala Ala Ser Lys Lys Ala Ser
                885                 890                 895

Ser Leu Leu Leu Glu Leu Arg Gly Arg Gly Gly Leu Gly Leu Cys Ile
            900                 905                 910

Asn Lys Lys Asn Ser Ala Met Gly Arg Arg Met Gly Gly Thr Gly Arg
        915                 920                 925

Ser Gly Arg Asp Gly Arg Ser Gly Arg Asp Tyr Gly Cys Leu Ile Glu
    930                 935                 940

Met His Ala Leu His Thr Ser Ala Cys Trp Gly Ala Trp Gly Leu Ser
945                 950                 955                 960

Thr Pro Gly Cys Leu Ile Glu Met His Ala Leu His Thr Ser Ala Cys
                965                 970                 975

Trp Gly Ala Trp Gly Leu Ser Thr Pro Leu Thr His Ile Ser Glu Asp
            980                 985                 990


Leu Asp Met Ile Arg Tyr Ile Asp  Glu Phe Gly Gln Thr  Thr Thr Arg
        995                 1000                1005

Met Gln  Lys Lys Cys Phe Ile  Cys Glu Ile Cys Asp  Ala Ile Ala
    1010                 1015                 1020

Leu Phe  Val Thr Ile Ile Ser  Cys Asn Lys Gln Val  Asn Asn Asn
    1025                 1030                 1035

Asn Cys  Ile His Phe Met Phe  Gln Val Gln Gly Glu  Val Trp Glu
    1040                 1045                 1050

Val Phe  Ser Lys Asn Leu Tyr  Lys Cys Gly Met Ala  Asp Tyr Asp
    1055                 1060                 1065

Leu Ser  Arg His Tyr Thr Ser  Asn Ile Pro Tyr Pro  Leu Tyr Lys
    1070                 1075                 1080

Leu Lys  Ser Arg Tyr Thr Ile  Phe Glu His Ser Tyr  Gln Thr Leu
    1085                 1090                 1095

Tyr Ala  Cys Val Glu Glu Lys  Thr Val Cys Tyr Asp  Tyr Asn Cys
    1100                 1105                 1110

Tyr Ala  Tyr Leu Arg Leu Gln  Asn Ile Phe Pro Phe  Ser Cys Ile
    1115                 1120                 1125

Ala Val  Gln Leu Phe Pro Leu  Trp Cys Lys Gln Ser  Lys Gln Glu
    1130                 1135                 1140

Phe Tyr  Tyr Thr Gln His Asp  Ser Lys Asn Leu Ala  Ile Leu Lys
    1145                 1150                 1155

Glu Ser  Pro Trp Gly Leu Leu  Pro Phe Ser Ser Phe  Leu Glu Glu
    1160                 1165                 1170
```

-continued

```
Asn Val  Glu Ser Gln Gln Pro  His His His Met Ala  Phe Leu Leu
    1175                 1180                 1185

Ser Lys  Thr Gly Phe Pro His  Arg His Ser Thr Thr  Ala Pro Ile
    1190                 1195                 1200

His Gln  Phe His Arg Leu Glu  Ser Lys Ile His Lys  Gln Leu Glu
    1205                 1210                 1215

Ser Val  Val His Ile Ile His  Leu Lys Ile Leu Tyr  Leu Pro Ser
    1220                 1225                 1230

Phe Lys  Ser Leu Val Val Cys  Pro Ile Met Ser His  His Arg Ser
    1235                 1240                 1245

Lys Val  Pro Ser Gln Arg Ser  Ser Ser Ala Gln Leu  Thr Leu Thr
    1250                 1255                 1260

Lys Gly  Asn Lys Ser Trp Ser  Ser Thr Ala Val Ala  Ala Ala Leu
    1265                 1270                 1275

Glu Leu  Val Asp Pro Pro Gly  Cys Arg Asn Ser Ile  Ser Ser Leu
    1280                 1285                 1290


<210> SEQ ID NO 58
<211> LENGTH: 1279
<212> TYPE: PRT
<213> ORGANISM: Homo sapiens

<400> SEQUENCE: 58

Gly Leu Pro Ile Val Ser Arg Ile Asn Phe Asp Lys Pro Val Lys Gln
1               5                   10                  15

Trp Val Leu Leu Ala Arg Glu Leu Cys Leu Tyr Arg Pro Pro Thr Val
            20                  25                  30

His Ala Tyr Arg Pro Phe Ala Ser Met Gly Arg Ser Cys Tyr Asp Ile
        35                  40                  45

Leu Glu Ser Pro Val Asp Phe Gly Ala Lys Thr Asn Ser His Arg Gln
    50                  55                  60

Trp Gly Gly Asp Leu Glu Ile Pro Val Ser Gln Thr Ala Ile His Ala
65                  70                  75                  80

His Cys Thr Ala Lys Thr Ala Ser Pro Trp Arg Leu Ile Arg Arg Cys
                85                  90                  95

Thr Ala Lys Glu Ser Pro Ile Arg Ser Cys Thr Gly His Asn Ala Arg
            100                 105                 110

Arg Ala Ile Tyr Arg His Arg Gln Gly Ala Tyr Leu Ala Tyr Asp Thr
        115                 120                 125

Leu Asp Val Leu Pro Ser Gly Gln Phe Thr Val Asn Ser Pro Pro Ile
    130                 135                 140

Asp Val Asn Gly Lys Ser Leu Leu Ala Leu Leu Trp Glu His Thr Ser
145                 150                 155                 160

Leu Leu Thr Ser Met Gly Gly Gly Arg Trp Ala Val Ser Gln Ala Gly
                165                 170                 175

His Leu Pro Val Met Arg Gly Thr Pro Tyr Met Gly Tyr Glu Leu Met
            180                 185                 190

Thr Pro Leu Ile Thr Ile Asn Asn Ser Ile Ile Asn Val Asn Ala His
        195                 200                 205

Glu Thr Ile Thr Leu Ile Asn Ala Ser Ile Ile Leu Lys Lys Glu Glu
    210                 215                 220

Tyr Glu Tyr Ser Thr Phe Pro Cys Arg Pro Tyr Ser Leu Phe Cys Gly
225                 230                 235                 240

Ile Leu Pro Ser Cys Phe Cys Ser Pro Arg Asn Ala Gly Glu Ser Lys
                245                 250                 255
```

-continued

```
Arg Cys Arg Ser Val Gly Cys Thr Ser Gly Leu His Arg Thr Gly Ser
            260                 265                 270

Gln Gln Arg Asp Pro Glu Phe Ser Pro Arg Arg Thr Phe Ser Asn Asp
        275                 280                 285

Glu His Phe Ser Ser Ala Met Trp Arg Gly Ile Ile Pro Cys Arg Arg
    290                 295                 300

Ala Arg Ala Thr Arg Ser Pro His Thr Leu Phe Ser Glu Leu Gly Val
305                 310                 315                 320

Leu Thr Ser His Arg Lys Ala Ser Tyr Gly Trp His Asp Ser Lys Arg
                325                 330                 335

Ile Met Gln Cys Cys His Asn His Glu His Cys Gly Gln Leu Thr Ser
            340                 345                 350

Asp Asn Asp Arg Arg Thr Glu Gly Ala Asn Arg Phe Phe Ala Gln His
        355                 360                 365

Gly Gly Ser Cys Asn Ser Pro Ser Leu Gly Thr Gly Ala Glu Ser His
    370                 375                 380

Thr Lys Arg Arg Ala His His Asp Ala Cys Ser Asn Gly Asn Asn Val
385                 390                 395                 400

Ala Gln Thr Ile Asn Trp Arg Thr Thr Tyr Ser Ser Phe Pro Ala Thr
                405                 410                 415

Ile Asn Arg Leu Asp Gly Gly Gly Ser Cys Arg Thr Thr Ser Ala Leu
            420                 425                 430

Gly Pro Ser Gly Trp Leu Val Tyr Cys Ile Trp Ser Arg Ala Trp Val
        435                 440                 445

Ser Arg Tyr His Cys Ser Thr Gly Ala Arg Trp Ala Leu Pro Tyr Arg
    450                 455                 460

Ser Tyr Leu His Asp Gly Glu Ser Gly Asn Tyr Gly Thr Lys Thr Asp
465                 470                 475                 480

Arg Asp Arg Cys Leu Thr Asp Ala Leu Val Thr Val Arg Pro Ser Leu
                485                 490                 495

Leu Ile Tyr Thr Leu Asp Phe Lys Thr Ser Phe Leu Ile Lys Asp Leu
            500                 505                 510

Gly Glu Asp Pro Phe Ser His Asp Gln Asn Pro Leu Thr Val Phe Val
        515                 520                 525

Pro Leu Ser Val Arg Pro Arg Arg Lys Asp Gln Arg Ile Phe Leu Arg
    530                 535                 540

Ser Phe Phe Ser Ala Arg Asn Leu Leu Leu Ala Asn Lys Lys Thr Thr
545                 550                 555                 560

Ala Thr Ser Gly Gly Leu Phe Ala Gly Ser Arg Ala Thr Asn Ser Phe
                565                 570                 575

Ser Glu Gly Asn Trp Leu Gln Gln Ser Ala Asp Thr Lys Tyr Cys Pro
            580                 585                 590

Ser Ser Val Ala Val Val Arg Pro Pro Leu Gln Glu Leu Cys Ser Thr
        595                 600                 605

Ala Tyr Ile Pro Arg Ser Ala Asn Pro Val Thr Ser Gly Cys Cys Gln
    610                 615                 620

Trp Arg Val Val Ser Tyr Arg Val Gly Leu Lys Thr Ile Val Thr Gly
625                 630                 635                 640

Gly Ala Ala Val Gly Leu Asn Gly Gly Phe Val His Thr Ala Gln Leu
                645                 650                 655

Gly Ala Asn Asp Leu His Arg Thr Glu Ile Pro Thr Ala Ala Leu Arg
            660                 665                 670
```

-continued

```
Lys Arg His Ala Ser Arg Arg Glu Lys Gly Gly Gln Val Ser Gly Lys
        675                 680                 685

Arg Gln Gly Arg Asn Arg Arg Ala His Glu Gly Ala Ser Arg Gly Lys
    690                 695                 700

Arg Leu Val Ser Leu Ser Cys Arg Val Ser Pro Pro Leu Thr Ala Ser
705                 710                 715                 720

Ile Phe Val Met Leu Val Arg Gly Ala Glu Pro Met Glu Lys Arg Gln
                725                 730                 735

Gln Arg Gly Leu Phe Thr Val Pro Gly Leu Leu Leu Ala Phe Cys Ser
            740                 745                 750

His Val Leu Ser Cys Val Ile Pro Phe Cys Gly Pro Tyr Tyr Arg Leu
        755                 760                 765

Val Ser Tyr Arg Ser Pro Gln Pro Asn Asp Arg Ala Gln Arg Val Ser
    770                 775                 780

Glu Arg Gly Ser Gly Arg Ala Pro Asn Thr Gln Thr Ala Ser Pro Arg
785                 790                 795                 800

Ala Leu Ala Asp Ser Leu Met Gln Leu Ala Arg Gln Val Ser Arg Leu
                805                 810                 815

Glu Ser Gly Gln Ala Gln Arg Asn Cys Glu Leu Ala His Ser Leu Gly
            820                 825                 830

Thr Pro Gly Phe Thr Leu Tyr Ala Ser Gly Ser Tyr Val Val Trp Asn
        835                 840                 845

Cys Glu Arg Ile Thr Ile Ser His Arg Lys Gln Leu Pro Leu Arg Gln
    850                 855                 860

Ala Leu Glu Gly Ala Phe Cys Lys Ser Leu Gly Leu Gln Lys Ser Leu
865                 870                 875                 880

Leu Thr Thr Ser Gly Ile Ala Gln Arg Pro Arg Arg Pro Arg Pro Leu
                885                 890                 895

His Lys Lys Lys Leu Val Ser His Gly Ala Glu Asn Gly Arg Asn Trp
            900                 905                 910

Ala Glu Leu Gly Ala Gly Trp Ala Glu Leu Gly Ala Gly Leu Trp Leu
        915                 920                 925

Leu Thr Asn Asp Ala Cys Phe Ala Tyr Phe Cys Leu Leu Gly Ser Leu
    930                 935                 940

Gly Thr Phe His Thr Trp Leu Leu Thr Asn Asp Ala Cys Phe Ala Tyr
945                 950                 955                 960

Phe Cys Leu Leu Gly Ser Leu Gly Thr Phe His Thr Leu Thr Asp Thr
                965                 970                 975

His Phe Gly Arg Ser Arg His Asp Lys Ile His Val Trp Thr Asn His
            980                 985                 990

Asn Asn Ala Val Lys Lys Met Leu  Tyr Leu Asn Leu Cys  Tyr Cys Phe
        995                 1000                1005

Ile Cys  Asn His Tyr Lys Leu  Gln Thr Ser Gln Gln  Gln Leu His
    1010                1015                1020

Ser Phe  Tyr Val Ser Gly Ser  Gly Gly Gly Val Gly  Gly Phe Leu
    1025                1030                1035

Lys Gln  Val Lys Pro Leu Gln  Met Trp Tyr Gly Leu  Ser Leu Val
    1040                1045                1050

Lys Ala  Leu Tyr Ile Lys Tyr  Ser Leu Leu Thr Pro  Leu Gln Ile
    1055                1060                1065

Lys Lys  Leu Lys Val His Asn  Phe Ala Leu Leu Ile  Ala Asp Thr
    1070                1075                1080

Leu Cys  Leu Cys Gly Val Arg  Lys Asn Ser Met Leu  Leu Leu Leu
```

-continued

```
    1085                1090                1095

Cys Leu  Leu Ile Lys Val Thr  Glu Tyr Phe Ser Ile  Ile Phe Leu
    1100                1105                1110

Tyr Ser  Ser Ala Ala Phe Ser  Phe Val Val Ile Ala  Lys Gln Ala
    1115                1120                1125

Arg Val  Leu Leu Leu Asn Thr  Ala Leu Lys Lys Leu  Ser Asn Ser
    1130                1135                1140

Glu Gly  Lys Ser Leu Gly Ser  Ser Thr Phe Leu Phe  Phe Phe Gly
    1145                1150                1155

Gly Val  Glu Cys Glu Ser Ala  Val Ala Ser Ser Ser  Leu Asp Gly
    1160                1165                1170

Ile Ser  Ser Glu Gln Asn Arg  Phe Ser Ser Leu Lys  Ala Phe His
    1175                1180                1185

His Cys  Ser His Ser Ser Val  Pro Val Gly Ile Asn  Thr Gln Thr
    1190                1195                1200

Ile Arg  Ile Ser Ser Leu Thr  His Tyr Thr Leu Lys  Asn Phe Ile
    1205                1210                1215

Phe Thr  Leu Glu Leu Ile Ser  Val Gly Ser Leu Ser  Asn Tyr Val
    1220                1225                1230

Thr Pro  Gln Lys Gly Ser Phe  Thr Lys Ile Leu Arg  Ala Ile Asn
    1235                1240                1245

Pro His  Arg Glu Gln Lys Leu  Glu Leu His Arg Gly  Gly Gly Arg
    1250                1255                1260

Ser Arg  Thr Ser Gly Ser Pro  Gly Leu Gln Glu Phe  Asp Ile Lys
    1265                1270                1275

Leu


<210> SEQ ID NO 59
<211> LENGTH: 1284
<212> TYPE: PRT
<213> ORGANISM: Homo sapiens

<400> SEQUENCE: 59

Gly Ser Pro Tyr Ser Glu Ser Tyr Phe Arg Ala Ser Ala Val Gly Ser
1               5                   10                  15

Leu Val Ser Gln Arg Ala Leu Leu Ile Thr Ser His Arg Thr Arg Leu
            20                  25                  30

Pro Pro Ile Cys Val Asn Gly Ala Glu Leu Leu Arg His Phe Gly Lys
        35                  40                  45

Ser Arg Phe Trp Cys Gln Asn Lys Leu Pro Leu Thr Ser Met Gly Trp
    50                  55                  60

Arg Leu Gly Asn Pro Arg Glu Ser Asn Arg Tyr Pro Arg Pro Leu Met
65                  70                  75                  80

Tyr Cys Gln Asn Arg Ile Thr Met Val Ile Ala Met Thr Asn Thr Met
                85                  90                  95

Tyr Cys Gln Val Gly Lys Ser His Lys Val Met Tyr Trp Ala Cys Gln
            100                 105                 110

Ala Gly His Leu Pro Ser Leu Thr Ser Ile Gly Gly Val Leu Gly Ile
        115                 120                 125

Tyr Thr Cys Thr Ala Lys Trp Ala Val Tyr Arg Lys Ser Thr His Arg
    130                 135                 140

Gln Trp Lys Val Pro Ile Gly Val Thr Met Gly Thr Tyr Val Ile Ile
145                 150                 155                 160

Asp Val Asn Gly Arg Gly Ser Leu Gly Gly Gln Pro Gly Gly Pro Phe
```

-continued

```
            165                 170                 175

Thr Val Ser Tyr Val Thr Arg Asn Ser Ile Tyr Gly Leu Thr Asn Asp
        180                 185                 190

Pro Val Ile Asp Tyr Tyr Leu Val Asn Asn Gln Cys Gln Arg Ala Asp
    195                 200                 205

Asn Asn Pro Asp Lys Cys Phe Asn Asn Ile Glu Lys Gly Arg Val Val
    210                 215                 220

Phe Asn Ile Ser Val Ser Pro Leu Phe Pro Phe Leu Arg His Phe Ala
225                 230                 235                 240

Phe Leu Phe Leu Leu Thr Gln Lys Arg Trp Lys Lys Met Leu Lys Ile
            245                 250                 255

Ser Trp Val His Glu Trp Val Thr Ser Asn Trp Ile Ser Thr Ala Val
        260                 265                 270

Arg Ser Leu Arg Val Phe Ala Pro Lys Asn Val Phe Gln Ala Leu Leu
        275                 280                 285

Lys Phe Cys Tyr Val Ala Arg Tyr Tyr Pro Val Leu Thr Pro Gly Lys
    290                 295                 300

Ser Asn Ser Val Ala Ala Tyr Thr Ile Leu Arg Met Thr Trp Leu Ser
305                 310                 315                 320

Thr His Gln Ser Gln Lys Ser Ile Leu Arg Met Ala Gln Glu Asn Tyr
            325                 330                 335

Ala Val Leu Pro Pro Val Ile Thr Leu Arg Pro Thr Tyr Phe Gln Arg
        340                 345                 350

Ser Glu Asp Arg Arg Ser Pro Leu Phe Cys Thr Thr Trp Gly Ile Met
        355                 360                 365

Leu Ala Leu Ile Val Gly Asn Arg Ser Met Lys Pro Tyr Gln Thr Thr
    370                 375                 380

Ser Val Thr Pro Arg Cys Leu Gln Trp Gln Gln Arg Cys Ala Asn Tyr
385                 390                 395                 400

Leu Ala Asn Tyr Leu Leu Leu Pro Gly Asn Asn Thr Gly Trp Arg Arg
            405                 410                 415

Ile Lys Leu Gln Asp His Phe Cys Ala Arg Pro Phe Arg Leu Ala Gly
        420                 425                 430

Leu Leu Leu Ile Asn Leu Glu Pro Val Ser Val Gly Leu Ala Val Ser
        435                 440                 445

Leu Gln His Trp Gly Gln Met Val Ser Pro Pro Val Ser Leu Ser Thr
    450                 455                 460

Arg Arg Gly Val Arg Gln Leu Trp Met Asn Glu Ile Asp Arg Ser Leu
465                 470                 475                 480

Arg Val Pro His Leu Ser Ile Gly Asn Cys Gln Thr Lys Phe Thr His
            485                 490                 495

Ile Tyr Phe Arg Leu Ile Asn Phe Ile Phe Asn Leu Lys Gly Ser Arg
        500                 505                 510

Arg Ser Phe Leu Ile Ile Ser Pro Lys Ser Leu Asn Val Ser Phe Arg
        515                 520                 525

Ser Thr Glu Arg Gln Thr Pro Lys Arg Ser Lys Asp Leu Leu Glu Ile
    530                 535                 540

Leu Phe Phe Cys Ala Ser Ala Ala Cys Lys Gln Lys Asn His Arg Tyr
545                 550                 555                 560

Gln Arg Trp Phe Val Cys Arg Ile Lys Ser Tyr Gln Leu Phe Phe Arg
            565                 570                 575

Arg Leu Ala Ser Ala Glu Arg Arg Tyr Gln Ile Leu Ser Phe Cys Ser
        580                 585                 590
```

-continued

```
Arg Ser Ala Thr Thr Ser Arg Thr Leu His Arg Leu His Thr Ser Leu
        595                 600                 605

Cys Ser Cys Tyr Gln Trp Leu Leu Pro Val Ala Ile Ser Arg Val Leu
    610                 615                 620

Pro Gly Trp Thr Gln Asp Asp Ser Tyr Arg Ile Arg Arg Ser Gly Arg
625                 630                 635                 640

Ala Glu Arg Gly Val Arg Ala His Ser Pro Ala Trp Ser Glu Arg Pro
                645                 650                 655

Thr Pro Asn Asp Thr Tyr Ser Val Ser Ile Glu Lys Ala Pro Arg Phe
            660                 665                 670

Pro Lys Gly Glu Arg Arg Thr Gly Ile Arg Ala Ala Gly Ser Glu Gln
        675                 680                 685

Glu Ser Ala Arg Gly Ser Phe Gln Gly Glu Thr Pro Gly Ile Phe Ile
    690                 695                 700

Val Leu Ser Gly Phe Ala Thr Ser Asp Leu Ser Val Asp Phe Cys Asp
705                 710                 715                 720

Ala Arg Gln Gly Gly Gly Ala Tyr Gly Lys Thr Pro Ala Thr Arg Pro
                725                 730                 735

Phe Tyr Gly Ser Trp Pro Phe Ala Gly Leu Leu Leu Thr Cys Ser Phe
            740                 745                 750

Leu Arg Tyr Pro Leu Ile Leu Trp Ile Thr Val Leu Pro Pro Leu Ser
        755                 760                 765

Glu Leu Ile Pro Leu Ala Ala Ala Glu Arg Pro Ser Ala Ala Ser Gln
    770                 775                 780

Ala Arg Lys Arg Lys Ser Ala Gln Tyr Ala Asn Arg Leu Ser Pro Arg
785                 790                 795                 800

Val Gly Arg Phe Ile Asn Ala Ala Gly Thr Thr Gly Phe Pro Thr Gly
                805                 810                 815

Lys Arg Ala Val Ser Ala Thr Gln Leu Met Val Ser Ser Leu Ile Arg
            820                 825                 830

His Pro Arg Leu Tyr Thr Leu Cys Phe Arg Leu Val Cys Cys Val Glu
        835                 840                 845

Leu Ala Asp Asn Asn Phe Thr Gln Glu Thr Ala Met Thr Met Ile Thr
    850                 855                 860

Pro Ser Ser Arg Gly Ser Phe Leu Gln Lys Pro Arg Pro Pro Lys Lys
865                 870                 875                 880

Pro Pro His Tyr Phe Trp Asn Ser Ser Glu Ala Glu Ala Ala Ser Ala
                885                 890                 895

Ser Ala Ile Lys Lys Ile Ser Gln Pro Trp Gly Gly Glu Trp Ala Glu
            900                 905                 910

Leu Gly Gly Val Arg Gly Gly Met Gly Gly Val Arg Gly Gly Thr Met
        915                 920                 925

Val Ala Asp Leu Arg Cys Met Leu Cys Ile Leu Leu Pro Ala Gly Glu
    930                 935                 940

Pro Gly Asp Phe Pro His Leu Val Ala Asp Leu Arg Cys Met Leu Cys
945                 950                 955                 960

Ile Leu Leu Pro Ala Gly Glu Pro Gly Asp Phe Pro His Pro Asn His
                965                 970                 975

Thr Phe Arg Lys Ile Thr Asp Thr Leu Met Ser Leu Asp Lys Pro Gln
            980                 985                 990

Leu Glu Cys Ser Glu Lys Asn Ala  Leu Phe Val Lys Phe  Val Met Leu
        995                 1000                1005
```

-continued

```
Leu Leu Tyr Leu Pro Leu Ala Ala Ile Asn Lys Leu Thr Thr Thr
    1010                1015                1020

Ile Ala Phe Ile Leu Cys Phe Arg Phe Arg Gly Arg Cys Gly Arg
    1025                1030                1035

Phe Phe Lys Ala Ser Lys Thr Ser Thr Asn Val Val Trp Leu Ile
    1040                1045                1050

Met Ile Ser Ser Gln Gly Thr Ile His Gln Ile Phe Leu Ile Asn
    1055                1060                1065

Pro Phe Thr Asn Lys Ala Lys Gly Thr Gln Phe Leu Ser Ile Val
    1070                1075                1080

Ile Asn Ser Arg His Ser Met Pro Val Trp Ser Lys Lys Lys Gln
    1085                1090                1095

Tyr Val Met Ile Ile Thr Val Met Pro Thr Tyr Lys Gly Tyr Arg
    1100                1105                1110

Ile Phe Phe His Asn Phe Leu Val Gln Cys Ser Phe Phe Leu Cys
    1115                1120                1125

Gly Val Asn Ser Lys Ala Ser Lys Ser Ser Ile Thr Lys His Ser
    1130                1135                1140

Met Thr Gln Lys Thr Gln Phe Arg Lys Val Leu Gly Val Phe Tyr
    1145                1150                1155

Leu Ser Leu Leu Phe Trp Arg Ser Arg Met Leu Arg Val Ser Ser
    1160                1165                1170

Ser Leu Ile Ile Thr Arg Trp His Phe Phe Ala Lys Gln Val Phe
    1175                1180                1185

Leu Ile Lys Gly Ile Pro Pro Leu Leu Pro Phe Ile Ser Ser Ile
    1190                1195                1200

Gly Trp Asn Leu Lys Tyr Thr Asn Asn Asn Gln Phe Asn Thr Leu
    1205                1210                1215

Tyr Thr Lys Phe Tyr Ile Tyr Leu Arg Ala Leu Asn Leu Cys Arg
    1220                1225                1230

Phe Val Gln Leu Cys His Thr Thr Glu Val Arg Phe Leu His Lys
    1235                1240                1245

Asp Pro Leu Ala Arg Asn Pro Ser Leu Lys Gly Thr Lys Ala Gly
    1250                1255                1260

Ala Pro Pro Arg Trp Arg Pro Leu Asn Trp Ile Pro Arg Ala Ala
    1265                1270                1275

Gly Ile Arg Tyr Gln Ala
    1280


<210> SEQ ID NO 60
<211> LENGTH: 354
<212> TYPE: PRT
<213> ORGANISM: Homo sapiens

<400> SEQUENCE: 60

Met Gly Asn His Thr Trp Glu Gly Cys His Val Asp Ser Arg Val Asp
1               5                   10                  15

His Leu Phe Pro Pro Ser Leu Tyr Ile Phe Val Ile Gly Val Gly Leu
            20                  25                  30

Pro Thr Asn Cys Leu Ala Leu Trp Ala Ala Tyr Arg Gln Val Gln Gln
        35                  40                  45

Arg Asn Glu Leu Gly Val Tyr Leu Met Asn Leu Ser Ile Ala Asp Leu
    50                  55                  60

Leu Tyr Ile Cys Thr Leu Pro Leu Trp Val Asp Tyr Phe Leu His His
65                  70                  75                  80
```

-continued

```
Asp Asn Trp Ile His Gly Pro Gly Ser Cys Lys Leu Phe Gly Phe Ile
                85                  90                  95

Phe Tyr Thr Asn Ile Tyr Ile Ser Ile Ala Phe Leu Cys Cys Ile Ser
            100                 105                 110

Val Asp Arg Tyr Leu Ala Val Ala His Pro Leu Arg Phe Ala Arg Leu
        115                 120                 125

Arg Arg Val Lys Thr Ala Val Ala Val Ser Ser Val Val Trp Ala Thr
    130                 135                 140

Glu Leu Gly Ala Asn Ser Ala Pro Leu Phe His Asp Glu Leu Phe Arg
145                 150                 155                 160

Asp Arg Tyr Asn His Thr Phe Cys Phe Glu Lys Phe Pro Met Glu Gly
                165                 170                 175

Trp Val Ala Trp Met Asn Leu Tyr Arg Val Phe Val Gly Phe Leu Phe
            180                 185                 190

Pro Trp Ala Leu Met Leu Leu Ser Tyr Arg Gly Ile Leu Arg Ala Val
        195                 200                 205

Arg Gly Ser Val Ser Thr Glu Arg Gln Glu Lys Ala Lys Ile Lys Arg
    210                 215                 220

Leu Ala Leu Ser Leu Ile Ala Ile Val Leu Val Cys Phe Ala Pro Tyr
225                 230                 235                 240

His Val Leu Leu Leu Ser Arg Ser Ala Ile Tyr Leu Gly Arg Pro Trp
                245                 250                 255

Asp Cys Gly Phe Glu Glu Arg Val Phe Ser Ala Tyr His Ser Ser Leu
            260                 265                 270

Ala Phe Thr Ser Leu Asn Cys Val Ala Asp Pro Ile Leu Tyr Cys Leu
        275                 280                 285

Val Asn Glu Gly Ala Arg Ser Asp Val Ala Lys Ala Leu His Asn Leu
    290                 295                 300

Leu Arg Phe Leu Ala Ser Asp Lys Pro Gln Glu Met Ala Asn Ala Ser
305                 310                 315                 320

Leu Thr Leu Glu Thr Pro Leu Thr Ser Lys Arg Asn Ser Thr Ala Lys
                325                 330                 335

Ala Met Thr Gly Ser Trp Ala Ala Thr Pro Pro Pro Arg Gly Thr Arg
            340                 345                 350

Cys Ser
```

ENDOGENOUS CONSTITUTIVELY ACTIVATED G PROTEIN-COUPLED ORPHAN RECEPTORS

The benefit of commonly owned Application Ser. No. 60/094,879, filed Jul. 31, 1998; Application Ser. No. 60/106, 300, filed Oct. 30, 1998; Application Ser. No. 60/110,906, filed Dec. 4, 1998, and Application Ser. No. 60/121,851, filed Feb. 26, 1999 is hereby claimed. This patent application is a continuation-in-part of application Ser. No. 09/060, 188, filed Apr. 14, 1998. The entire disclosures of each of the forgoing patent application are hereby incorporated by reference.

FIELD OF THE INVENTION

The invention disclosed in this patent document relates to transmembrane receptors, more particularly to endogenous, constitutively active G protein-coupled receptors for which the endogenous ligand is unknown, and most particularly to the use of such receptors for the direct identification of candidate compounds via screening as agonists, partial agonists or inverse agonists to such receptors.

BACKGROUND OF THE INVENTION

A. G Protein-coupled Receptors

G protein-coupled receptors share a common structural motif. All these receptors have seven sequences of between 22 to 24 hydrophobic amino acids that form seven alpha helices, each of which spans the membrane. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. The carboxy terminus of the receptor lies intracellularly with the amino terminus in the extracellular space. It is thought that the loop joining helices five and six, as well as the carboxy terminus, interact with the G protein. Currently, Gq, Gs, Gi, and Go are G proteins that have been identified. The general structure of G protein-coupled receptors is shown in FIG. 1.

Under physiological conditions, G protein-coupled receptors exist in the cell membrane in equilibrium between two different states or conformations: an “inactive” state and an “active” state. As shown schematically in FIG. 2, a receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries such as, including but not exclusively limited to, modifications to the amino acid sequence of the receptor provide means other than ligands to stabilize the active state conformation. These means effectively stabilize the receptor in an active state by simulating the effect of a ligand binding to the receptor. Stabilization by such ligand-independent means is termed “constitutive receptor activation.” A receptor for which the endogenous ligand is unknown or not identified is referred to as an “orphan receptor.”

B. Traditional Compound Screening

Generally, the use of an orphan receptor for screening purposes to identify compounds that modulate a biological response associated with such receptor has not been possible. This is because the traditional “dogma” regarding screening of compounds mandates that the ligand for the receptor be known, whereby compounds that competitively bind with the receptor, i.e., by interfering or blocking the binding of the natural ligand with the receptor, are selected. By definition, then, this approach has no applicability with respect to orphan receptors. Thus, by adhering to this dogmatic approach to the discovery of therapeutics, the art, in essence, has taught and has been taught to forsake the use of orphan receptors unless and until the natural ligand for the receptor is discovered. The pursuit of an endogenous ligand for an orphan receptor can take several years and cost millions of dollars.

Furthermore, and given that there are an estimated 2,000 G protein-coupled receptors in the human genome, the majority of which being orphan receptors, the traditional dogma castigates a creative approach to the discovery of therapeutics to these receptors.

C. Exemplary Orphan Receptors: GPR3, GPR4, GPR6, GPR12, GPR21, GHSR, OGR1 and AL022171

GPR3 is a 330 amino acid G protein coupled receptor for which the endogenous ligand is unknown. (Marchese, A. et al. (1994) Genomics 23:609; see also, Iismaa, T. P. et al (1994) *Genomics* 24:391; see FIG. 1 for reported nucleic acid and amino acid sequence.) GPR3 is constitutively active in its endogenous form. (Eggerick, D. et al. (1995) *Biochem. J.* 389:837). GPR12 is a 334 amino acid homolog of GPR3; the endogenous ligand for GPR12 is unknown (Song, Z.-H., et al (1995) *Genomics*, 28:347; see FIG. 1 for reported amino acid sequence). GPR6 is a 362 amino acid homolog of GPR3; the endogenous ligand for GPR6 is unknown (Song, Z.-H. et al, supra.; see FIG. 1 for reported amino acid sequence). GPR6 transcripts are reported to be abundant in the human putamen and to a lesser extent in the frontal cortex, hippocampus, and hypothalamus (Heiber, M. et al. *DNA and Cell Biology* (1995) 14(1):25; see FIG. 1 for reported nucleic acid and amino acid sequences for GPR6). GPR4 has also been identified as an orphan GPCR (Heiber, M. et al, 14 *DNA Cell Biol.* 25 (1995)). OGR1, an orphan GPCR, is reported to have a high level of homology with GPR4 (Xu, Y. and Casey, G., 35 *Genomics* 397 (1996)). GPR21 is a 349 amino acid G protein coupled receptor for which the endogenous ligand is unknown (see GenBank Accession #U66580 for nucleic acid and deduced amino acid sequence). GPR21 has been reported to be located at chromosome 9q33. O’Dowd B. et al., 187 *Gene* 75 (1997). AL022171 is a human DNA sequence from clone 384F21 on chromosome 1q24. AL022171 has been identified to contain an open reading frame of 1,086 bp encoding for a 361 amino acid protein. (see GenBank Accession number AL022171). AL022171 is 68% homologous to GPR21 (see FIG. 5B). GHSR is also identified as an orphan GPCR (Howard, A. D. et al, 273 *Science* 974 (1996)).

SUMMARY OF THE INVENTION

Disclosed herein are methods for screening of candidate compounds against endogenous, constitutively activated G protein-coupled orphan receptors (GPCRs) for the direct identification of candidate compounds as agonists, inverse agonists or partial agonists to such receptors. For such screening purposes, it is preferred that an endogenous, constitutively activated orphan GPCR:G protein—fusion protein be utilized.

BRIEF DESCRIPTION OF THE DRAWINGS

FIG. 5A shows the amino acid alignment of orphan receptors GPR3, GPR6, and GPR12. FIG. 5B shows the amino acid alignment of orphan receptors GPR21 and A1022171 (Consensus #1 indicates matching residues).

FIGS. 18A–L provide a sequence diagram of the preferred vector pCMV, including restriction site locations. Nucleotide sequences are set forth as SEQ.ID.NOs.: 52 and 53, and amino acid sequences are set forth as SEQ.ID.NOs.: 54 through 59 (from top to bottom).

DETAILED DESCRIPTION

Figure 1:
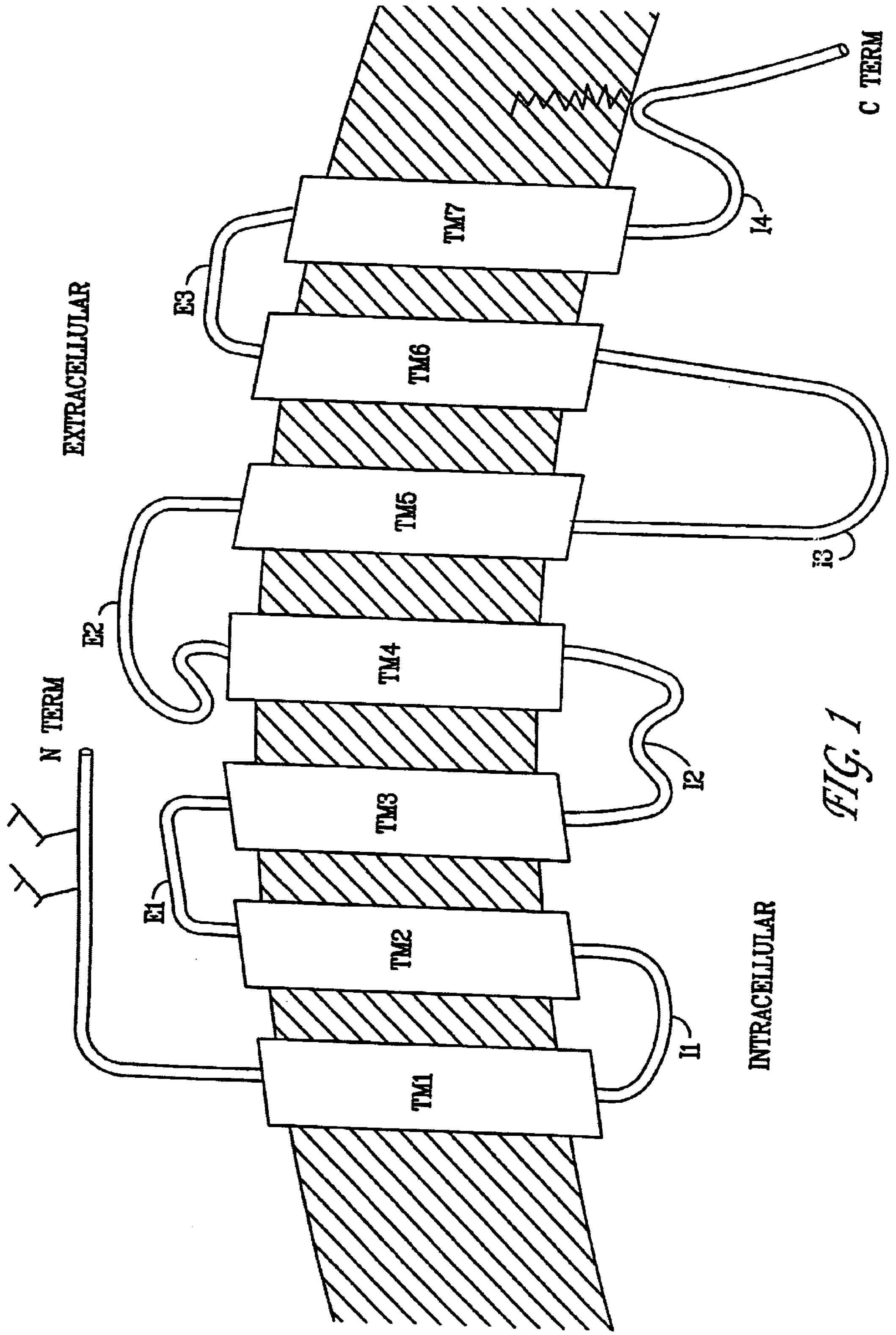
FIG. 1 shows a generalized structure of a G protein-coupled receptor with the numbers assigned to the transmembrane helixes, the intracellular loops, and the extracellular loops.
Figure 2:
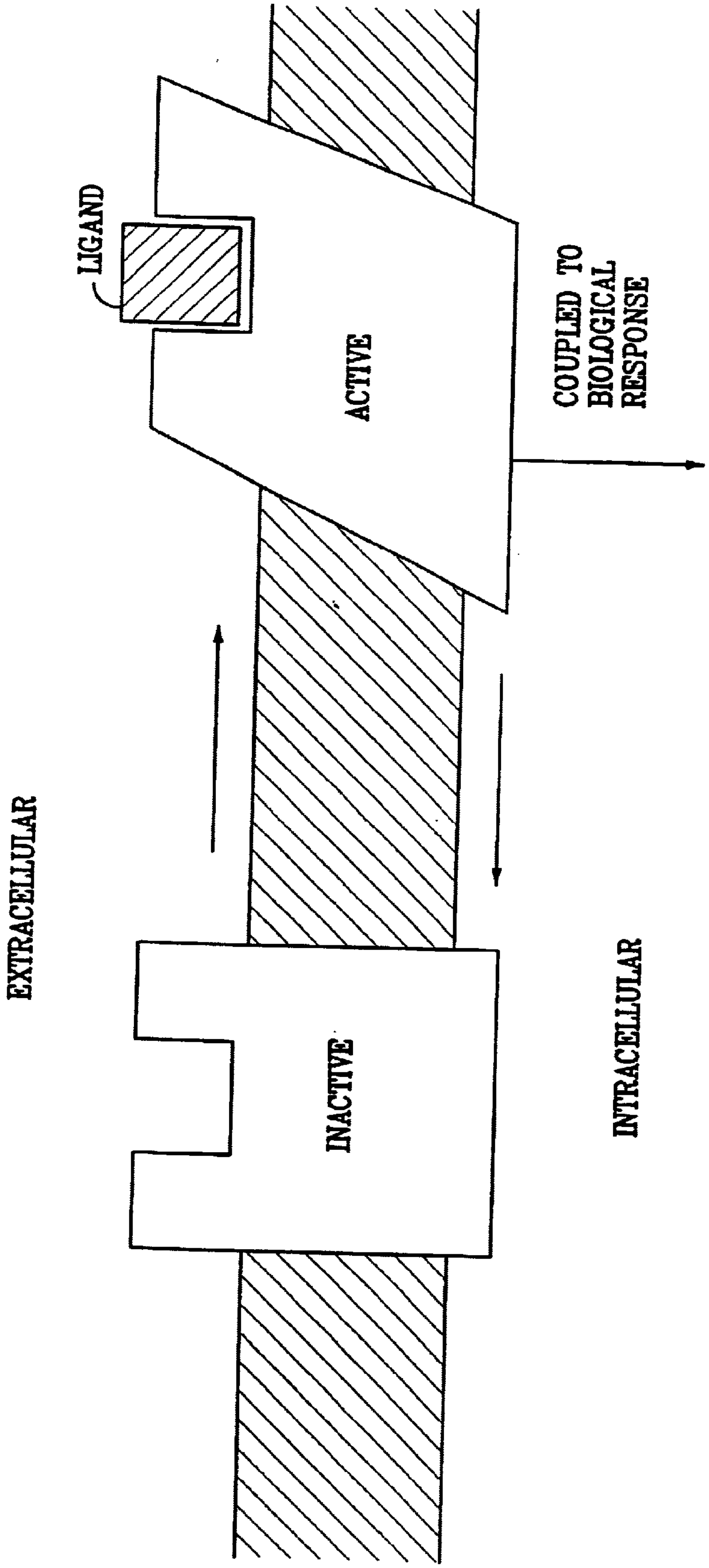
FIG. 2 schematically shows the two states, active and inactive, for a typical G protein coupled receptor and the linkage of the active state to the second messenger transduction pathway.

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean materials (e.g., ligands, candidate compounds) that activate the intracellular response when they bind to the receptor, or enhance GTP binding to membranes.

AMINO ACID ABBREVIATIONS used herein are set out in Table 1:

TABLE 1

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

PARTIAL AGONISTS shall mean materials (e.g., ligands, candidate compounds) which activate the intracellular response when they bind to the receptor to a lesser degree/extent than do agonists, or enhance GTP binding to membranes to a lesser degree/extent than do agonists.

ANTAGONIST shall mean materials (e.g., ligands, candidate compounds) that competitively bind to the receptor at the same site as the agonists but which do not activate the intracellular response initiated by the active form of the receptor, and can thereby inhibit the intracellular responses by agonists or partial agonists. ANTAGONISTS do not diminish the baseline intracellular response in the absence of an agonist or partial agonist.

CANDIDATE COMPOUND shall mean a molecule (for example, and not limitation, a chemical compound) which is amenable to a screening technique. Preferably, the phrase "candidate compound" does not include compounds which were publicly known to be compounds selected from the group consisting of inverse agonist, agonist or antagonist to a receptor, as previously determined by an indirect identification process ("indirectly identified compound"); more preferably, not including an indirectly identified compound which has previously been determined to have therapeutic efficacy in at least one mammal; and, most preferably, not including an indirectly identified compound which has previously been determined to have therapeutic utility in humans.

COMPOSITION means a material comprising at least one component; a "pharmaceutical composition" is an example of a composition.

COMPOUND EFFICACY shall mean a measurement of the ability of a compound to inhibit or stimulate receptor functionality, as opposed to receptor binding affinity. A most preferred means of detecting compound efficacy is via measurement of GTP (via [$^{35}$S]GTPγS) or cAMP, as further disclosed in the Example section of this patent document.

CONSTITUTIVELY ACTIVATED RECEPTOR (Constitutively Active Receptor) shall mean a receptor subject to constitutive receptor activation. A constitutively activated receptor can be endogenous or non-endogenous.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing at least two moieties together, whether in an in vitro system or an in vivo system.

DIRECTLY IDENTIFYING or DIRECTLY IDENTIFIED, in relationship to the phrase "candidate compound", shall mean the screening of a candidate compound against a constitutively activated receptor, preferably a constitutively activated orphan receptor, and most preferably against a constitutively activated G protein-coupled cell surface orphan receptor, and assessing the compound efficacy of such compound. This phrase is, under no circumstances, to be interpreted or understood to be encompassed by or to encompass the phrase "indirectly identifying" or "indirectly identified."

ENDOGENOUS shall mean a material that a mammal naturally produces. ENDOGENOUS in reference to, for example and not limitation, the term "receptor," shall mean that which is naturally produced by a mammal (for example, and not limitation, a human) or a virus. By contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

G PROTEIN COUPLED RECEPTOR FUSION PROTEIN and GPCR FUSION PROTEIN, in the context of the invention disclosed herein, each mean a non-endogenous protein comprising an endogenous, constitutively activated orphan GPCR fused to at least one G protein, most preferably, the alpha (α) subunit of such G protein (this being the subunit that binds GTP), with the G protein preferably being of the same type as the G protein that naturally couples with endogenous orphan GPCR. For example, and not limitation, in an endogenous state, the G protein "Gsα" is the predominate G protein that couples with GPR6 such that a GPCR Fusion Protein based upon GPR6 would be a non-endogenous protein comprising GPR6 fused to Gsα. The G protein can be fused directly to the c-terminus of the endogenous, constitutively active orphan GPCR, or there may be spacers between the two.

INDIRECTLY IDENTIFYING or INDIRECTLY IDENTIFIED means the traditional approach to the drug discovery process involving identification of an endogenous ligand specific for an endogenous receptor, screening of candidate compounds against the receptor for determination of those which interfere and/or compete with the ligand-receptor interaction, and assessing the efficacy of the compound for affecting at least one second messenger pathway associated with the activated receptor.

INHIBIT or INHIBITING, in relationship to the term "response" shall mean that a response is decreased or prevented in the presence of a compound as opposed to in the absence of the compound.

INVERSE AGONISTS shall mean materials (e.g., ligand, candidate compound) which bind to either the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

LIGAND shall mean an endogenous, naturally occurring molecule specific for an endogenous, naturally occurring receptor.

ORPHAN RECEPTOR shall mean an endogenous receptor for which the endogenous ligand specific for that receptor has not been identified or is not known.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome is based upon the needs of the artisan.

NON-ORPHAN RECEPTOR shall mean an endogenous naturally occurring molecule specific for an endogenous naturally occurring ligand wherein the binding of a ligand to a receptor activates an intracellular signaling pathway.

STIMULATE or STIMULATING, in relationship to the term "response" shall mean that a response is increased in the presence of a compound as opposed to in the absence of the compound.

The order of the following sections is set forth for presentational efficiency and is not intended, nor should be construed, as a limitation on the disclosure or the claims to follow.

A. Introduction

The traditional study of receptors has always proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been heretofore recognized is that it is the active state of the receptor that is most useful for discovering agonists, partial agonists, and inverse agonists of the receptor. For those diseases which result from an overly active receptor, what is desired in a therapeutic drug is a compound which acts to diminish the active state of a receptor, not necessarily a drug which is an antagonist to the endogenous ligand. This is because a compound (drug) which reduces the activity of the active receptor state need not bind at the same site as the endogenous ligand. Thus, as taught by a method of this invention, any search for therapeutic compounds should start by screening compounds against the ligand-independent active state. The search, then, is for an inverse agonist to the active state receptor.

Screening candidate compounds against the endogenous, constitutively activated orphan receptors, for example, and not limited to, the endogenous, constitutively active GPCRs set forth herein, GPR3, GPR4, GPR6, GPR12, GPR21, GHSR, OGR1, RE2 and AL022171, allows for the direct identification of candidate compounds which act at these orphan cell surface receptors, without requiring any prior knowledge or use of the receptor's endogenous ligand. By determining areas within the body where such receptors are expressed and/or over-expressed, it is possible to determine related disease/disorder states which are associated with the expression and/or over-expression of these receptors; such an approach is disclosed in this patent document.

B. Disease/Disorder Identification and/or Selection

As will be set forth in greater detail below, most preferably inverse agonists to endogenous, constitutively activated orphan receptors, e.g., such as those set forth herein (GPR3, GPR4, GPR6, GPR12, GPR21, GHSR, OGR1, RE2 and AL022171) can be identified by the methodologies of this invention. Such inverse agonists are ideal candidates as lead compounds in drug discovery programs for treating diseases related to these receptors. Indeed, an antagonist to such a receptor (even if the ligand were known) may be ineffective given that the receptor is activated even in the absence of ligand-receptor binding. Because of the ability to directly identify inverse agonists to these receptors, thereby allowing for the development of pharmaceutical compositions, a search, for diseases and disorders associated with these receptors is possible. For example, scanning both diseased and normal tissue samples for the presence of these orphan receptors now becomes more than an academic exercise or one which might be pursued along the path of identifying an endogenous ligand. Tissue scans can be conducted across a broad range of healthy and diseased tissues. Such tissue scans provide a preferred first step in associating a specific receptor with a disease and/or a disorder.

Preferably, the DNA sequence of the endogenous, constitutively activated GPCR is used to make a probe for RT-PCR identification of the expression of the receptor in tissue samples. The presence of a receptor in a diseased tissue, or the presence of the receptor at elevated concentrations in diseased tissue compared to normal tissue, can be utilized to identify a correlation with that disease. Receptors can equally well be localized to regions of organs by this technique. Based on the known functions of the specific tissues to which the receptor is localized, the putative functional role of the receptor can be deduced.

C. Homology Identification

The identification and association of an orphan receptor with diseases and/or disorders can be beneficially enhanced via identification of additional receptors having homology with the original orphan receptor. This approach was utilized in the identification of both GPR6 and GPR12, based upon their sequence homology with GPR3, and in the identification of AL022171, having sequence homology to GPR21. GPR3 was previously identified as a constitutively activated orphan receptor (see Eggerick, supra). What was not known, prior to this invention, was that GPR6, GPR12, GPR21 and AL022171 are also constitutively active in their endogenous states. Using known computerized databases (e.g., dbEST), GPR6, GPR12, GPR21 and AL022171 were identified.

This highlights certain unique benefits of the invention disclosed herein: because the dogma in drug screening relies upon knowledge and identification of a receptor's endogenous ligand, the art had no motivation to explore whether or not GPR3 homologs were constitutively active in their endogenous forms (other than for, at best, academic curiosity). However, with the power of the present invention to directly identify inverse agonists to such receptors, coupled with the ability to locate the distribution of such receptors in tissue samples, the present invention dramatically transcends such idle curiosity and provides a means for alleviating diseases and disorders which impact the human condition.

D. Screening of Candidate Compounds

1. Generic GPCR Screening Assay Techniques

When a G protein receptor becomes constitutively active, it binds to a G protein (e.g., Gq, Gs, Gi, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor. It is in the context of the use of a GTP assay system that a GPCR Fusion Protein is preferably utilized.

B 2. Specific GPCR Screening Assay Techniques

Once candidate compounds are identified using the "generic" G protein-coupled receptor assay (i.e. an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain. In the case of GPR3, GPR4, GPR6, GPR12, GPR21, GHSR, OGR1, RE2 and AL022171, it has been determined that these receptors couple the G protein Gs. Gs stimulates the enzyme adenylyl cyclase (Gi, on the other hand, inhibits this enzyme). Adenylyl cyclase catalyzes the conversion of ATP to cAMP; thus, because these receptors are activated in their endogenous forms, increased levels of cAMP are associated therewith (on the other hand, endogenously activated receptors which couple the Gi protein are associated with decreased levels of cAMP). See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Thus, assays that detect cAMP can be utilized to determine if a candidate compound is an inverse agonist to the receptor (i.e., such a compound which contacts the receptor would decrease the levels of cAMP relative to the uncontacted receptor). A variety of approaches known in the art for measuring cAMP can be utilized; a most preferred approach relies upon the use of anti-cAMP antibodies. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) which then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated Gs receptor such as GPR3 causes the accumulation of cAMP which then activates the gene and expression of the reporter protein. The reporter protein such as β-galactosidase or luciferase can then be detected using standard biochemical assays (see, for example, Chen. et al. 1995). A cAMP assay is particularly preferred.

The foregoing specific assay approach can, of course, be utilized to initially directly identify candidate compounds, rather than by using the generic assay approach. Such a selection is primarily a matter of choice of the artisan. With respect to GPR6, use of a modified, commercially available cAMP assay was initially utilized for the direct identification of inverse agonists.

C 3. GPCR Fusion Protein

The use of an endogenous, constitutively activated orphan GPCR for use in screening of candidate compounds for the direct identification of inverse agonists, agonists and partial agonists provides a unique challenge in that, by definition, the endogenous receptor is active even in the absence of an endogenous ligand bound thereto. Thus, in order to differentiate between, e.g., the endogenous receptor in the presence of a candidate compound and the endogenous receptor in the absence of that compound, with an aim of such a differentiation to allow for an understanding as to whether such compound may be an inverse agonist, agonist, partial agonist or have no affect on such a receptor, it is preferred that an approach be utilized that can enhance such differentiation. A preferred approach is the use of a GPCR Fusion Protein.

Generally, once it is determined that an endogenous orphan GPCR is constitutively active, using the assay techniques set forth above (as well as others), it is possible to determine the predominant G protein that couples with the endogenous GPCR. Coupling of the G protein to the GPCR provides a signaling pathway that can be assessed. Because it is most preferred that screening take place by use of a mammalian expression system, such a system will be expected to have endogenous G protein therein. Thus, by definition, in such a system, the endogenous, constitutively active orphan GPCR will continuously signal. In this regard, it is preferred that this signal be enhanced such that in the presence of, e.g., an inverse agonist to the receptor, it is more likely that one will be able to more readily differentiate, particularly in the context of screening, between the receptor when it is or is not contacted with the inverse agonist.

The GPCR Fusion Protein is intended to enhance the efficacy of G protein coupling with the endogenous GPCR. The GPCR Fusion Protein appears to be important for screening with an endogenous, constitutively activated GPCR because such an approach increases the signal that is most preferably utilized in such screening techniques. Facilitating a significant "signal to noise" ratio is important for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. One important criterion for such a GPCR Fusion Protein construct is that the endogenous GPCR sequence and the G protein sequence both be in-frame (preferably, the sequence for the endogenous GPCR is upstream of the G protein sequence) and that the "stop" codon of the GPCR must be deleted or replaced such that upon expression of the GPCR, the G protein can also be expressed. The GPCR can be linked directly to the G protein, or there can be spacer residues between the two (preferably no more than about 12, although this number can be readily ascertained by one of ordinary skill in the art). We have evaluated both approaches, and in terms of measurement of the activity of the GPCR, the results are substantially the same; however, there is a preference (based upon convenience) of use of a spacer in that some restriction sites that are not used will, effectively, upon expression, become a spacer. Most preferably, the G protein that couples to the endogenous GPCR will have been identified prior to the creation of the GPCR Fusion Protein construct. Because there are only a few G proteins that have been identified, it is preferred that a construct comprising the sequence of the G protein (i.e., a universal G protein construct) be available for insertion of an endogenous GPCR sequence therein; this provides for efficiency in the context of large-scale screening of a variety of different endogenous GPCRs having different sequences.

E. Medicinal Chemistry

Generally, but not always, direct identification of candidate compounds is preferably conducted in conjunction with compounds generated via combinatorial chemistry techniques, whereby thousands of compounds are randomly prepared for such analysis. Generally, the results of such screening will be compounds having unique core structures; thereafter, these compounds are preferably subjected to additional chemical modification around a preferred core structure(s) to further enhance the medicinal properties thereof. In this way, inverse agonists, agonists and/or partial agonists that are directly identified can be beneficially improved upon prior to development of pharmaceutical compositions comprising such compounds. Generally, it is preferred that the binding affinity of a directly identified compound selected for further refinement into a pharmaceutical composition have a binding affinity for the receptor of less than 100 nM, although this is generally a preference selection based upon the particular needs of the artisan. Such techniques are known to those in the art and will not be addressed in detail in this patent document.

F. Pharmaceutical Compositions

Candidate compounds selected for further development can be formulated into pharmaceutical compositions using techniques well known to those in the art. Suitable pharmaceutically-acceptable carriers are available to those in the art; for example, see Remington's Pharmaceutical Sciences, $16^{th}$ Edition, 1980, Mack Publishing Co., (Oslo et al., eds.).

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. It is intended that equivalent, endogenous, constitutively activated human orphan receptor sequences having eighty-five percent (85%) homology, more preferably having ninety percent (90%) homology, and most preferably having grater than ninety-five percent (95%) homology to GPR3, GPR4, GPR6, GPR12, GPR21, GHSR, OGR1, RE2 and AL022171 fall within the scope of any claims appended hereto.

Example 1

Preparation of In Situ Probes

In situ probes for GPR3, GPR6, and GPR12 were prepared. The following PCR protocol was utilized for all three probes: the reaction condition utilized was 1×rTth DNA polymerase buffer II, 1.5 mM $Mg(OAc)_2$, 0.2 mM each of the 4 nucleotides, 0.228 $\mu$g rat genomic DNA, 0.25$\mu$M of each primer (see below) and 1 unit of rTth DNA polymerase (Perkin Elmer) in 50$\mu$l reaction volume. The cycle condition was 30 cycles of 94° C. for 1 min, 55° C. for 1 min and 72° C. for 45 sec with a Perkin Elmer Cetus 2400 thermal cycler.

1. Rat GPR3 In Situ Probe

Because the full length cDNA sequence for rat GPR3 is not data-base available, the DNA fragment for the in situ probe was obtained by PCR using a 3' degenerate oligonucleotide based on the published human and mouse GPR3 sequences in the middle of the transmembrane domain 3, and a 5' degenerate oligonucleotide near the beginning of the 5' extracellular domain. The sequences of the oligonucleotides utilized were as follows: 5'-GGAGGATCCATGGCCTGGTTCTCAGC-3' (SEQ.ID.NO.:1; 5' oligo) 5'-CACAAGCTTAGRCCRTCC MG RCARTTCCA-3' (SEQ.ID.NO.:2; 3' oligo) where R=A or G, and M=A or C.

A 537 bp PCR fragment containing nucleotide 24 through to the middle of transmembrane 3 was digested with Bam HI and Hind III and was subcloned into a Bam HI-Hind III site of pBluescript.

2. Rat GPR 6 In Situ Probe

The in situ probe DNA fragment of rat GPR6 was obtained by PCR based on the published rat GPR6 cDNA sequences. The sequences of the oligonucleotides utilized were as follows:

5'-GGAGAAGCTTCTGGCGGCGATGAACGCTAG-3' (SEQ.ID.NO.:3; 5' oligo)

5'-ACAGGATCCAGGTGGCTGCTAGCAAGAG-3' (SEQ.ID.NO.:4; 3' oligo)

A 608 bp PCR fragment containing nucleotide—10 through to the middle of transmembrane domain 4 was digested with Bam HI and Hind III and was subcloned into Bam HI-Hind III site of pBluescript.

3. Rat GPR12 In Situ Probe

The in situ probe DNA fragment of rat GPR12 was obtained by PCR based on the published rat GPR12 cDNA sequences. The sequences of the oligonucleotides utilized were as follows:

5'-CTTAAGCTTAAAATGAACGAAGACCCGAAG-3' (SEQ.ID.NO.:5; 5' oligo)

5'-GGAGGATCCCCAGAGCATCACTAGCAT-3' (SEQ.ID.NO.:6; 3' oligo)

A 516 bp PCR fragment containing nucleotide—5 through to the middle of transmembrane domain 4 was digested with Bam HI and Hind III and subcloned into a Bam HI-Hind III site of pBluescript.

In situ probe sequences generated were as follows:

Rat GPR3 Probe:

GGAGGATCCATGGCCTGGTTCTCAGCCG-
GCTCAGGCAGTGTGAATGTGAGCATA-
GACCCAGCAGAGGAACCTACAGGC-
CCAGCTACACTGCTGCCCTCTCCCAGGGCCTG
GGATGTGGTGCTGTGCATCTCAGGCA CCCTG-
GTGTCCTGCGAGAATGCTCTGGTGATG-
GCCATCATTGTGGGCACGCCTGCCTTC-
CGCGCCCCCATGTTCCTGCTGGTGGGCAGCTT
GGCCGTAGCAGACCTGCTGGCAGGC-
CTGGGCCTGGTCCTGCACTTCGCT GCTGACT-
TCTGTATTGGCTCACCAGAGATGAGCT-
TGGTGCTGGTTGGCGTGCTAGCAACGGCCTTTA
CTGCCAGCATCGGCAGCCTGCTGGCCAT-
CACCGTTGACCGCTACCTTTCCCTGTA-
CAACGCCCTCACCTACTA CTCAGAGACAA-
CAGTAACTCGAACCTACGTGATGCTGGCCTTG
GTGTGGGTGGGTGCCCTGGGCCTGGGGCTGGT
TCCCGTGCTGGCCTGGAACTGCCGG-
GACGGTCTAAGCTT (SEQ.ID.NO.: 7)

Rat GPR6 Probe:

AAGCTTCTGGCGGCGATGAACGCT AGCGCCGC-
CGCGCTCAACGAGTCCCAGGTGGTG-
GCAGTAGCGGCCGAGGGAGCGGCAGCT-
GCGGCTACAGCAGCAGGGACACCGGACACCA
GCGAATGGGGACCTCCGGCAGCATC-
CGCGGCGCTGGGAGGCGGCGGAGGAC-
CTAACGGGT CACTGGAGCTGTCTTCGCAGCT-
GCCCGCAGGACCCTCAGGACTTCTGCTTTCGG
CAGTGAATCCCTGGGATGTGCTGCTGT-
GCGTGTCGGGGACTGTGATC GCAGGC-
GAAAATGCGCTGGTGGTGGCGCTCATCG-
CATCCACTCCCGCGCTGCGCACGCCCATGTTGT
GCTCGTGGGTAGTCTGGCCACTGCTGAC-
CTGCTGGCGGGCTGTGGCCTCATCCTA-
CACTTCGTGTTCCAGTAC GTGGTGCCCTCG-
GAGACTGTGAGCCTGCTCATGGTGGGCTTCCT
GGTGGCGTCCTTCGCCGCCTCAGTCAG-
CAGCCTGCTCGCTATCACAGTGGACCGT-
TACCTGTCCCTTTACAACGCGCTCAC-
CTACTACTCGCGCCGGACCCTGTTGGGCGTG
CACCTCTTGCTAGCAGCCACCTGGATCC
(SEQ.ID.NO.:8)

Rat GPR12 Probe:

AAGCTYAAAATGAACGAAGACCCGAAG-GTCAATTTAAGCGGGCTGCCTCGGGACT-GTATAGAAGCTGGTACTCCGGAGAACATCT CAGCCGCTGTCCCCTCCCAGGGCTCTGT-TGTGGAGTCAGAACCCGAGCTCG TTGTCAAC-CCCTGGGACATTGTCTTGTGCAGCTCAG-GAACCCTCATCTGCTGTGAAAATGCCGTCGTG GTCCTTATCATCTTCCACAGCCCCAGC-CTGCGAGCACCCATGTTCCTGCTGATAG-GCAGCCTGGCTCTTGCA GACCTGCTGGCTG-GTCTGGGACTCATCATCAATTTTGTTTTTGCCT ACCTGCTTCAGTCAGAAGCCACCAAGCTGGTC ACAATTGGACTCATTGTCGCCTCTTTC TCTGC-CTCTGTCTGCAGTTTGCTGGCTATCACTGT GGACCGCTACCTCTCGCTGTATTACGC-CCTGACGTACCACTCCGAGAGGACCGT-CACCTTTACCTATGTCATGCTAGTGAT-GCTCTGGGGATCC (SEQ.ID.NO.:9)

Example 2

Receptor Expression 1. cDNA and Vectors

With respect to GPR3 and GPR6, expression vectors comprising cDNA were generously supplied by Brian O'Dowd (University of Toronto). The vector for GPR3 cDNA was pcDNA3; the vector for GPR6 was pRcCMV (the coding region for GPR6 was subcloned into pCMV vector at a Hind III-XbaI site). GPR12 cDNA was prepared using the following protocol: Human GPR12 cDNA was obtained by PCR using human genomic DNA and a 5' primer from the 5' untranslated region with a Hind III restriction site, and a 3' primer from the 3' untranslated region containing a Bam HI site'. Primers had the following sequences:

5'-CTTAAGCTTGTGGCATTTGGTACT-3' (SEQ.ID.NO.: 10; 5' oligo)

5'-TCTGGATCCTTGGCCAGGCAGTGGAAGT-3 (SEQ.ID.NO.: 11; 3' oligo)

PCR was performed using rTth polymerase (Perkin Elmer) with the buffer system provided by the manufacturers, 0.25 $\mu$M of each primer, 0.2 $\mu$M of each of the four nucleotides and 0.2 $\mu$g of genomic DNA as template. The cycle condition was 30 cycles of 94° C. for 1 min, 57° C. for 1 min and 72° C. for 1.5 min. The 1.2 kb PCR fragment was digested with Hind III and Bam HI, and subcloned into Hind III-Bam HI site of pCMV expression vector. The resulting cDNA clones were fully sequenced and consistent with published sequences.

With respect to GPR21, PCR was performed using genomic DNA as template and rTth polymerase (Perkin Elmer) with the buffer system provided by the manufacturer, 0.25 $\mu$M of each primer, and 0.2 mM of each of the four nucleotides. The cycle condition was 30 cycles of 94° C. for 1 min, 62° C. for 1 min and 72° C. for 1 min and 20 sec. The 5' PCR primer was kinased with the sequence:

5'-GAGAATTCACTCCTGAGCTCAAGATGAACT-3' (SEQ.ID.NO.: 12)

and the 3' primer contained a BamHI site with the sequence:

5'-CGGGATCCCCGTAACTGAGCCACTTCAGAT-3' (SEQ.ID.NO.: 13).

The resulting 1.1 kb PCR fragment was digested with BamHI and cloned into EcoRV-BamHI site of pCMV expression vector. Nucleic acid (SEQ.ID.NO.: 14) and amino acid (SEQ.ID.NO.: 15) sequences for human GPR21 were thereafter determined.

With respect to AL022171, PCR was performed using genomic DNA as template and rTth polymerase (Perkin Elmer) with the buffer system provided by the manufacturer, 0.25 $\mu$M of each primer, and 0.2 mM of each of the four nucleotides. The cycle condition was 30 cycles of 94° C. for 1 min, 54° C. for 1 min and 72° C. for 1 min and 20 sec. The 5' primer contains an HindIII site with the following sequence:

5'-AGGAAGCTTTAAATTTCCAAGCCATGAATG-3' (SEQ.ID.NO.: 16)

and the 3' primer contained a EcoRI site with the following sequence:

5'-ACCGAATTCAGATTACATTTGATTTACTATG-3' (SEQ.ID.NO.: 17). The resulting 1.15 kb PCR fragment was digested with HindIII and EcoRI and cloned into HindIII-EcoRI site of pCMV expression vector. Nucleic acid (SEQ.ID.NO.: 18) and amino acid (SEQ.ID.NO.: 19) sequences for human AL022171 were thereafter determined and verified.

With respect to GPR4 (GenBank accession number L36148 (SEQ.ID.NO.:60), expression vectors comprising the cDNA were generously provided by Brian O'Dowd (University of Toronto). The vector for GPR4 cDNA was pcDNA3 and this was subcloned into pCMV vector at a HindIII-XbaI site (the 5' untranslated region between HindIII and an ApaI site was trimmed by conducting digestion/self ligation.)

With respect to RE2 (GenBank accession number AF091890), PCR was performed using human brain cDNA as template and rTth polymerase (Perkin Elmer) with the buffer system provided by the manufacturer, 0.25 $\mu$M of each primer, and 0.2 mM of each of the four nucleotides. The cycle condition was 30 cycles of 94° C. for 1 min, 62° C. for 1 min and 72° C. for 1 min and 30 sec. The 5' PCR primer contained an EcoRI site with the sequence5'-AGCGAATTCTGCCCACCCCACGCCGAGGTGCT-3' (SEQ. ID. No. 20) and the 3' primer contained a BamHI site with the sequence 5'-TGCGGATCCGCCAGCTCTTGAGCCTGCACA-3' (SEQ.ID.NO.: 21). The 1.36 kb PCR fragment that resulted after two rounds of PCR was then digested with EcoRI and BamHI and cloned into EcoRI-BamHI site of pCMV. Nucleic acid (SEQ. ID. NO. 22) and amino acid sequence (SEQ. ID. NO. 23) was thereafter determined.

With respect to OGR1 (GenBank accession number U48405), PCR was performed using human genomic DNA as template and rTth polymerase (Perkin Elmer) with the buffer system provided by the manufacturer, 0.25 ΞM of each primer, and 0.2 mM of each of the four nucleotides. The cycle condition was 30 cycles of 94° C. for 1 min, 62° C. for 1 min and 72° C. for 1 min and 20 sec. The 5' PCR primer contained a HindIII site with the sequence 5'-GGAAGCTTCAGGCCCAAAGATGGGGAACAT-3' (SEQ. ID. No. 24) and the 3' primer contain a BamHI site with the sequence 5'-GTGGATCCACCCGCGGAGGACCCAGGCTAG-3' (SEQ. ID. NO.25). The resulting 1.14 kb PCR fragment was digested with HindIII and BamHI and cloned into HindIII-BamHI site pCMV. Nucleic acid (SEQ. ID. NO. 26) and amino acid sequence (SEQ. ID. NO. 27) was thereafter determined.

With respect to GHSR, PCR was performed using hippocampus cDNA as template and TaqPlus Precision polymerase (Stratagene) with the buffer system provided by the manufacturer, 0.25 $\mu$M of each primer, and 0.2 mM of each 4 nucleotides. The cycle condition was 30 cycles of 94° C.

for 1 min, 68° C. for 1 min and 72° C. for 1 min and 10 sec. For first round PCR, the 5' PCR primer sequence:

5'-ATGTGGAACGCGACGCCCAGCG-3' (SEQ.ID.NO.40)

and the 3' primer sequence:

5'-TCATGTATTAATACTAGATTCT-3' (SEQ.ID.NO.41).

Two microliters of the first round PCR was used as a template for the second round PCR where the 5' primer was kinased with sequence:

5'-TACCATGTGGAACGCGACGCCCAGCGAAGAG CCGGGGT-3' (SEQ.ID.NO.:42) and the 3' primer contains an EcoRI site with the sequence:

5'-CGGAATTCATGTATTAATACTAGATTCTGTCCA GGCCCG-3' (SEQ.ID.NO.:43). The 1.1 kb PCR fragment was digested with EcoRI and cloned into blunt-EcoRI site of CMVp expression vector. Nucleic acid (SEQ. ID. NO.:44) and amino acid (SEQ.ID.NO.:45) sequences for human GHSR were thereafter determined.

2. Transfection Procedure

On day one, $1\times10^7$ 293 or 293T cells per 150 mm plate were plated out. On day two, two reaction tubes were prepared (the proportions to follow for each tube are per plate): tube A was prepared by mixing between 8–20 $\mu$g DNA (e.g., pCMV vector; pCMV vector with receptor cDNA; pCMV with GPCR Fusion Protein, supra) in 1–2 ml serum free DMEM (Irvine Scientific, Irvine, Calif.); tube B was prepared by mixing 50–120 $\mu$l lipofectamine (Gibco BRL) in 1–2 ml serum free DMEM. Tubes A and B were then admixed by inversions (several times), followed by incubation at room temperature for 30–45 min. The admixture is referred to as the "transfection mixture". Plated cells were washed with 1×PBS, followed by addition of 10×12 ml serum free DMEM. 2.4 ml of the transfection mixture was then added to the cells, followed by incubation for 4 hrs. at 37° C./5% $CO_2$. The transfection mixture was then removed by aspiration, followed by the addition of 25 ml of DMEM/10% Fetal Bovine Serum. Cells were then incubated at 37° C./5% $CO_2$.

For GPCR Fusion Protein, preferred amounts to the above are as follows: 12 $\mu$g DNA; 2 ml serum free DMEM; 60 $\mu$l lipofectamine; 293 cells 9 and an addition of 12 ml serum free DMEM).

Example 3

Tissue Distribution of GPCR

For some orphan receptors, it will be apparent to those in the art that there is an understanding of the distribution of such receptors within, e.g., a human, or associated with a disease state. However, for many orphan receptors, such information is not known, or will not be known. It is therefore preferred that some understanding of where such receptors may be distributed be understood; this allows for the ability to gain a predictive opportunity to associate a particular receptor with a disease state or disorder associated with the particular tissue where the receptor may be preferentially expressed. Using a commercially available mRNA dot-blot format, the distribution of endogenous, constitutively active GPCRs in various tissue types was assessed.

Figure 3:
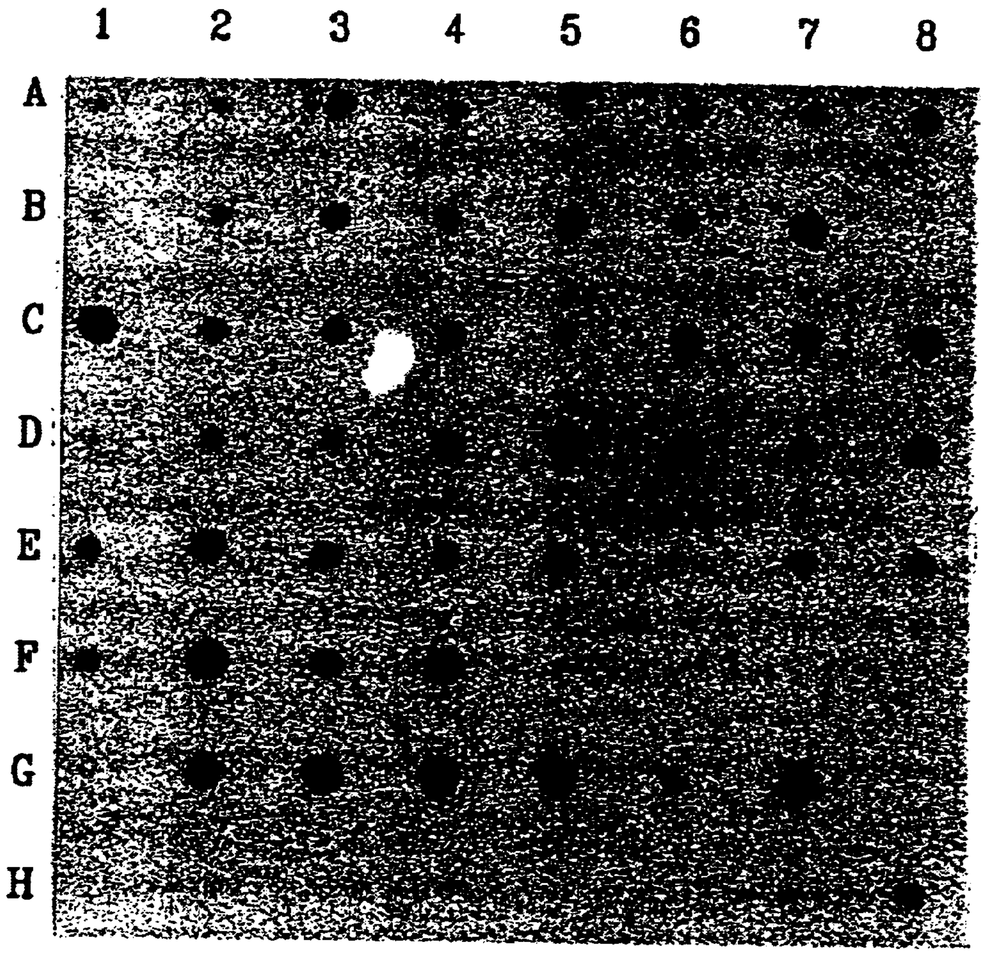
FIG. 3 is computerized representation of a "dot-blot" showing the distribution of the orphan receptor GPR4 across a variety of human tissues (see Appendix A for grid-code).

Preferably, the entire coding region of the receptor is used to generate a radiolabeled probe using a Prime-It II™ Random Primer Labeling Kit (Stratagene, #300385), according to the manufacturer's instructions. As an example, this approach was utilized for GPR4. Human RNA Master Blot™ kit (Clontech, #7770-1) was hybridized with this probe and washed under stringent conditions, in accordance with manufacturer instructions. The blot was exposed to Kodak BioMax™ Autoradiography film overnight, at −80° C. Results are presented in FIG. 3. Based upon these results, it is noted that GPR4 appears to be expressed throughout a variety of fetal tissue types (row G), as well as non-fetal heart (C1), and non-fetal lung (F1). This approach can be readily utilized for other receptors.

Example 4

GTP Membrane Binding Scintillation Proximity Assay

When a G protein-coupled receptor is in its active state, either as a result of ligand binding or constitutive activation, the receptor binds to a G protein (in the case of GPR3, GPR4, GPR6, GPR12, GPR21, GHSR, OGR1, RE2 and AL022171, Gs) and stimulates the binding of GTP to the G protein. The trimeric G protein-receptor complex acts as a GTPase and slowly hydrolyzes the GTP to GDP, at which point the receptor normally is deactivated. Constitutively activated receptors continue to exchange GDP for GTP. The non-hydrolyzable GTP analog, $[^{35}S]GTP\gamma S$, can be utilized to demonstrate enhanced binding of $[^{35}S]GTP\gamma S$ to membranes expressing constitutively activated receptors. The advantage of using $[^{35}S]GTP\gamma S$ binding to measure constitutive activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate $[^{35}S]GTP\gamma S$ binding to membranes expressing the relevant receptors. The assay can, therefore, be used in the direct identification method to screen candidate compounds to known, orphan and constitutively activated G protein coupled receptors. The assay is generic and has application to drug discovery at all G protein coupled receptors.

The $[^{35}S]GTP\gamma S$ assay was incubated in 20 mM HEPES, pH 7.4, binding buffer with 12 nM $[^{35}S]GTP\gamma S$ and 75 $\mu$g membrane protein [e.g., 293T cells expressing GPR3] and 1 $\mu$M GDP for 1 hour. Wheatgerm agglutinin beads (25 $\mu$l; Amersham) were then added and the mixture was incubated for another 30 minutes at room temperature. The tubes were then centrifuged at 1500×g for 5 minutes at room temperature and then counted in a scintillation counter.

Figure 4:
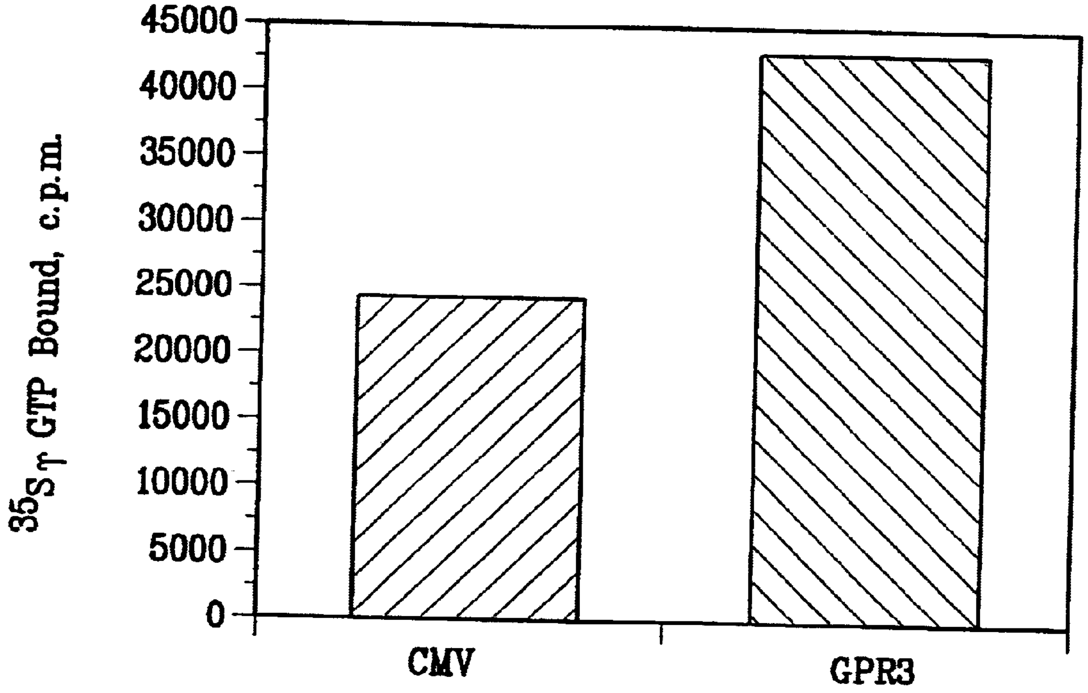
FIG. 4 is a diagram showing enhanced binding of [$^{35}$S]GTPγS to membranes prepared from 293T cells transfected with the orphan receptor GPR3 compared to those transfected with control vector alone at 75 μg/well membrane protein. The radiolabeled concentration of [$^{35}$S]GTPγS was held constant at 1.2 nM and the GDP concentration was held constant at 1 μM. The assay was performed on 96-well format in Wallac scintistrips.

Referring to FIG. 4, GPR3 receptor was determined to have increased activity as compared to control; this heightened activity is not the result of autocrine stimulation in that the data were obtained from membrane preparations, as opposed to whole cell preparations.

Example 5

Receptor Homology Determination

Following confirmation that GPR3 is a constitutively activated receptor, a homology search of the available G protein-coupled data banks (GeneBank), using the commercially available program, DNA Star, identified two highly homologous receptors, GPR6 and GPR12 (see FIG. 5A); both of these receptors are orphan receptors. While the sequence of these receptors was previously "known" (i.e., they were available on the databases), it was not known that these two receptors are constitutively activated in their endogenous forms (see Example 6, FIG. 7). Furthermore, heretofore there would be no reason to search for such receptors for use in a drug discovery program in that the ligands therefore are not known or have not been identified. As such, the dogma approach to drug discovery would at best find the homology between GPR3, GPR6 and GPR12 of minor interest or, more likely, irrelevant.

Example 6

Analysis of Homologous Receptors For Constitutive Activation

Although a variety of cells are available to the art for the expression of proteins, it is most preferred that mammalian cells be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells. Of the mammalian cells, COS-7,293 and 293T cells are particularly preferred, although the specific mammalian cell utilized can be predicated upon the particular needs of the artisan.

1. Analysis of GPR3, GPR6 and GPR12

To generate a β-galactosidase reporter containing multiple Gal4 binding sites, a Bgl II/HindIII fragment was removed from the somatostatin promoter-containing plasmid 1.4(5× Gal)CAT (Leonard, J. et al (1992) *PNAS USA* 89:6247–6251) and cloned into p β gal-Basic (Promega). The Bgl II/HindIII fragment contains a variant of the minimal somatostatin promoter (from −71 bp to +50 bp relative to the transcription start site) in which the core 4 bp of the cAMP Response Element (−46 to −43) were replaced with 5 copies of the recognition sequence for the yeast transcription factor Gal4. When this reporter is co-transfected with an expression plasmid encoding a Gal4-CREB fusion protein, it is highly responsive to agents that increase the cAMP signaling pathway.

VIP2.0Zc is a cell line that has been stably transfected with the reporter gene β-galactosidase under the control of a cAMP responsive VIP promoter (Konig et al. Mol. Cell-.Neuro. 1991, 2, 331–337). The cell line was used here to indirectly measure the accumulation of intracellular cAMP. Approximately 2 million cells were plated in 6 cm plate the day before transfection. DNA (5 μg), for each receptor, was mixed with 2.5 ml serum-free DMEM containing 200 μg/ml DEAE dextran and 100 μM chloroquine, and added to a rinsed cell monolayer. After incubation for 90 min in a $CO_2$ incubator, the transfection medium was removed. The cells were washed with serum-free medium and supplemented with fresh complete medium. Twenty four hours after transfection, the cells were replated into 96-well plate at a density of 50–100 K per well and the β-galactosidase activity was assayed 48 to 72 hours after transfection.

The assay buffer contained 100 mM sodium phosphate, 2 mM $MgSO_4$, 0.1 mM $MnCl_2$, pH 8.0. The cells were washed with PBS, and 25 μl/well of hypotonic lysis buffer consisting of 0.1× assay buffer was added. Ten minutes later, 100 μl of assay buffer containing 0.5% Triton X-100 and 40 mM β-mercaptoethanol was added to each well and incubation at room temperature continued for 10 minutes. The substrate solution containing 5 mg/ml chlorophenol red-β-D-galactopyranoside (CPRG) in assay buffer was added at 25 μl/well and the plate was incubated at 37° C. for 30 minutes before absorbance at 595 nm was measured with a plate reader.

Figure 6A:
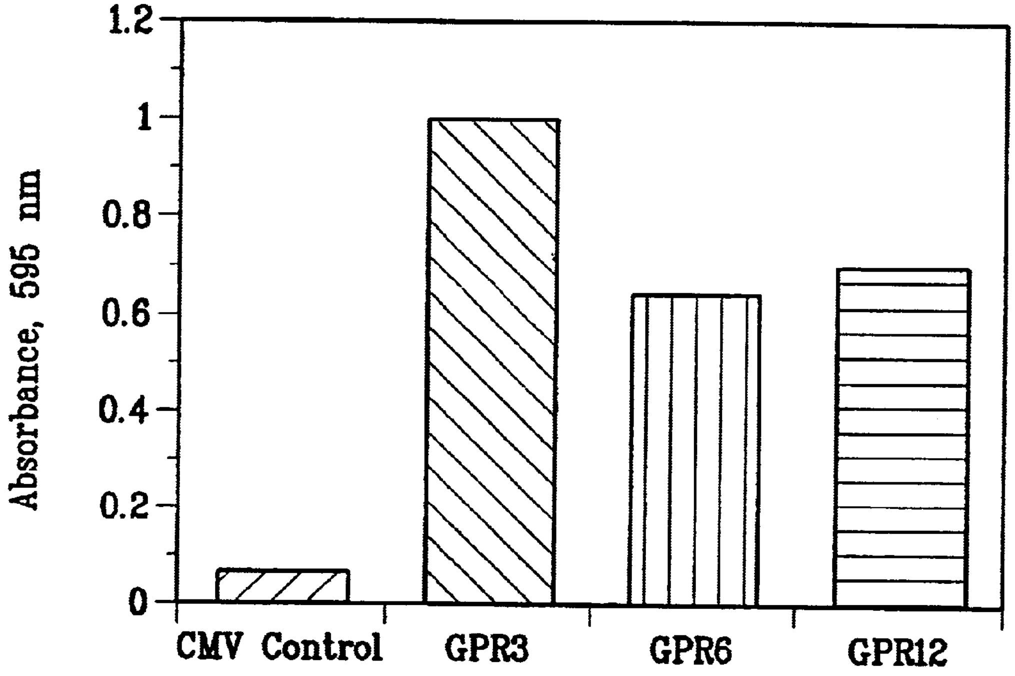
FIG. 6A is a diagram showing that the orphan receptors GPR3, GPR6, and GPR12 are confirmed to be constitutively active by their enhanced ability to induce expression of β-galactosidase from a CRE driven reporter system in VIP cells.

GPR3, GPR6 and GPR12 were assayed using the foregoing system, and it was determined that both GPR6 and GPR12 are constitutively active. See FIG. 6A.

2. Analysis of GPR21 and AL022171

Figure 6B:
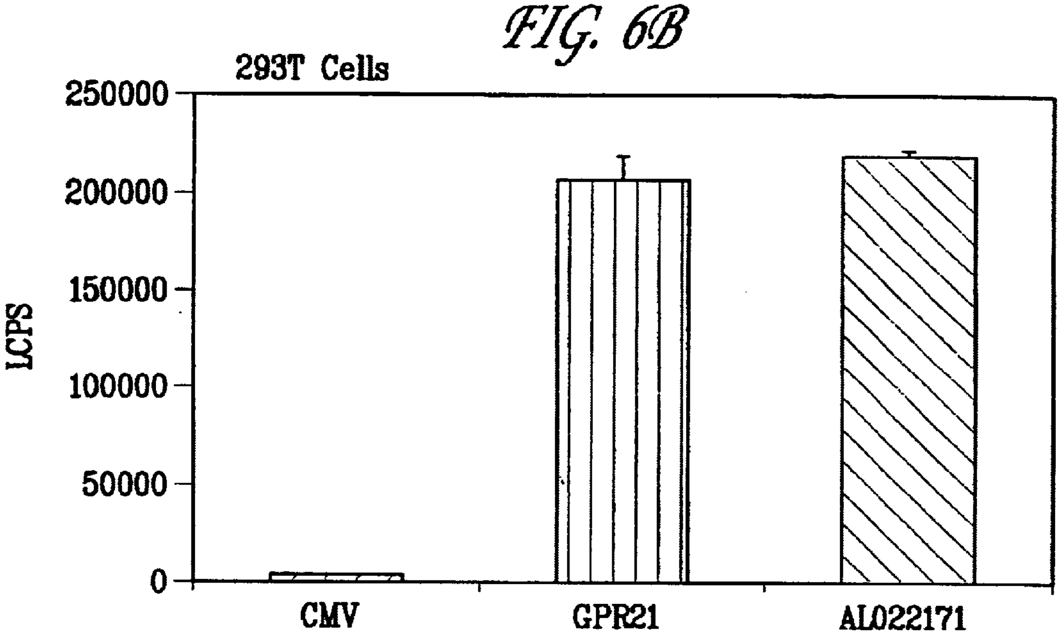
FIGS. 6B and 6C are diagrams of orphan receptors GPR21 and AL022171, respectively, that have also been confirmed to be constitutively active by their enhanced ability to induce expression of the luciferase gene from a CRE driven reporter system in both 293 and 293T cells.
Figure 6C:
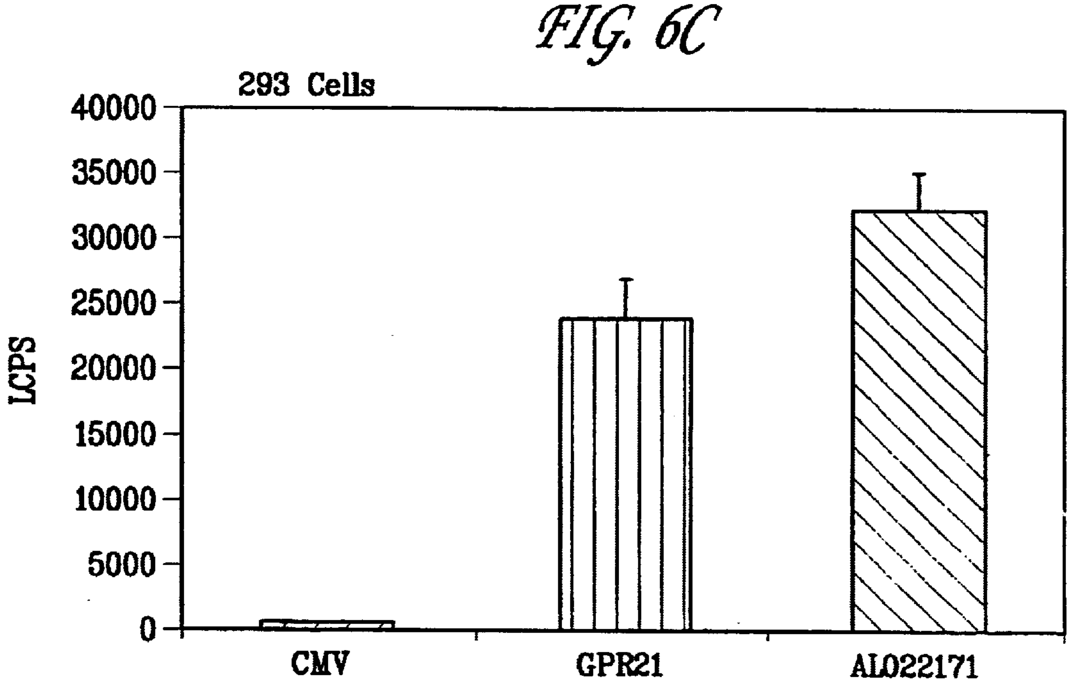

293 and 293T cells were plated-out on 96 well plates at a density of $2\times10^4$ cells per well and were transfected, using Lipofectamine Reagent (BRL), the following day according to manufacturer instructions. A DNA/lipid mixture was prepared for each 6-well transfection as follows: 260 ng of plasmid DNA in 100 μl of DMEM were gently mixed with 2 μl of lipid in 100 μl of DMEM (the 260 ng of plasmid DNA consisted of 200 ng of a 8×CRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 (see 7 *Human Gene Therapy* 1883 (1996)) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture was diluted with 400 μl of DMEM and 100 μl of the diluted mixture was added to each well. 100 μl of DMEM with 10% FCS were added to each well after a 4 hr incubation in a cell culture incubator. The following day the transfected cells were changed with 200 μl/well of DMEM with 10% FCS. Eight (8) hours later, the wells were changed to 100 μl/well of DMEM without phenol red, after one wash with PBS. Luciferase activity were measured the next day using the LucLite™ reporter gene assay kit (Packard) following manufacturer instructions and read on a 1450 MicroBeta™ scintillation and luminescence counter (Wallac). Results are summarized in FIGS. 6B and 6C.

GPR21 and AL022171 were assayed using the foregoing system, and based upon these results, it was determined that both GPR21 and AL022171 are constitutively active in their endogenous forms. See FIGS. 6B and 6C.

3. Analysis of GPR4, RE2, OGR1 and GHSR

Using the protocols defined herein, GPR4, RE2, OGR1 and GHSR were analyzed and determined to be constitutively active in their endogenous forms (data not shown).

Example 7

Tissue Distribution of GPR3, GPR6 and GPR12

Tissue samples were examined for expression of these orphan receptors by comparative RT-PCR, using the following primers:

GPR3:

5'-CTGGTCCTGCACTTTGCTGC-3' (SEQ.ID.NO.: 28)

5'-AGCATCACATAGGTCCGTGTCAC-3' (SEQ.ID.NO.: 29)

These primers amplify a 194 bp fragment.

GPR6:

5'-ACCAGAAAGGGTGTGGGTACACTG-3' (SEQ. ID. NO.: 30)

5'-GGAACGAAAGGGCACTTTGG-3' (SEQ. ID. NO.: 31)

These primers amplify a 249 bp fragment.

GPR12:

5'-GCTGCCTCGGGATTATTTAG-3' (SEQ. ID. NO.: 32)

5'-GCCTATTAGCAGGAACATGGGTG-3' (SEQ. ID. NO.: 33)

These primers amplify a 220 bp fragment.

These amplicons were designed to be non-overlapping, i.e., there is no sequence similarity between them, and to have similar Tm's, such that each primer pair amplifies its respective target at the same optimal annealing temperature. This diminishes the chance that an amplicon from one primer pair will act as an annealing target for the other primers in the multiplex reaction, therefore reducing the chance of interference with other primer pairs.

Total RNA was extracted from tissue samples (human) using TRIzol™ Reagent (Gibco/BRL), following manufacturer instructions. cDNA was generated using 2 mg total RNA and a First-Strand™ cDNA synthesis kit (Pharmacia). The cDNA samples were then diluted 1:3 in $H_2O$ and comparative PCR was performed as described (Jensen, J. et al. (1996) *J. Biol. Chem.* 271:187490) in the presence of [$^{32}$P]dCTP. All reactions included the SP1-specific primers, which amplify a 300 bp fragment, to serve as an internal control. Using the primers outlined above, under defined PCR conditions (1 cycle: 95° C., 5 min; 23 cycles: 95° C., 30 sec, 58° C., 30 sec, 72° C., 1 min; 1 cycle: 72° C., 10 min) gave consistently reliable and quantitatively accurate results. It was further determined that the selected primer pairs did not interfere with each other when multiplexed. PCR products were visualized by denaturing gel electrophoresis (7M urea, 5% polyacrylamide (Long Ranger™ Solution, AT Biochemical, 0.6×TBE) and subsequent autoradiography.

Figures 7A, 7B, 7C:
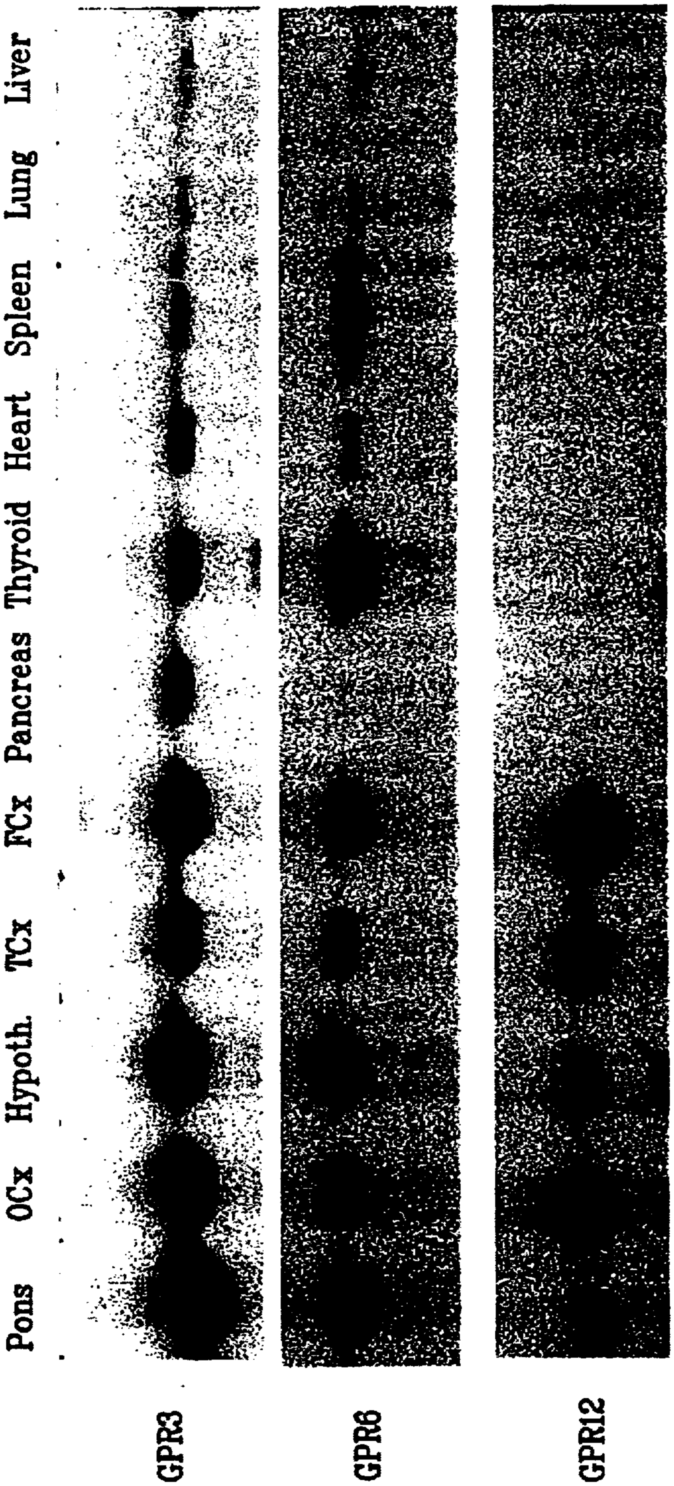
FIGS. 7A, 7B and 7C show the relative distribution of the expression of the GPR3 (A), GPR6 (B), and GPR12 (C) orphan receptors across several normal human tissues as determined by RT-PCR. Abbreviations: Ocx=occipital cortex; Hypoth=hypothalamus; Tex=temporal cortex; Fcx=frontal cortex.
Figure 8:
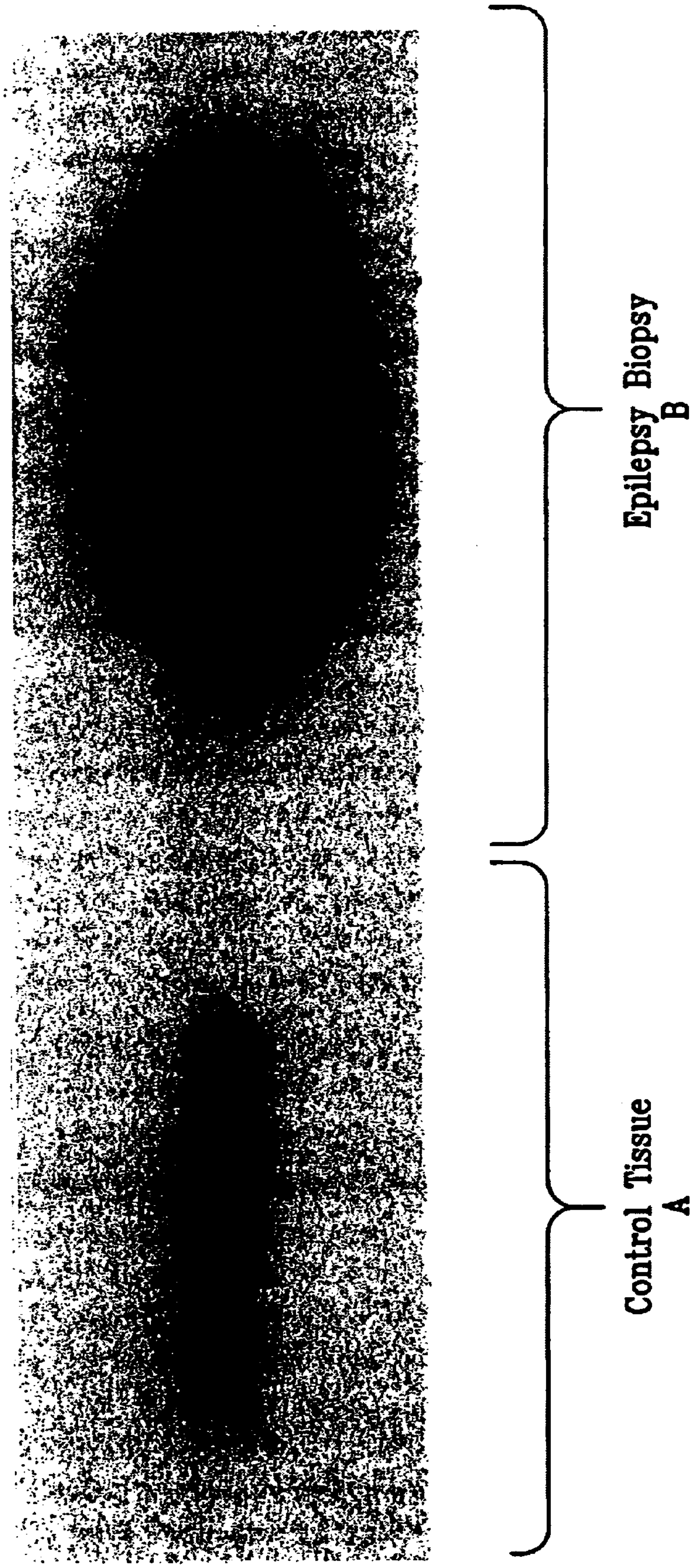
FIGS. 8A and 8B show GPR3 receptor expression in normal (A) and epileptic (B) human brain tissue as examined by RT-PCR.

FIGS. 7A, 7B, and 7C show the distribution of GPR3, GPR6 and GPR12 across human tissues. This information allows for assessing disease states that are associated with such tissue, as well as determining specific regions within such tissue where such expression predominates, thus allowing for correlating such receptor expression with particular disease states. This, in turn, then allows for direct identification of compounds that impact such receptors, without the need to understand or know the endogenous ligand for such receptor. Further screening reveals that GPR3 is expressed in much higher levels in human epilepsy tissue samples (tissue source: temporal cortex), as compared with controls, as evidenced by RT-PCR analysis (FIG. 8).

Example 8A

Functional Analysis—GPR6 (In Situ Analysis)

The distribution of GPR6 in the hypothalamus suggested possible involvement in feeding behavior. Accordingly, a functional analysis of this receptor was undertaken. In situ analysis was conducted as follows:

1. Probe Design

GPR6 probe was produced from a 450 bp HindIII-ScaI fragment of the GPR6 receptor cloned into the HindIII-SmaI site of pBluescriptSK+. Riboprobes were produced using a T7 transcription system in a standard labeling reaction consisting of: 1 μg of linearized plasmid, 2 μl of 5× transcription buffer, 125 μCi of $^{35}$S-UTP, 150 μM of GTP, CTP and ATP, 12.5 mM dithiothreitol, 20 U of RNase inhibitor and 6 U of appropriate polymerase. The reaction was incubated at 37° C. for 90 min., labeled probe being separated from free nucleotides over Sephadex G-50 spin columns.

2. Tissue preparation

Dissected tissue was frozen in isopentane cooled to −42° C. and subsequently stored at −80° C. prior to sectioning on a cryostat maintained at −20° C. Slide-mounted tissue sections were then stored at −80° C.

3. In Situ Hybridization Protocol

Tissue sections were removed from the −80° C. freezer and incubated with a 1 μg/ml solution of proteinase-K to permeabilize the tissue and inactivate endogenous RNase. After this treatment, sections were incubated in succession in water (1 min), 0.1 M triethanolamine (pH 8.0; 1 min), and 0.25% acetic anhydride in 0.1 M triethanolamine (10 min). The tissue was then washed in 2×SSC (0.3 mM NaCl, 0.03 nM Na citrate, pH 7.2; 5 min) and dehydrated through graded concentrations of ethanol. Sections were then hybridized with $1.5\times10^6$ dpm of [$^{35}$S]UTP-labeled cRNA probes in 20 μl of a hybridization buffer containing 75% formamide, 10% dextran sulfate, 3×SSC, 50 mM sodium phosphate buffer (pH 7.4), 1×Denhart's solution, 0.1 mg/ml yeast tRNA, and 0.1 mg/ml sheared salmon sperm DNA. Tissue sections were covered with coverslips that were sealed with rubber cement. The slides were incubated overnight at 50° C. On the following day, the rubber cement was removed, the coverslips were soaked-off with 2×SSC, and the tissue sections were washed for 10 min in fresh 2×SSC solution. Single stranded probe not hybridized with endogenous mRNAs was removed by incubating the sections for 30 min in 200 μg/ml solution of RNase-A at 37° C. The tissue was then washed in increasingly stringent SSC solutions (2, 1 and 0.5×SSC; 10 min each), followed by a 1 hr wash in 0.5×SSC at 60° C. After this final wash, the tissue sections were dehydrated using graded concentrations of ethanol, air dried and prepared for detection by x-ray autoradiography on Kodak XAR-5 film.

4. Analysis

Figure 9:
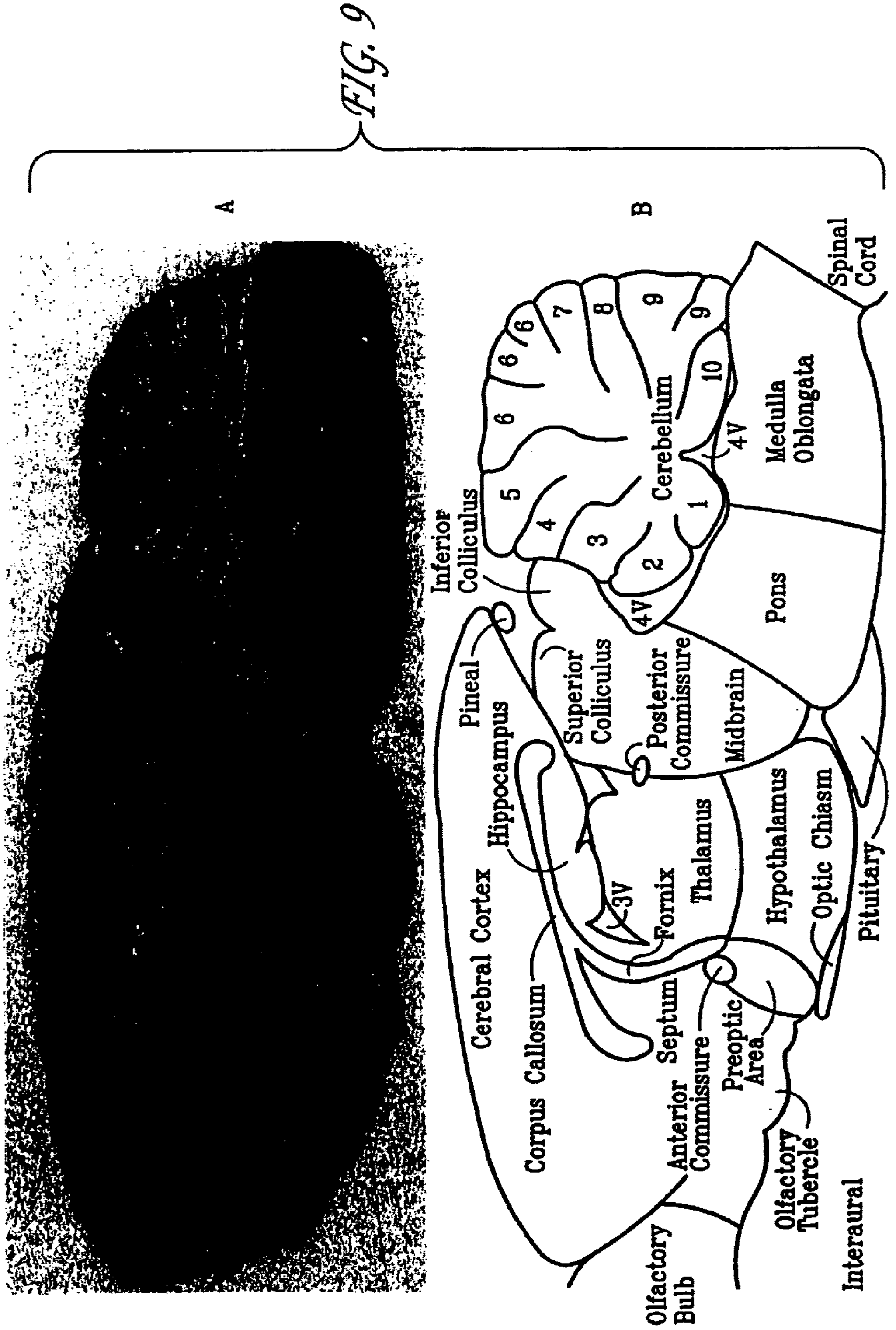
FIG. 9A is a copy of an autoradiograph evidencing the results from in situ hybridization (normal rat) using GPR6 probe.
FIG. 9B is a reference map of the corresponding region of the rat brain.

Utilizing the above protocol on normal male rats (Sprague-Dawley, Charles River), it was determined that GPR6 is expressed in the following areas of the brain: hypothalamus, hippocampus, nucleus accumbens, caudate and cerebral cortex. See FIG. 9A for a representative tissue section (GPR6 receptor is presented in the dark areas; FIG. 9B provides a reference map of the rat brain.)

Figure 10:
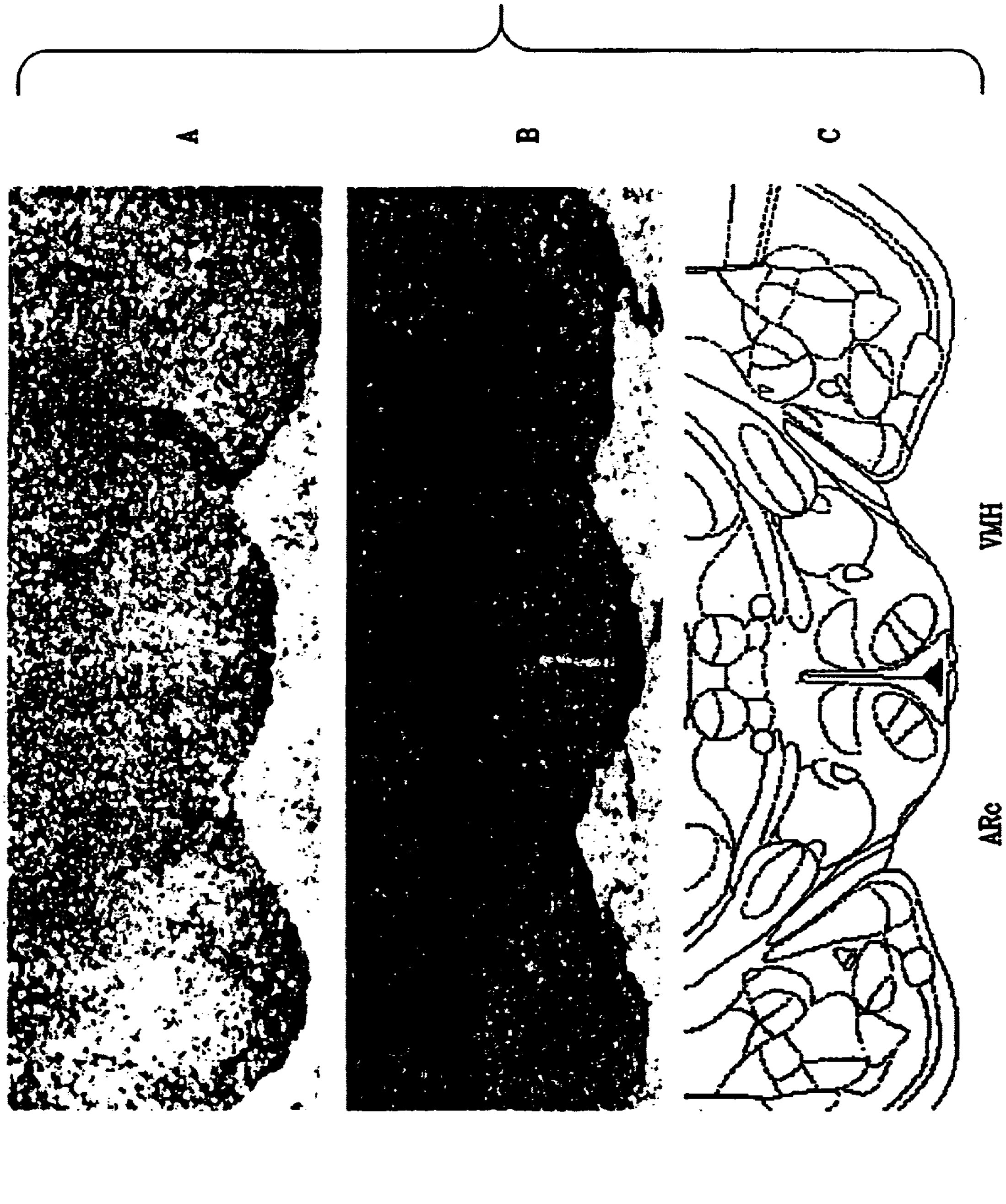
FIG. 10A is a copy of an autoradiograph evidencing the results from in situ hybridization (Zucker rat—lean) using GPR6 probe.
FIG. 10B is a copy of an autoradiograph evidencing the results from in situ hybridization (Zucker rat—obese) using GPR6 probe.
FIG. 10C is a reference map of the corresponding region of the rat brain.
Figure 11B:
FIGS. 11A–F are copies of autoradiographs evidencing the results from in situ hybridization (normal rat) using GPR12 probe.
Figure 11A:
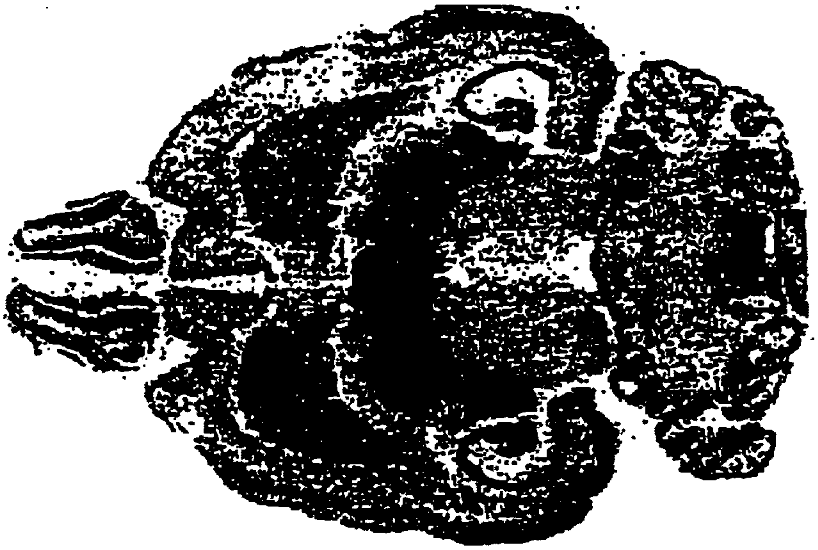
Figure 11D:
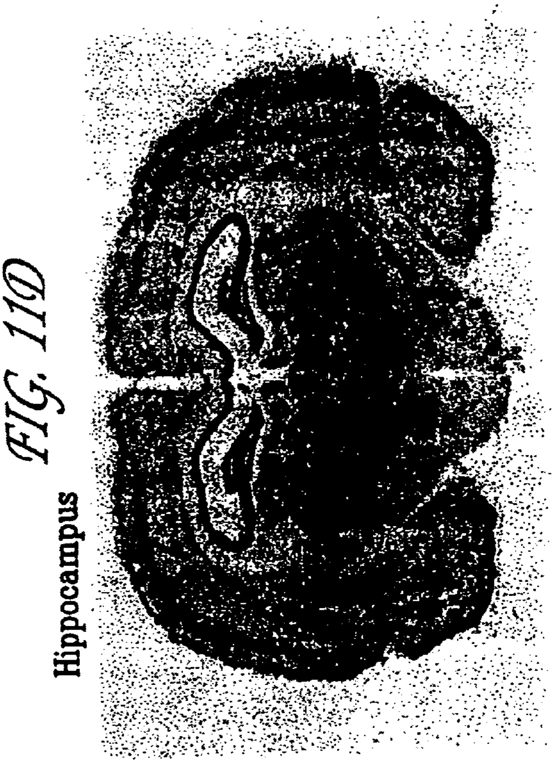
Figure 11C:
Figure 11E:
Figure 11F:

Given the high levels of expression of GPR6 in areas of the brain associated with feeding, an in situ analysis was conducted using the above protocol on both lean and obese male Zucker rats (Charles River). As those in the art appreciate, the Zucker animals are genetically bred to result in animals that exhibit a lean or obese phenotype. FIG. 10A provides a representative tissue section of GPR6 receptor expression in the lean Zucker animals; FIG. 10B provides a representative tissue section of GPR6 receptor expression in the obese Zucker animals; FIG. 10C is a reference map of this section of the rat brain. These results support the position that the endogenous, constitutively activated orphan receptor GPR6 is relatively overexpressed in a model of obesity.

Example 8B

Functional Analysis—GPR12 (In Situ Analysis)

In situ analysis for the GPR12 receptor was conducted as follows:

1. Probe Design

GPR12 probe was produced from a 515 bp (NT5–NT520) HindIII-BamHI fragment of the rat GPR12 receptor cloned into the HindIII-BamHI site of pBluescriptSK+. Riboprobes were produced using a T3/T7 transcription system in a standard labeling reaction consisting of: 1 μg of linearized plasmid, 2 μl of 5× transcription buffer, 125 μCi of $^{35}$S-UTP, 150 μM of GTP, CTP and ATP, 12.5 mM dithiothreitol, 20

U of Rnase inhibitor and 6 U of appropriate polymerase. The reaction was incubated at 37° C. for 90 min., labeled probe being separated from free nucleotides over Sephadex G-50 spin columns.

2. Tissue preparation

Dissected tissue was frozen in isopentane cooled to −42° C. and subsequently stored at −80° C. prior to sectioning on a cryostat maintained at −20° C. Slide-mounted tissue sections were then stored at −80° C.

3. In Situ Hybridization Protocol

Tissue sections were removed from the −80° C. freezer and incubated with a 1 $\mu$g/ml solution of proteinase-K to permeabilize the tissue and inactivate endogenous RNase. After this treatment, sections are incubated in succession in water (1 min), 0.1 M triethanolamine (pH 8.0; 1 min), and 0.25% acetic anhydride in 0.1 M triethanolamine (10 min). The tissue was then washed in 2×SSC (0.3 mM NaCl, 0.03 nM Na citrate, pH 7.2; 5 min) and dehydrated through graded concentrations of ethanol. Sections were then hybridized with $1.5\times10^6$ dpm of [$^{35}$S]UTP-labeled cRNA probes in 20 $\mu$l of a hybridization buffer containing 75% formamide, 10% dextran sulfate, 3×SSC, 50 mM sodium phosphate buffer (pH 7.4), 1×Denhart's solution, 0.1 mg/ml yeast tRNA, and 0.1 mg/ml sheared salmon sperm DNA. Tissue sections were covered with coverslips that were sealed with rubber cement. The slides were incubated overnight at 50° C. On the following day, the rubber cement was removed, the coverslips were soaked-off with 2×SSC, and the tissue sections were washed for 10 min in fresh 2×SSC solution. Single stranded probe not hybridized with endogenous mRNAs was removed by incubating the sections for 30 min in 200 $\mu$g/ml solution of RNase-A at 37° C. The tissue was then washed in increasingly stringent SSC solutions (2, 1 and 0.5×SSC; 10 min each), followed by a 1 hr wash in 0.5×SSC at 60° C. After this final wash, the tissue sections were dehydrated using graded concentrations of ethanol, air dried and prepared for detection by x-ray autoradiography on Kodak XAR-5 film.

4. Analysis

Utilizing the above protocol on normal male rats (Sprague-Dawley, Charles River), it was determined that GPR12 is expressed in the following areas of the brain: hippocampus (particularly in regions $CA_3$, $CA_4$ and the dentate gyrus; outer layers of the cerebral cortex; and the amygdala—all of these regions are well known in the art as associated with regions important for learning and memory); and thalamic relay nuclei, including the lateral geniculate nucleus, the medial geniculate nucleus and the lateral thelamic nucleus (regions related to lateral relay functions, e.g., vision and hearing). See FIGS. 11A–F for representative tissue sections (GPR12 receptor is presented in the dark areas).

Example 8C

Functional Analysis—Co-Localization of GPR6 With Feeding-Behavior Receptors (In Situ Analysis)

The human orexin receptor $OX_1R$, previously an orphan GPCR (a.k.a., "HFGAN72"), has been localized in the lateral hypothalamic region of the brain and has been hypothesized to be involved in regulation of feeding behavior. Sakurai, T. et al 92(4) Cell 573 (1998). As noted in Sakurai, "pharmacological intervention directed at the orexin receptors may prove to be an attractive avenue toward the discovery of novel therapeutics for diseases involving disregulation of energy homeostasis, such as obesity and diabetes mellitus." Id at 582. The melanocortin-3 receptor (MC-3) has also been identified, Gantz, I. Et al, 268(11) J. Biol. Chem. 8246 (1993), and is similarly associated with energy homeostasis.

An understanding of the neural pathways involved in the regulation and disregulation of energy homeostasis is important for appreciation of hierarchical nuances that are critical for rational drug design. Merely affecting one receptor, particularly a receptor that is "downstream" of a more relevant receptor-pathway, may lead to a substantial expenditure of time and resources that ultimately results in the development of a pharmaceutical compound that may have little, if any, substantive impact on a particular disease state. For example, leptin, while clearly involved in some fashion with energy homeostasis, has not, to date, evidenced an opportunity for the development of a pharmaceutical product in the area of obesity. And while both the $OX_1$ and MC-3 receptors (as well as other melanocortin receptors) are also, in some manner, involved with energy homeostasis, development of pharmaceuticals based upon the traditional receptor "antagonist" approach may prove to be more frustrating than fruitful if, for example, these receptors are not constitutively active in their endogenous forms, and, within the energy homeostasis pathway, there is a receptor that is constitutively active in its endogenous state. Indeed, the endogenous, constitutively active receptor would, by definition, continually signal whereas the endogenous, non-constitutively active receptors would require ligand-binding for such signaling. Thus, in the case of GPR6, which is not only constitutively active in its endogenous form, but also appears to be significantly up-regulated in an animal model of obesity, GPR6 would, in essence, "trump" other energy homeostasis related receptors in that even with complete blockage via receptor antagonists to these receptors, GPR6 would continue signaling. Thus, a determination of whether these receptors (and others within the energy homeostasis pathway) are co-localized within discrete, neuronal regions, is useful in providing a more refined receptor target for drug development.

In situ hybridization studies were performed as described above for GPR6, $OX_1R$ and MC-3 receptors. For GPR6, the in situ probe utilized was as set forth in Example 7A. For $OX_1R$ and MC-3, the probes were based upon the published rat sequences and were approximately 950 bp and 441 bp, respectively. Tissue preparation (normal rats) and in situ hybridization were substantially the same as set forth in Example 8A.

Figure 12:
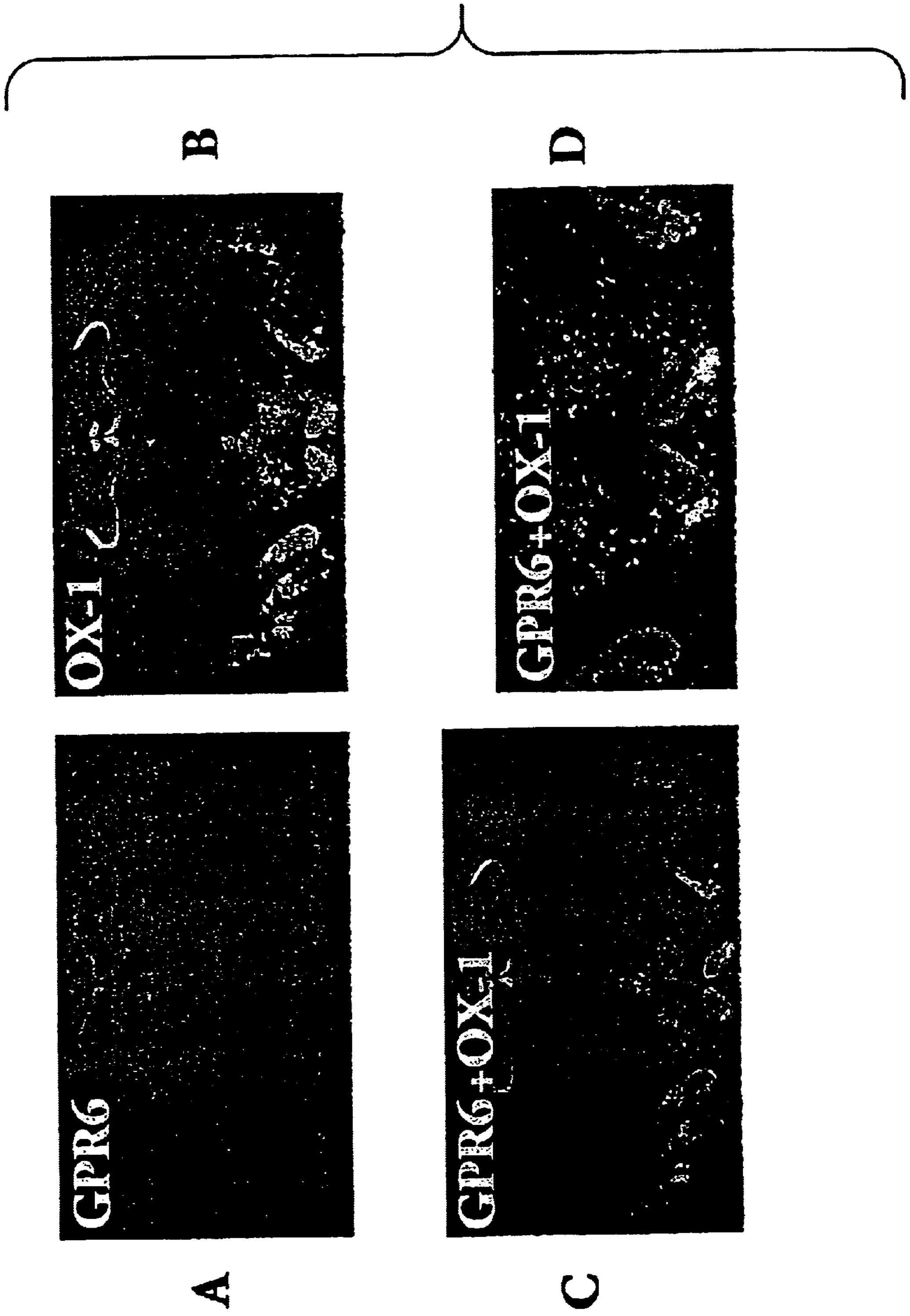
FIGS. 12A–D are copies of autoradiographs evidencing the results from in situ hybridization (normal rat) using GPR6 probe (12A), and orexin 1 receptor probe (12B) with overlays for determination of co-localization of the two receptors (12C and 12D).
Figure 13:
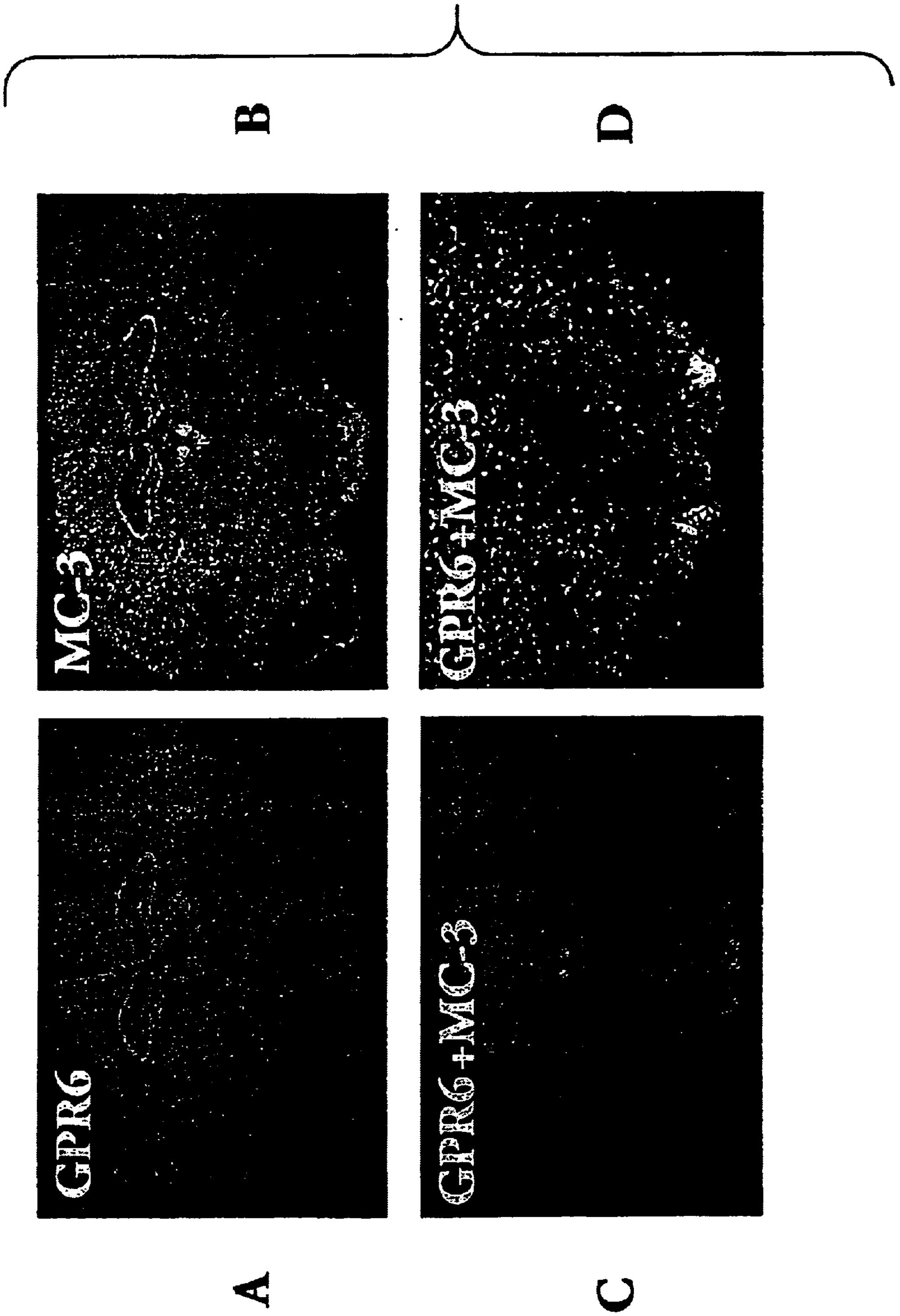
FIGS. 13 A–D are copies of autoradiographs evidencing the results from in situ hybridization (normal rat) using GPR6 probe (13A), and melanocortin-3 receptor probe (13B) with overlays for determination of co-localization of the two receptors (13C and 13D).

Results are presented in FIG. 12 (GPR6 and $OX_1R$) and FIG. 13 (GPR6 and MC-3), where a red filter was used for GPR6 hybridization and a green filter was used for $OX_1R$ (FIG. 12B) and MC-3 (FIG. 13B). FIGS. 12C and 12D (a magnified version of 12A) are generated by overlay of FIGS. 12A and 12B; co-localization is evidenced by areas having an orange color (from the combination of red and green). Thus, in FIG. 12C, it can be seen that GPR6 and $OX_1R$ are co-localized in a sub-set of cells in the lateral arcuate and in the ventromedial hypothalamic nucleus, both of these regions being involved in the energy homeostasis pathways. A similar overlay-procedure for FIGS. 13A (GPR6) and 13B (MC-3) provides evidence that these receptors are co-localized primarily in the lateral arcuate.

Information continues to develop within the art as to the neural pathways associated with feeding behavior. An important component of this pathway is the neuropeptide agouti-related peptide (AGRP) sometimes referred to as agouti-related transcript (ART). The expression of AGRP is largely restricted to the arcuate nucleus (see Flier, J. S. and Maratos-Flier, E., and FIG. 1 therein). The cells that produce AGRP also produce neuropeptide Y (NPY). Animal studies have evidenced that administration of AGRP and administration of NPY leads to increases in feeding behavior and obesity. AGRP has also been shown to be an antagonist to the melanocortin 4 (MC-4) receptor, and antagonism of the MC-4 receptor is also known to increase feeding behavior an obesity. Thus, AGRP appears to be involved in at least two pathways associated with feeding behavior. As set forth below, it has been discovered that the GPR6 receptor is co-localized within cells that produce AGRP, and based upon the results set forth below in Example 8, coupled with the fact that GPR6 is an endogenous, constitutively activated GPCR, it is apparent that GPR6 is in some manner a potential "regulator" of the system—when expression of the GPR6 receptor is reduced via the use of antisense protocols (Example 9) there was a exceedingly rapid loss in body weight of the animals tested, suggesting that GPR6 may regulate the expression of AGRP.

Figure 14:
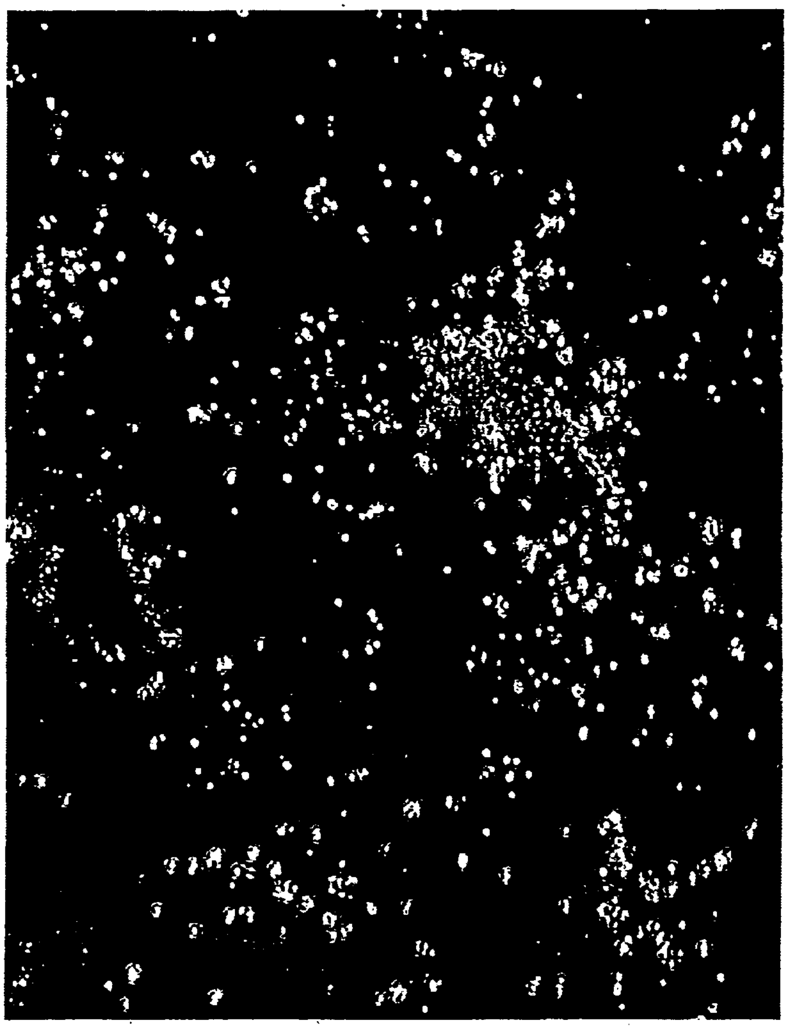
FIG. 14 provides results from co-localization experiment, evidencing that GPR6 and AGRP are co-localized within the arcuate. The arrow directs attention to to a specific cell within the arcuate, with the circle surrounding the cell; the "dots" are radiolabeled GPR6, and beneath those, in a darker shade, is AGRP.

Unlike the "overlay" approach above, the protocol set forth in Marks, D. L. et al, 3 *Mol. & Cell. Neuro.* 395 (1992) was utilized for assessment of co-localization. AGRP (the AGRP cRNA probe was synthesized from a 382 bp fragment of AGRP cDNA cloned into Bluescript SK vector) was analyzed in conjunction with radiolabeled GPR6 and both were found to be co-localized in the arcuate (see FIG. 14). Given the role that AGRP plays with respect to homeostasis, and further given hat GPR6 is constitutively active in its endogenous state, the results obtained from Example 9, infra, would be consistent with these data in that the almost immediate, significant loss of weight can be understood in the context of GPR6 influencing AGRP.

Example 9

Functional Analysis—GPR6 (In Vivo Analysis: GPR6 Antisense)

Based upon the results developed from Example 7, and while not wishing to be bound by any particular theory, it was hypothesized that reduction in the expression of the GPR6 receptor would lead to a reduction in, inter alia, feeding behavior, metabolism, body weight, etc.; thus, by decreasing expression of this receptor via use of an antisense oligonucleotide, it was hypothesized that such animals would evidence changes in functional feeding behavior and/or feeding-related metabolism. Examination of this hypothesis was considered analogous to utilization of an inverse agonist to the receptor in that an inverse agonist would reduce the constitutive activity of the GPR6 receptor, akin to reducing the expression of the receptor itself. It is noted that such an approach results in "knock-down", as opposed to "knock-out", of the receptor, i.e., in general, it is accepted that an antisense approach reduces expression of the target protein by approximately 30%.

Sixteen adult male Sprague-Dawley rats (Harlan, San Diego) were used for this study. Animals were vivarium-acclimated for at least one week prior to use. Animals were housed (groups of two) in hanging plastic cages with food and water available ad lib. Animals were weighed and handled for at least one day prior to surgery (to establish baseline weight) and throughout the study (to assess the effects of the treatment). Daily food intake for pairs of animals in a cage was assessed by weighing the food in the feeding trough each morning before and after refilling. Groups included antisense (n=5), missense (n=4) and sterile water (n=5).

Surgeries were performed under sodium pentobarbital anesthesia (60 mg/kg), supplemented with halothane as necessary. Animals were stereotaxically implanted with a single cannula (brain infusion kit, Alza Pharmaceuticals) aimed at the lateral ventricle (bregma, AP −1.0, Lat −1.5, DV −3.8 from the surface of the brain). The inlet of the cannula was connected via flexible tubing to the outlet of an osmotic minipump (Model 2001, Alza Pharmaceuticals), that was implanted subcutaneously between the shoulder blades according to instructions provided by the manufacturer.

Pumps contained antisense oligonucleotide 5'-GsCTAGCGTTCATCGCCGsC-3' (SEQ.ID.NO.:34; antisense) (wherein the small "s" denotes a phosphorothioate linkage) or missense oligonucleotide 5'-CsTGGACTGTATCGCCCCsG-3' (SEQ.ID.NO.: 35; missense), or sterile water vehicle. Oligonucleotides were synthesized by Genset Corp and diluted to 2 $\mu$g/$\mu$l in sterile water. Because the pumps utilized deliver 1 $\mu$l/hour, animals received 48 $\mu$g/day of antisense or missense oligonucleotides, or 24 $\mu$l/day of sterile water. Pumps were primed prior to implant by incubation in sterile saline at 37° C. for at least four hours prior to implant.

Five days after surgery, animals were treated with d-amphetamine sulfate; six days after surgery, baseline and amphetamine-stimulated locomotor behavior were examined; seven days after surgery, animals were euthanized and brains rapidly removed and frozen for histological analysis.

Animals were taken from the vivarium to the testing room, placed into an open field enclosure (see below), and baseline activity assessed for 30 minutes. At the end of 30 minutes, animals were briefly removed from the enclosure, injected with d-amphetamine sulfate (1.0 mg/kg s.c., diluted in sterile saline; National Institute on Drug Abuse Drug Supply Program), and immediately returned to the enclosure for 150 minutes. Locomotor behavior was quantified at 10 minute intervals in order to follow the time-course of baseline and amphetamine-stimulated activity.

Baseline and amphetamine-stimulated locomotor behavior were assessed in a San Diego Instruments Flex Field System, consisting of 16"×16"×15" clear plexiglas open field enclosures. Photocell arrays (16 in each dimension) which surrounded the open fields were interfaced with a personal computer for collection of data. One array at 2" above the floor of an enclosure detected locomotor activity, and a second at 5" detected rearing behavior. The computer provided a variety of measures of locomotor activity, including total photocell beam breaks, time active, time resting, distance traveled, total number of rears, and time spent rearing (data not shown). During testing, the testing room was dimly lit by an overhead incandescent bulb, with white noise to mask outside sounds.

Figure 15:
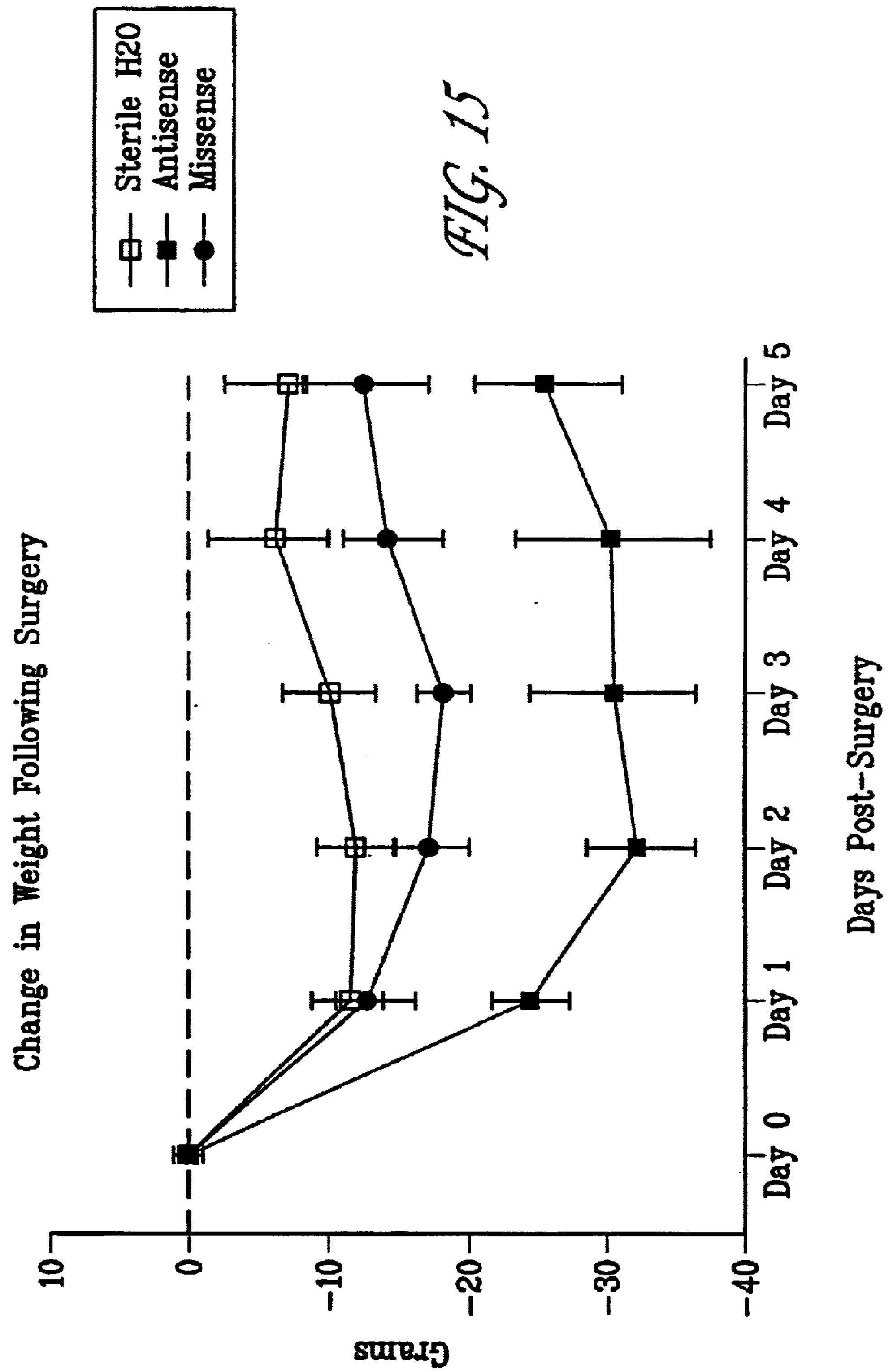
FIG. 15 provides graphic results of body weight over time from animals (n=5) receiving antisense oligonucleotides to GPR6 (star symbol at Day 5 indicates day on which animals received d-amphetamine sulfate injection; see FIG. 16).
Figure 16:
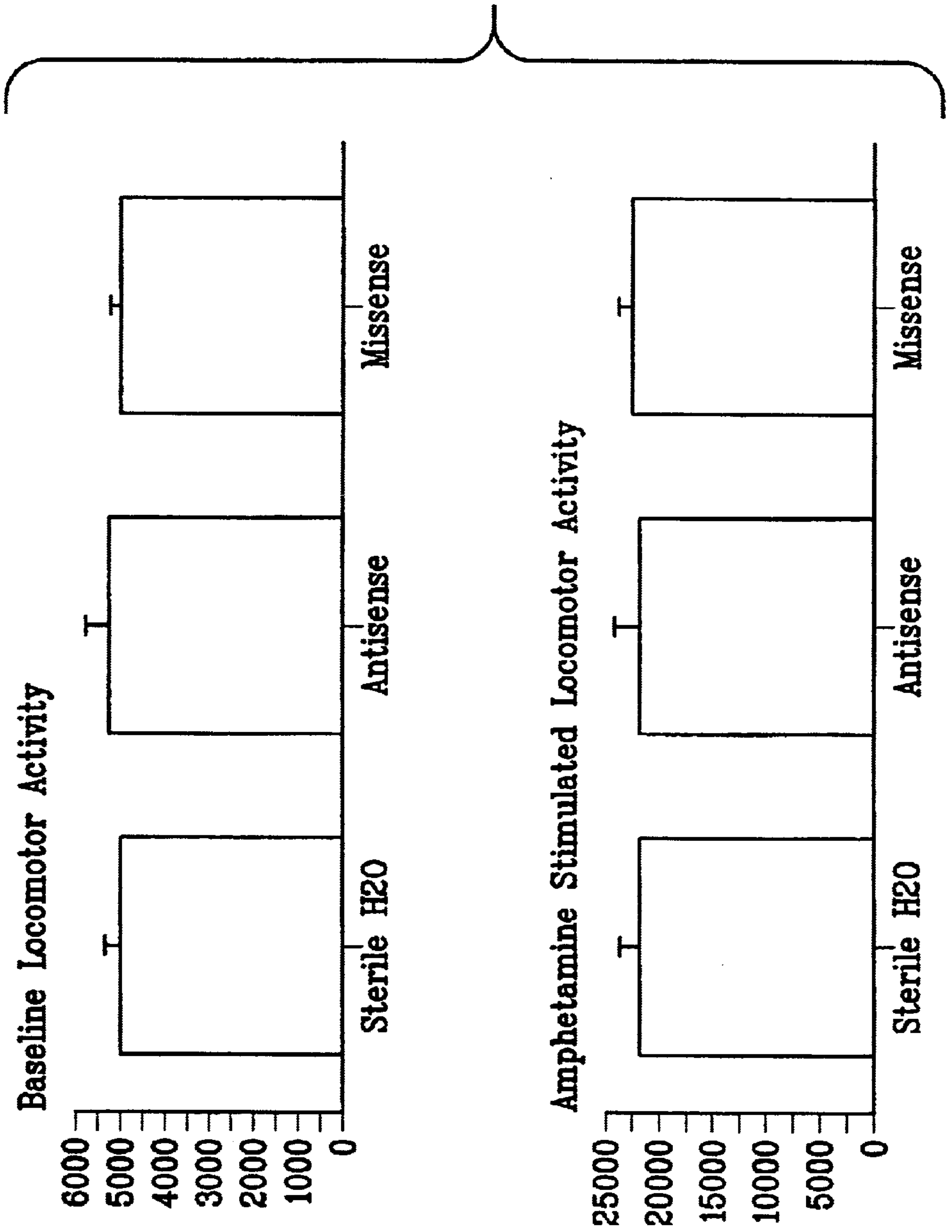
FIG. 16 provides bar graph results from baseline locomotor activity and from amphetamine-induced locomotive behavior in the animals of FIG. 15.

Results are presented in FIGS. 15 and 16. In FIG. 15, it is noted that animals receiving the antisense oligonucleotide (GPR6 "knock-down" animals) had significantly greater loss of weight as compared with either the missense oligonucleotide-treated animals, or the control-treated animals. With respect to locomotor activity, the results of FIG. 16 support the position that the base-line and amphetamine-treatment locomotor activities were substantially the same across all three groups.

Example 10

GPCR Fusion Protein Preparation

The design of the endogenous, constitutively activated GPCR-G protein fusion construct was accomplished as follows: both the 5' and 3' ends of the rat G protein Gsα (long form; Itoh, H. et al., 83 PNAS 3776 (1986)) were engineered to include a HindIII (5'-AAGCTT-3') sequence thereon. Following confirmation of the correct sequence (including the flanking HindIII sequences), the entire sequence was shuttled into pcDNA3.1(−) (Invitrogen, cat. no. V795-20) by subcloning using the HindIII restriction site of that vector. The correct orientation for the Gsα sequence was determined after subcloning into pcDNA3.1(−). The modified pcDNA3.1(−) containing the rat Gsα gene at HindIII sequence was then verified; this vector was now available as a "universal" Gsα protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

Both GPR3-Gsα Fusion Protein construct and GPR6-Gsα Fusion Protein construct were then made as follows: primers were designed for both the GPR3 and GPR6. For GPR3, the primers were as follows:

5'-gatcTCTAGAATGATGTGGGGTGCAGGCAGCC-3' (SEQ. ID. NO. 36; sense)

5'-ctagGGTACCCGGACATCACTGGGGGAGCGGGATC-3' (SEQ. ID. NO. 37, antisense)

The sense and anti-sense primers included the restriction sites for XbaI and KpnI, respectively. For GPR6, the primers were as follows:

5'-gatcTCTAGAATGCAGGGTGCAAATCCGGCC-3' (SEQ. ID. NO. 38, sense)

5'-ctagGGTACCCGGACCTCGCTGGGAGACCTGGAACG-3' (SEQ.ID.NO. 39, antisense).

The sense and anti-sense primers also contained restriction sites for XbaI and KpnI, respectively.

These restriction sites are available upstream of the HindIII site in the pcDNA3.1(−) vector.

PCR was then utilized to secure the respective receptor sequences for fusion within the Gsα universal vector disclosed above, using the following protocol for each: 100 ng cDNA for GPR3 and GPR6 was added to separate tubes containing 2 ul of each primer (sense and anti-sense), 3 uL of 10 mM dNTPs, 10 uL of 10×Taqplus™ Precision buffer, 1 uL of Taqplus™ Precision polymerase (Stratagene: #600211), and 80 uL of water. Reaction temperatures and cycle times for GPR3 were as follows: the initial denaturing step was done it 94° C. for five minutes, and a cycle of 94° C. for 30 seconds; 55° C. for 30 seconds; 72° C. for two minutes (repeated 30 times for GPR3). A final extension time was done at 72° C. for ten minutes. For GPR6, the initial denaturing step was done at 96° C. for seven minutes, and a cycle of 96° C. for 30 seconds, 55° C. for 30 seconds, and 72° C. for two minutes was repeated 30 times. A final extension time of ten minutes at 72° C. was done for GPR6. Both PCR products for GPR3 and GPR6 were ran on a 1% agarose gel and then purified (data not shown). Each purified product was digested with XbaI and KpnI (New England Biolabs) and the desired inserts were isolated, purified and ligated into the Gs universal vector at the respective restriction site. The positive clones were isolated following transformation and determined by restriction enzyme digest; expression using 293 cells was accomplished following the protocol set forth infra. Each positive clone for GPR3:Gs—Fusion Protein and GPR6:Gs—Fusion Protein was sequenced and made available for the direct identification of candidate compounds.

GPCR Fusion Proteins were analyzed as above and verified to be constitutively active (data not shown).

Example 11

Protocol: Direct Identification of Inverse Agonists and Agonists Using [$^{35}$S]GTPγS Although we have utilized endogenous, constitutively active GPCRs for the direct identification of candidate compounds as, e.g., inverse agonists, for reasons that are not altogether understood, intra-assay variation can become exacerbated. Preferably, then, a GPCR Fusion Protein, as disclosed above, is utilized. We have determined that when such a protein is used, intra-assay variation appears to be substantially stabilized, whereby an effective signal-to-noise ratio is obtained. This has the beneficial result of allowing for a more robust identification of candidate compounds.

It is important to note that the following results have been obtained using an orphan receptor; as that data support, it is possible, using the techniques disclosed herein, to directly identify candidate compounds that modulate the orphan receptor as inverse agonists, agonists and partial agonists, directly from a primary screen; indeed, the methods disclosed herein are sensitive enough to allow for direct identification of both inverse agonist and agonist modulators on the same assay plate.

1. Membrane Preparation

Membranes comprising the endogenous, constitutively active orphan GPCR fusion protein of interest (see Examples 2 and 10) and for use in the direct identification of candidate compounds as inverse agonists, agonists or partial agonists were prepared as follows:

(a) Materials

Membrane Scrape Buffer was comprised of 20 mM HEPES and 10 mM EDTA, pH 7.4; Membrane Wash Buffer was comprised of 20 mM HEPES and 0.1 mM EDTA, pH 7.4; Binding Buffer was comprised of 20 mM HEPES, 100 mM NaCl, and 10 mM $MgCl_2$, pH 7.4

(b) Procedure

All materials were kept on ice throughout the procedure. Firstly, the media was aspirated from a confluent monolayer of cells, followed by rinse with 10 ml cold PBS, followed by aspiration. Thereafter, 5 ml of membrane Scrape Buffer was added to scrape cells; this was followed by transfer of cellular extract into 50 ml centrifuge tubes (centrifuged at 20,000 rpm for 17 minutes at 40° C.). Thereafter, the supernatant was aspirated and the pellet was resuspended in 30 ml Membrane Wash Buffer followed by centrifuge at 20,000 rpm for 17 minutes at 4° C. The supernatant was then aspirated and the pellet resuspended in Binding Buffer. This was then homogenized using a Brinkman polytron™ homogenizer (15–20 second bursts until the all material was in suspension). This is referred to herein as "Membrane Protein".

2. Bradford Protein Assay

Following the homogenization, protein concentration of the membranes was determined using the Bradford Protein Assay (protein can be diluted to about 1.5 mg/ml, aliquoted and frozen (−80° C.) for later use; when frozen, protocol for use is as follows: on the day of the assay, frozen Membrane Protein is thawed at room temperature, followed by vortex and then homogenized with a polytron at about 12×1,000 rpm for about 5–10 seconds; it is noted that for multiple preparations, the homogenizer should be thoroughly cleaned between homoginezation of different preparations).

(a) Materials

Binding Buffer (as per above); Bradford Dye Reagent; Bradford Protein Standard were utilized, following manufacturer instructions (Biorad, cat. no. 500-0006).

(b) Procedure

Duplicate tubes were prepared, one including the membrane, and one as a control "blank". Each contained 800 ul Binding Buffer. Thereafter, 10 ul of Bradford Protein Standard (1 mg/ml) was added to each tube, and 10 ul of membrane Protein was then added to just one tube (not the blank). Thereafter, 200 ul of Bradford Dye Reagent was added to each tube, followed by vortex of each. After five (5) minutes, the tubes were re-vortexed and the material therein was transferred to cuvettes. The cuvettes were then read using a CECIL 3041 spectrophotometer, at wavelength 595.

3. Direct Identification Assay (a) Materials

GDP Buffer consisted of 37.5 ml Binding Buffer and 2 mg GDP (Sigma, cat. no. G-7127), followed by a series of dilutions in Binding Buffer to obtain 0.2 uM GDP (final concentration of GDP in each well was 0.1 uM GDP); each well comprising a candidate compound, had a final volume of 200 ul consisting of 100 ul GDP Buffer (final concentration, 0.1 uM GDP), 50 ul Membrane Protein in Binding Buffer, and 50 ul [$^{35}$S]GTPγS (0.6 nM) in Binding Buffer (2.5 ul [$^{35}$S]GTPγS per 10 ml Binding Buffer).

(b) Procedure

Candidate compounds (Tripos, Inc., St. Louis, Mo.) were received in 96-well plates (these can be frozen at −80° C.). Membrane Protein (or membranes with expression vector excluding the GPCR Fusion Protein, as control), were homogenized briefly until in suspension. Protein concentration was then determined using the Bradford Protein Assay set forth above. Membrane Protein (and control) was then diluted to 0.25 mg/ml in Binding Buffer (final assay concentration, 12.5 ug/well). Thereafter, 100 ul GDP Buffer was added to each well of a Wallac Scintistrip™ (Wallac). A 5 ul pin-tool was then used to transfer 5 ul of a candidate compound into such well (i.e., 5 ul in total assay volume of 200 ul is a 1:40 ratio such that the final screening concentration of the candidate compound is 10 uM). Again, to avoid contamination, after each transfer step the pin tool was rinsed in three reservoirs comprising water (1×), ethanol (1×) and water (2×)-excess liquid should be shaken from the tool after each rinse and dried with paper and kimwipes. Thereafter, 50 ul of Membrane Protein is added to each well (a control well comprising membranes without the GPCR Fusion Protein is also utilized), and pre-incubated for 5–10 minutes at room temperature (the plates were covered with foil in that the candidate compounds obtained from Tripos are light sensitive). Thereafter, 50 ul of [$^{35}$S]GTPγS (0.6 nM) in Binding Buffer was added to each well, followed by incubation on a shaker for 60 minutes at room temperature (again, in this example, plates were covered with foil). The assay was then stopped by spinning of the plates at 4000 RPM for 15 minutes at 22° C. The plates were then aspirated with an 8 channel manifold and sealed with plate covers. The plates were then read on a Wallacc 1450 using setting "Prot. #37" (as per manufacturer instructions).

Figure 17A:
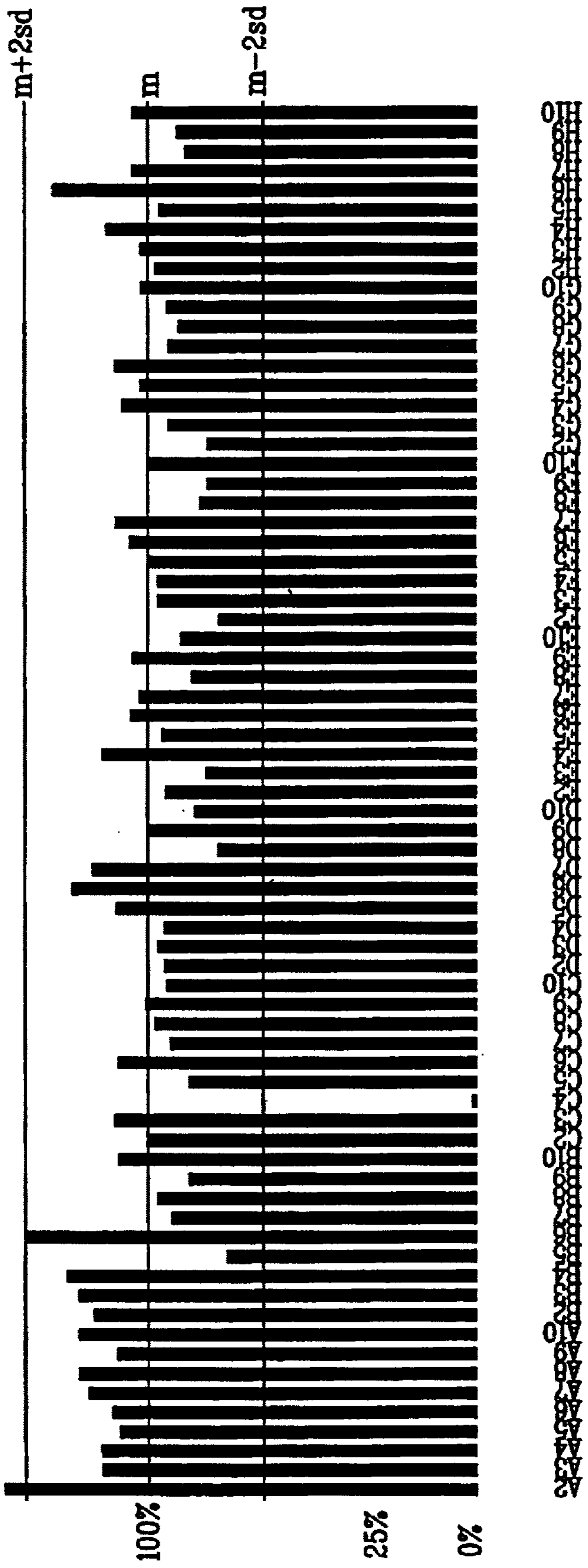
FIG. 17 provides bar-graph results from the direct identification of candidate compounds screened against GPR3 Fusion Protein (FIG. 17A) and GPR6 Fusion Protein (FIG. 17B).
Figure 17B:
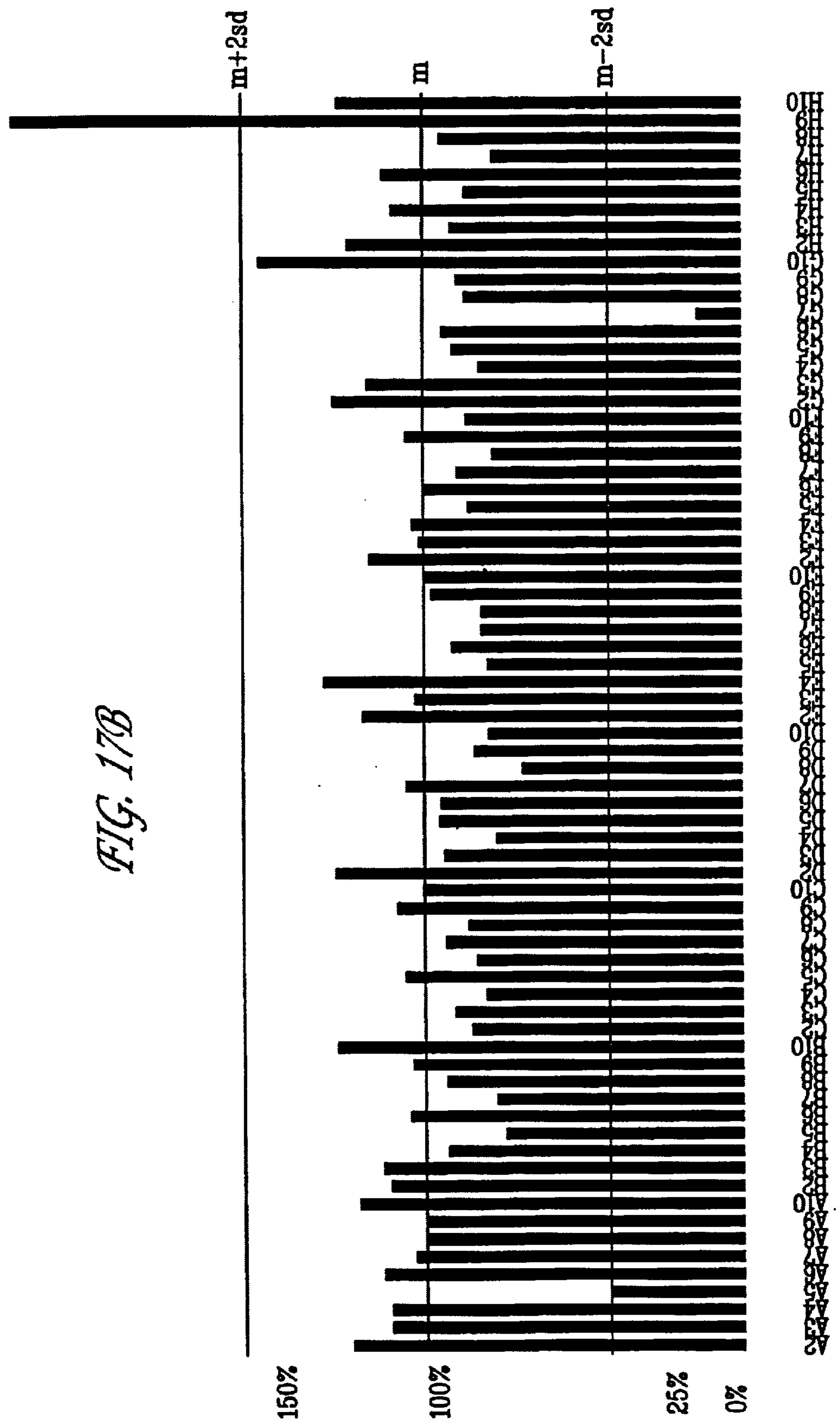
Figure 18A:
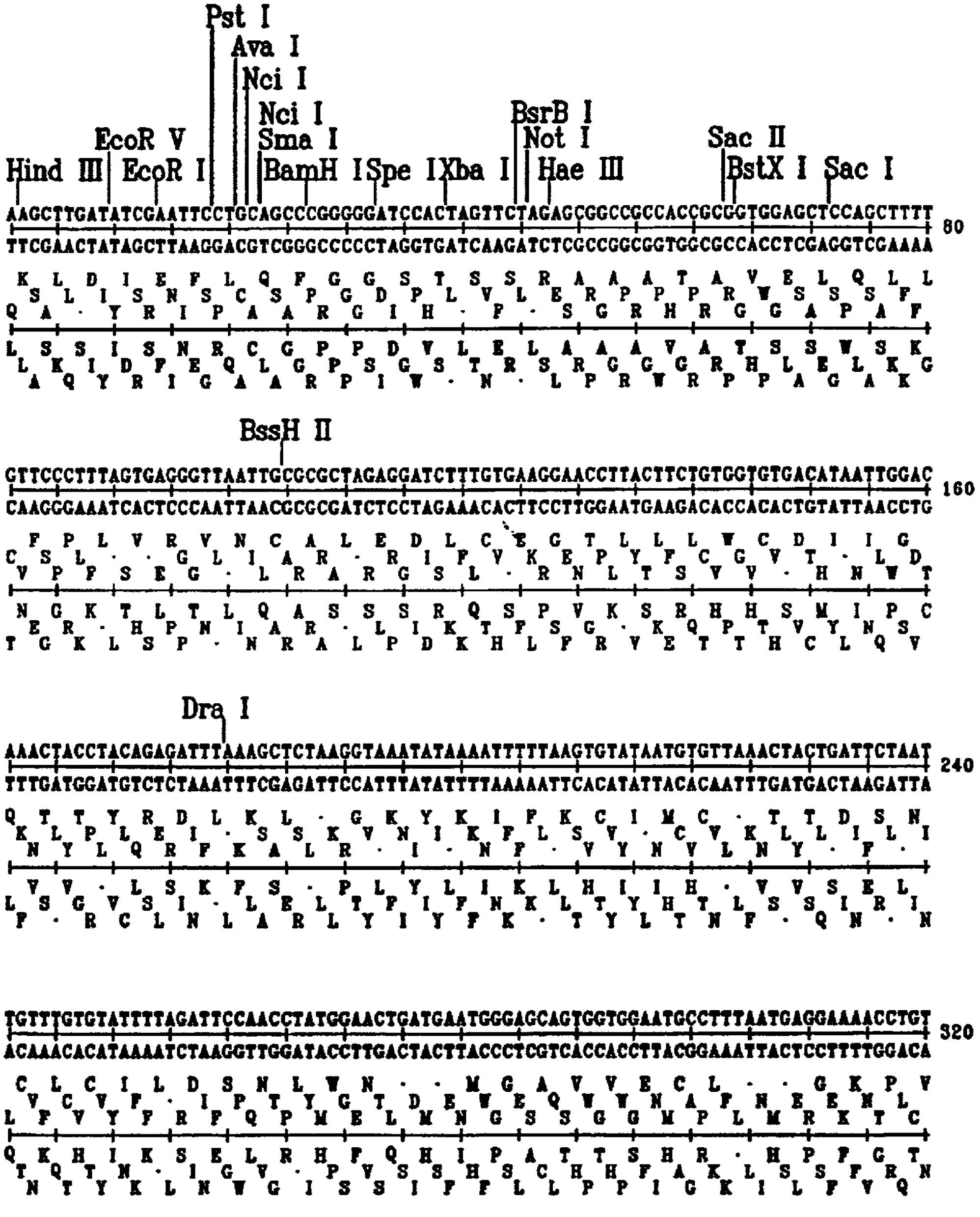
Figure 18B:
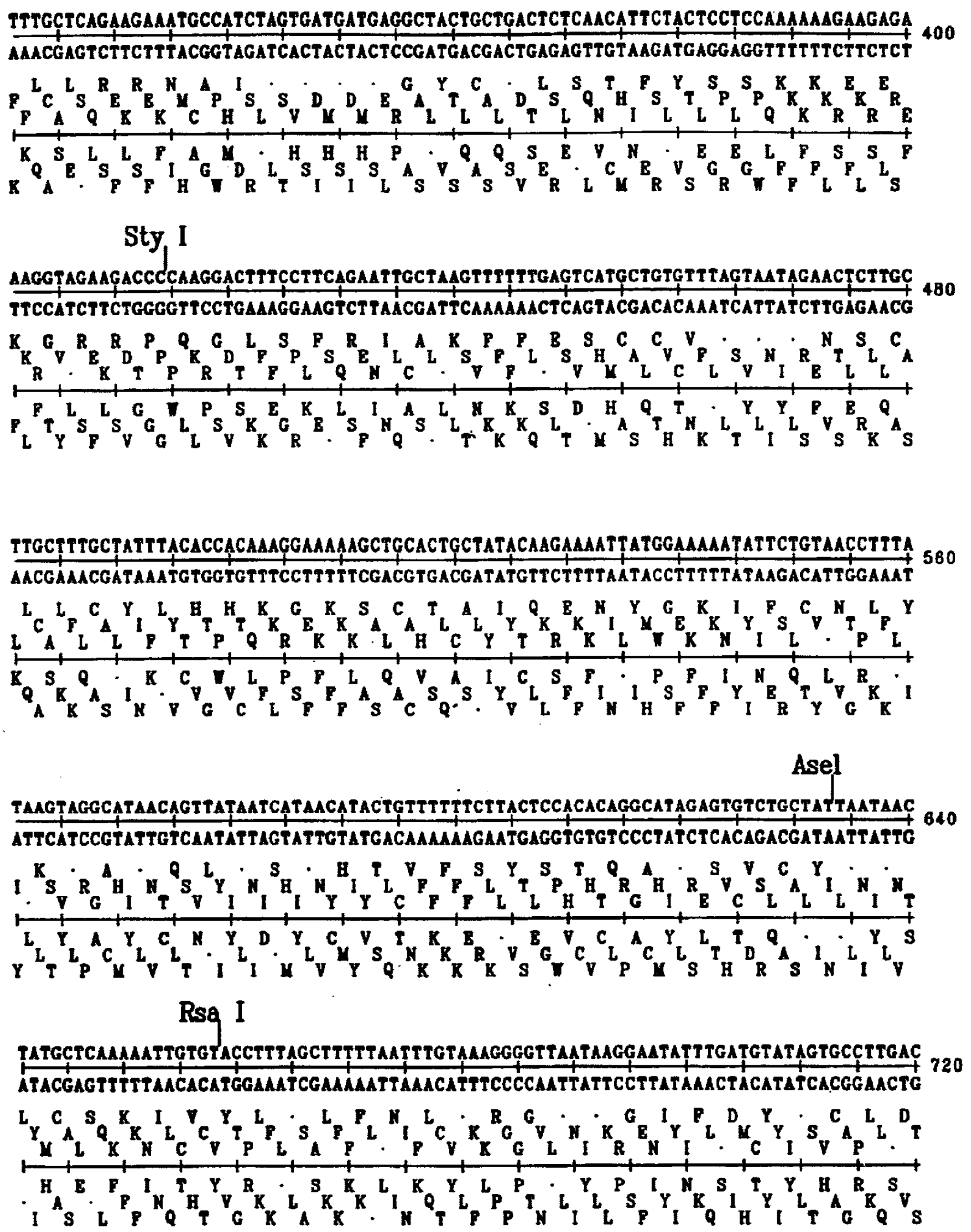
Figure 18C:
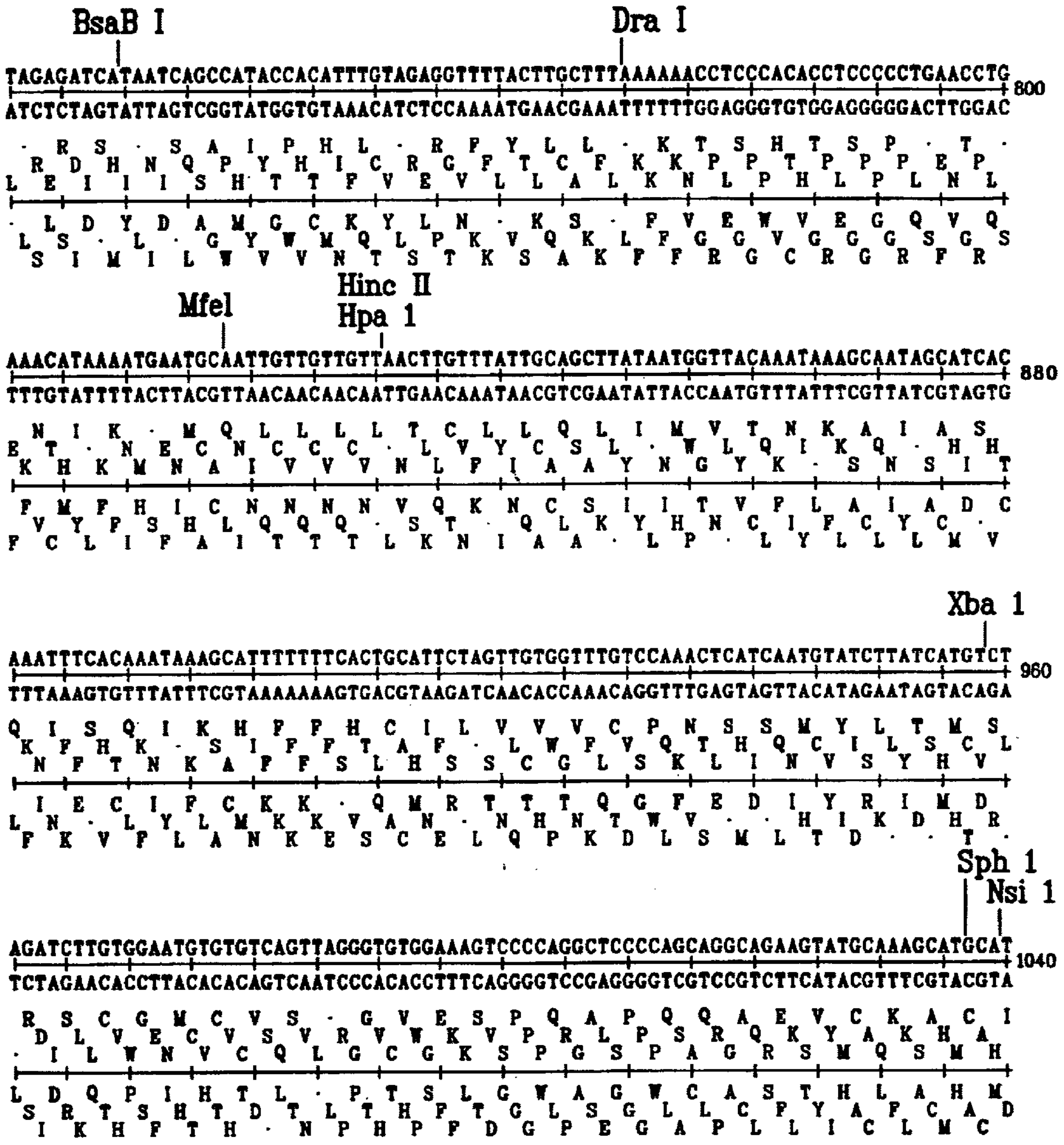
Figure 18D:
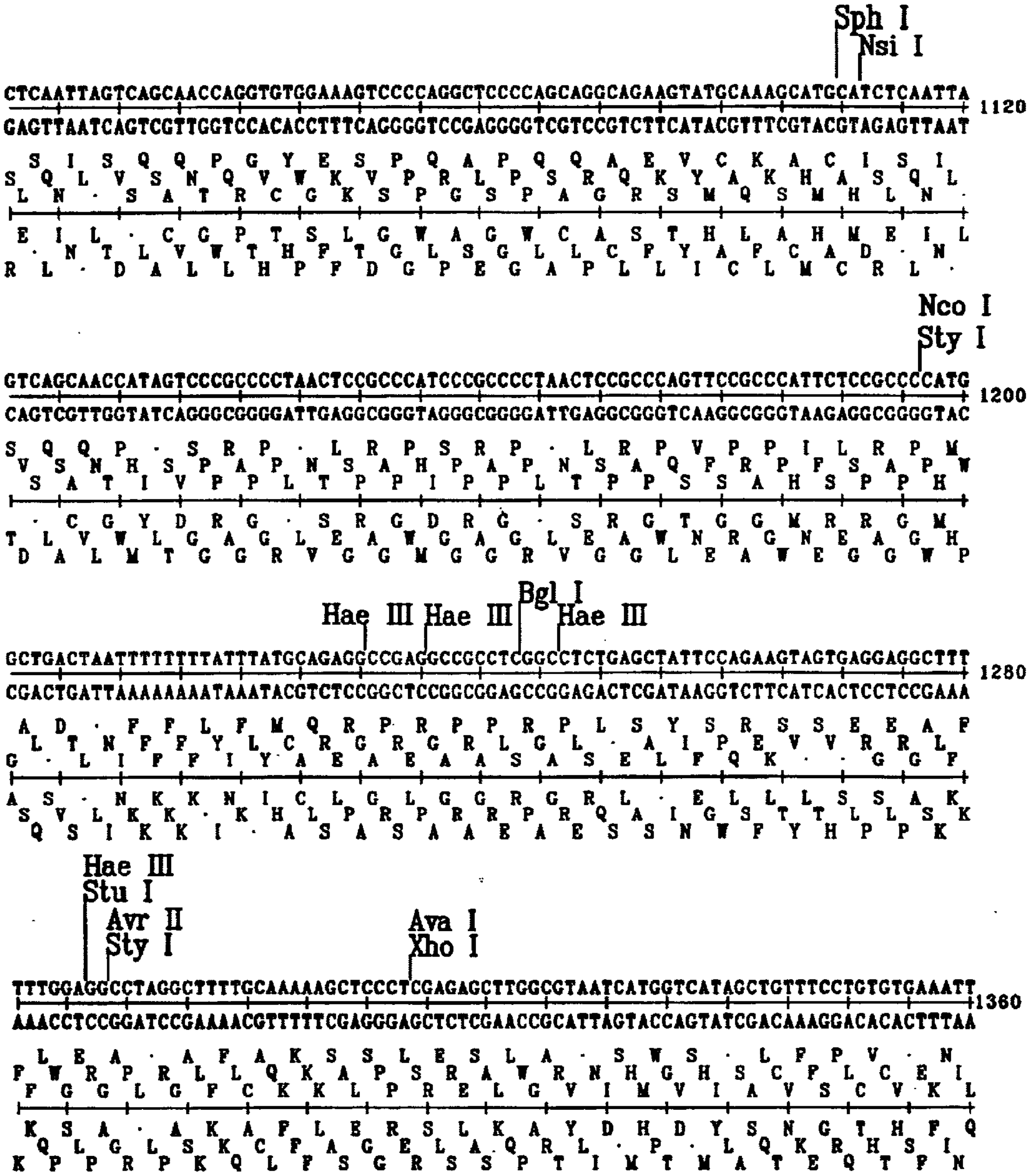
Figure 18E:
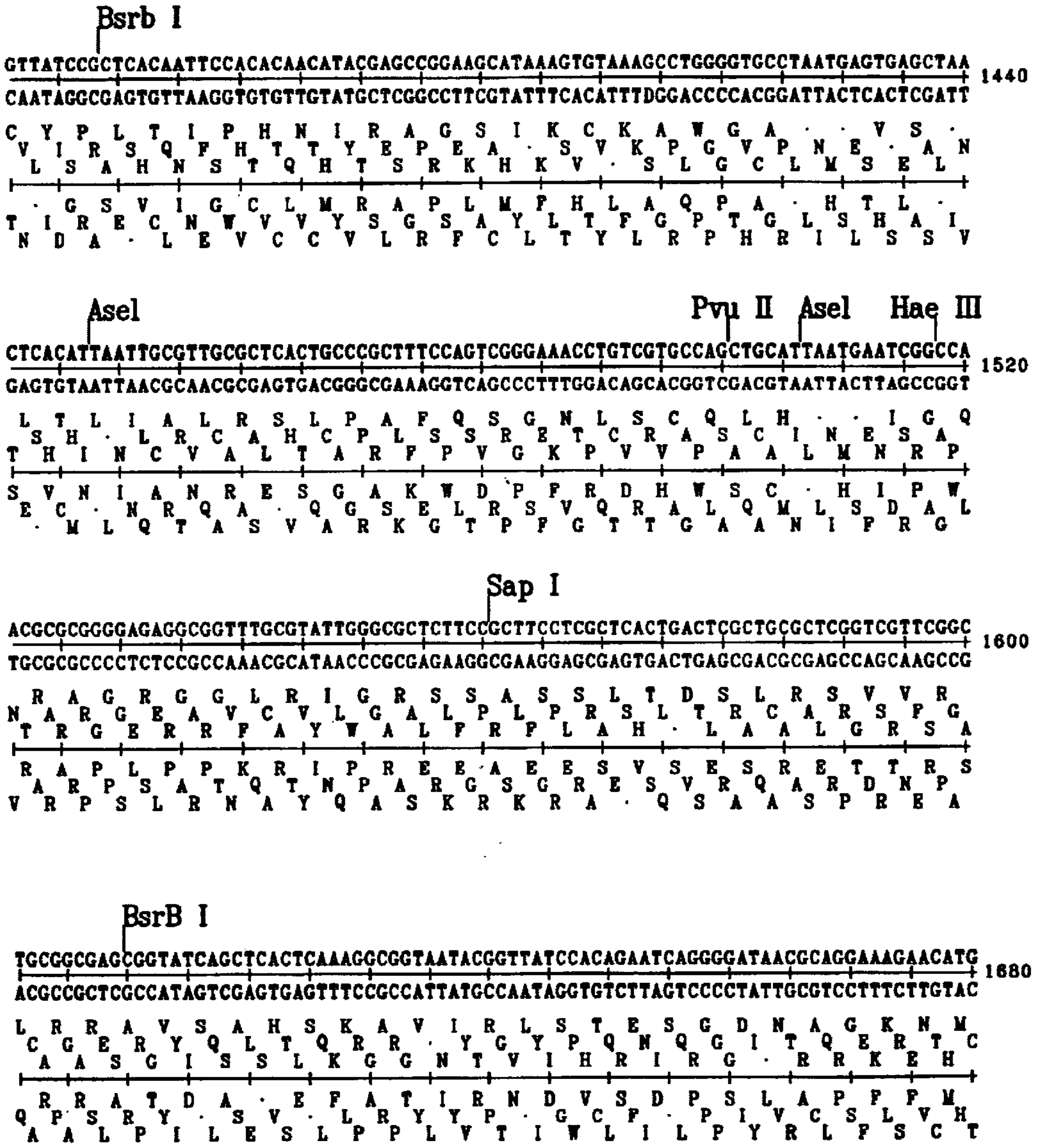
Figure 18F:
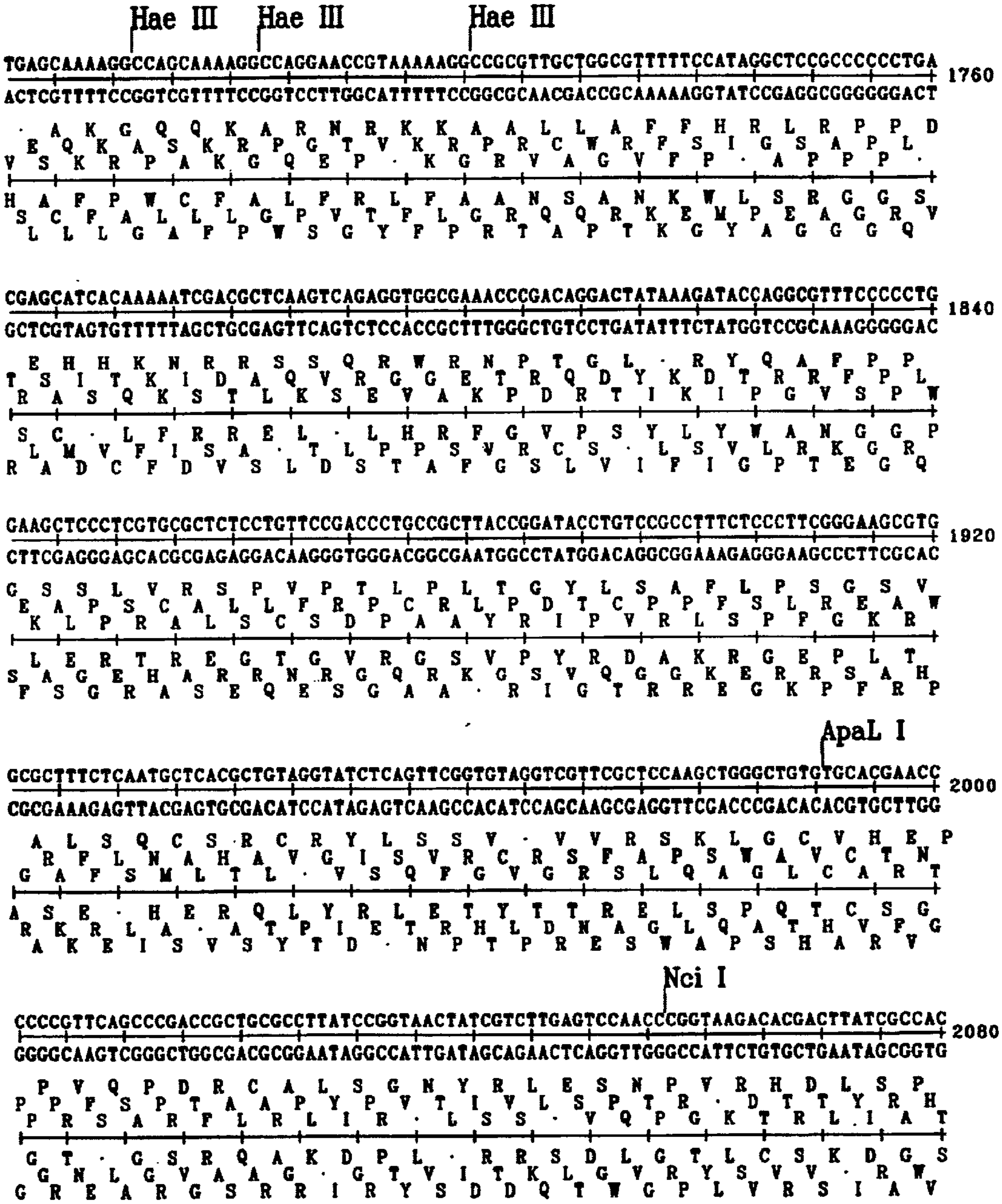
Figure 18G:
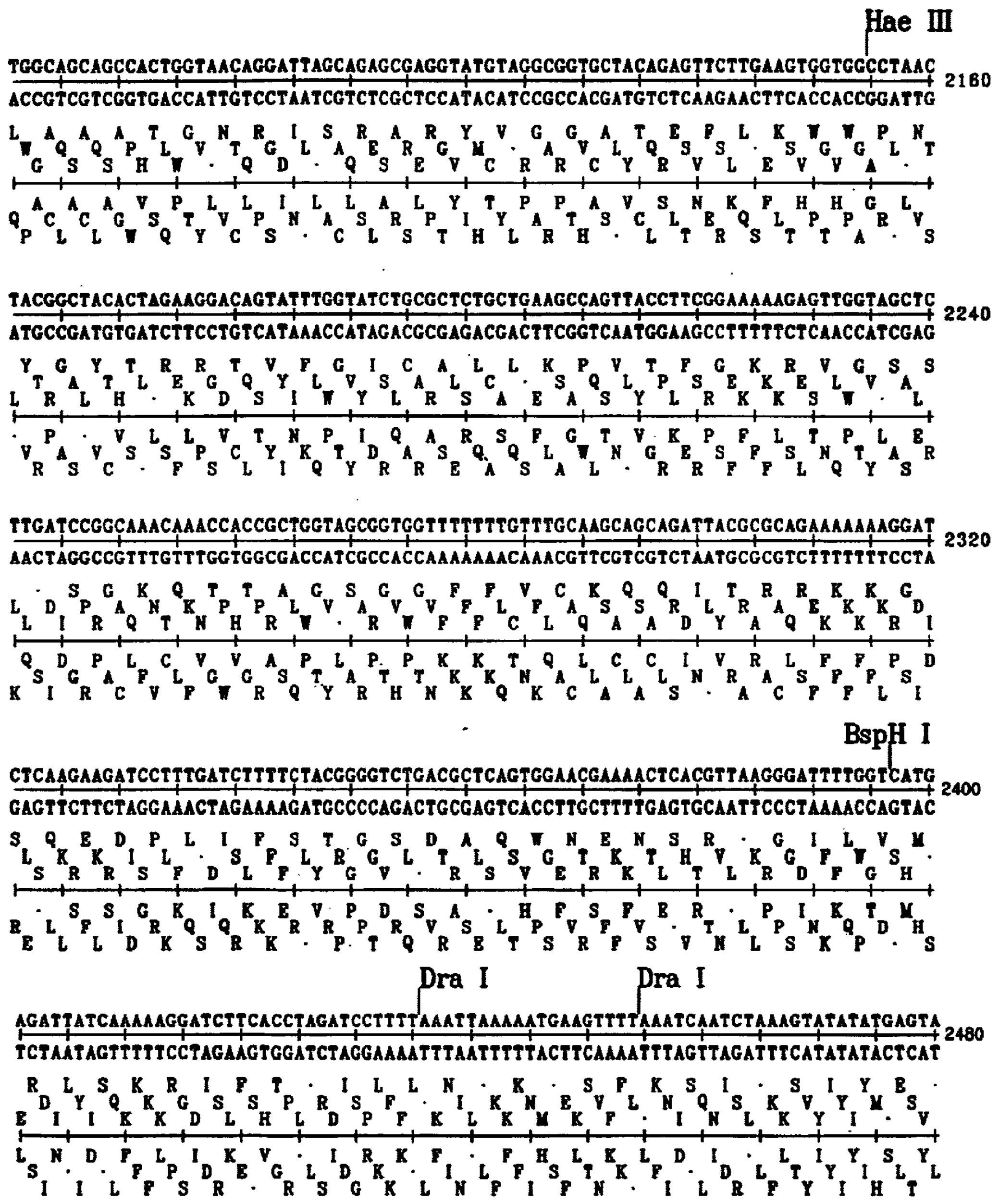
Figure 18H:
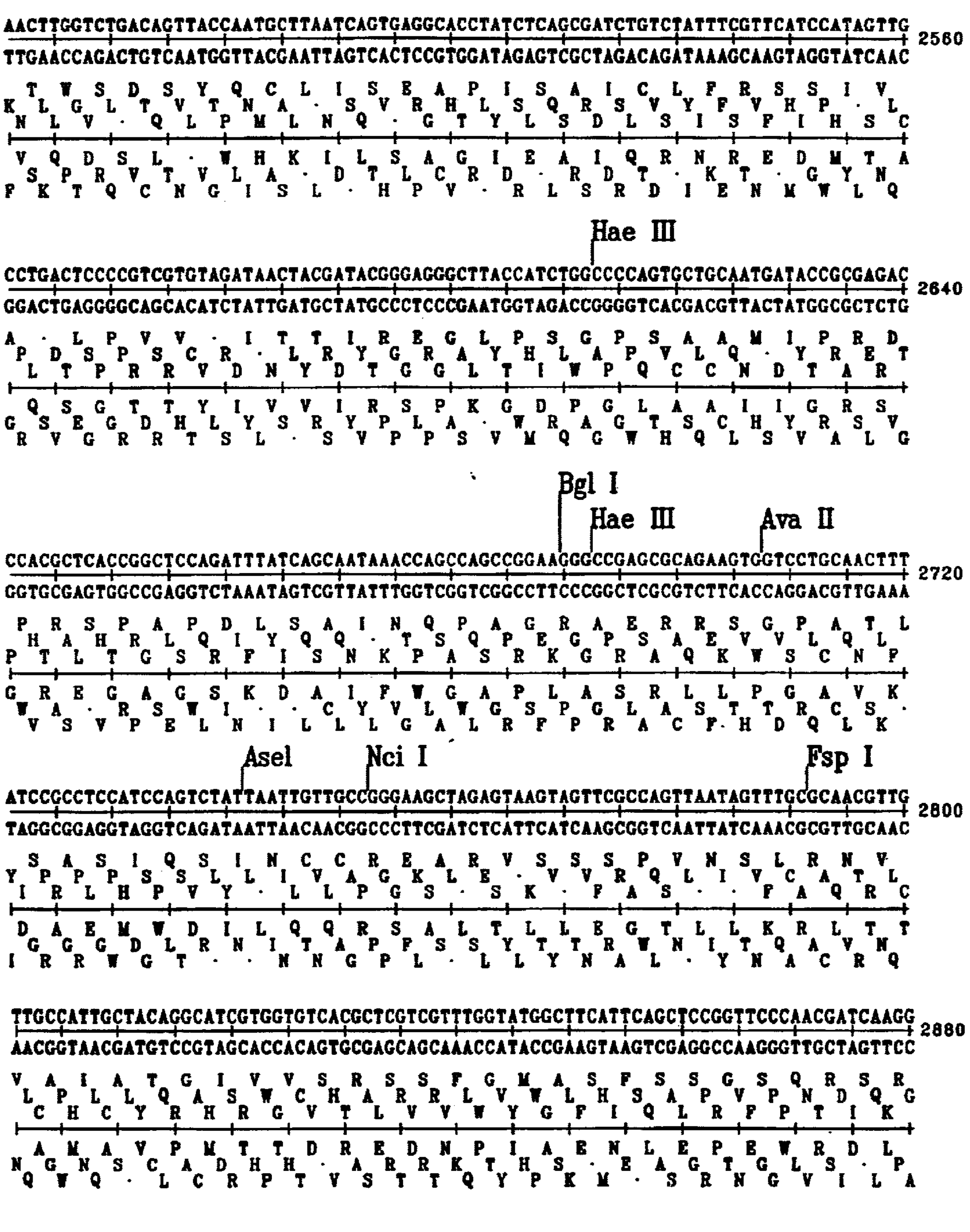
Figure 18I:
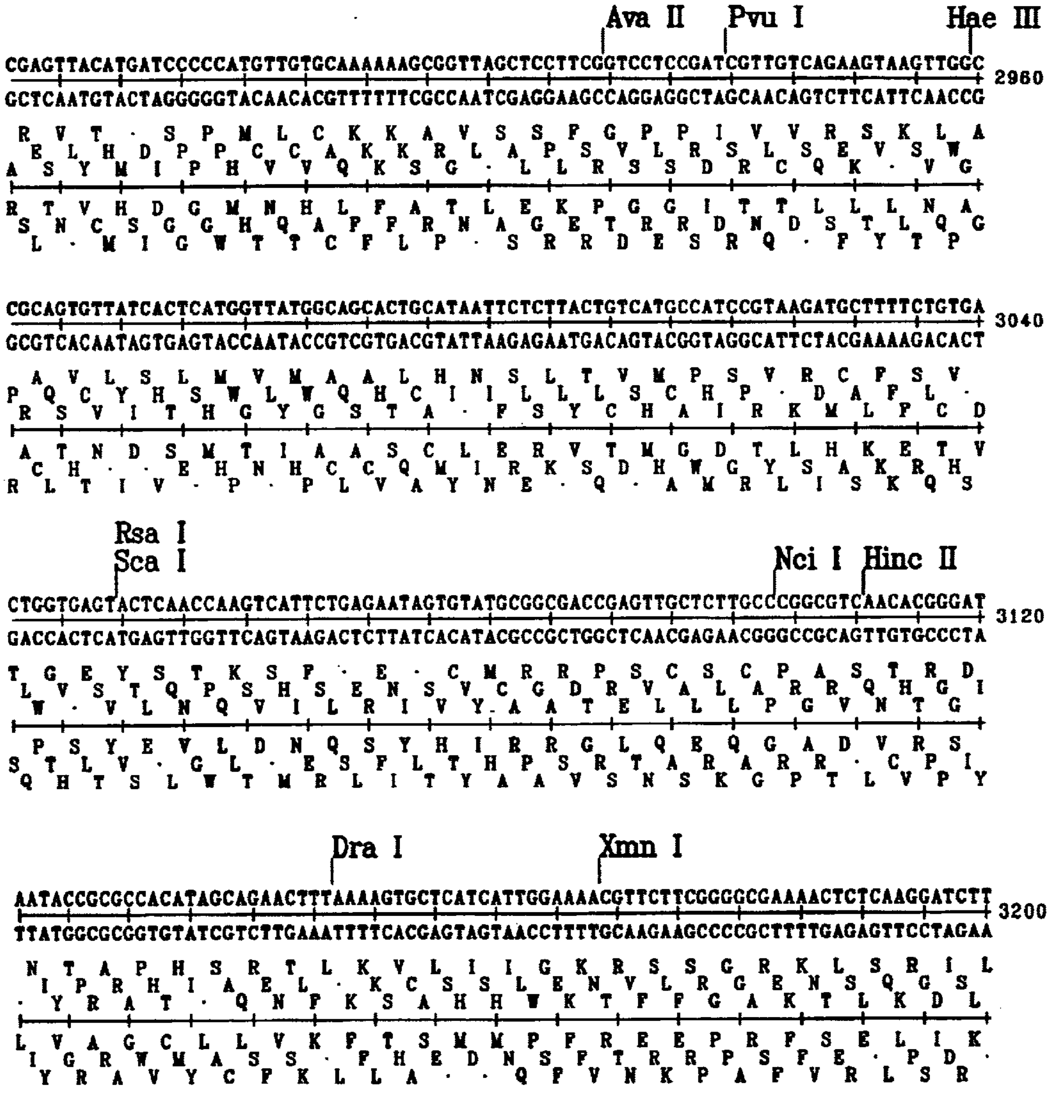
Figure 18K:
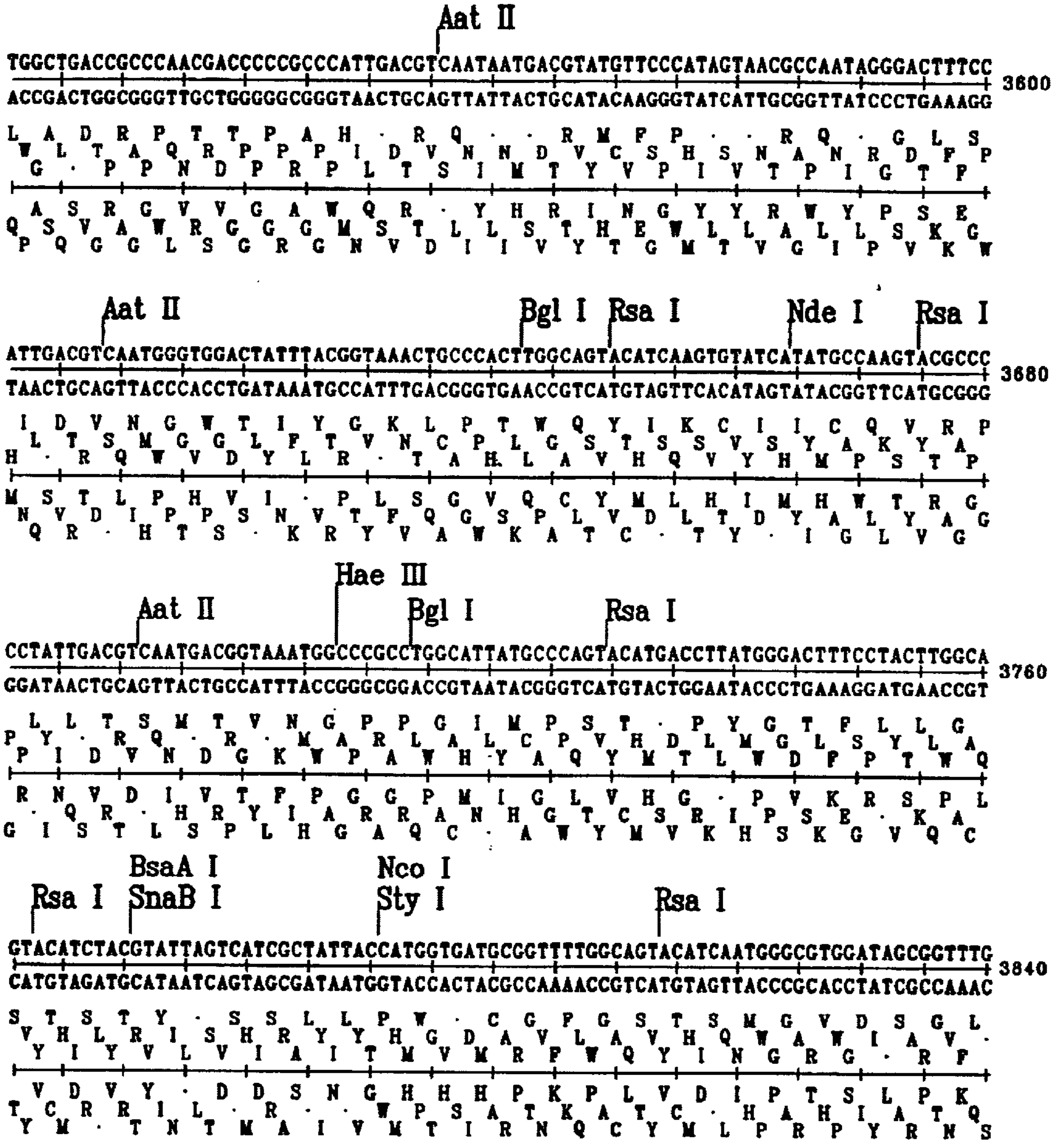

Exemplary results are presented in FIG. 17A (GPR3: Gs Fusion Protein) and FIG. 17B (GPR6:Gs Fusion Protein) where each designation is a well comprising a different candidate compound, standard deviations based upon the mean results of each plate are in dashed lines and the vertical lines are the percent response. Note in FIG. 17A well designation C4—this compound was directly identified as an inverse agonist to the GPR3 receptor. Note in FIG. 17B wells designated G7 and H9—these compounds were directly identified as an inverse agonist and a agonist, respectively, to the GPR6 receptor. In both cases, these are orphan receptors.

It is preferred that following such direct identification, $IC_{50}$ (inverse agonist) or $EC_{50}$ (agonist) values be determined; those having ordinary skill in the art are credited with utilizing $IC_{50}$ and $EC_{50}$ assay protocols of choice.

Example 12

Protocol: Confirmation Assay

After using an independent assay approach to provide a directly identified candidate compound as set forth above, it is preferred that a confirmation assay then be utilized. In this case, the preferred confirmation assay is a cyclase-based assay.

A modified Flash Plate™ Adenylyl Cyclase kit (New England Nuclear; Cat. No. SMP004A) was utilized for confirmation of candidate compounds directly identified as inverse agonists and agonists to endogenous, constitutively activated orphan GPCRs in accordance with the following protocol.

Transfected cells were harvested approximately three days after transfection. Membranes were prepared by homogenization of suspended cells in buffer containing 20 mM HEPES, pH 7.4 and 10 mM $MgCl_2$. Homogenization was performed on ice using a Brinkman Polytron™ for approximately 10 seconds. The resulting homogenate was centrifuged at 49,000×g for 15 minutes at 4° C. The resulting pellet was then resuspended in buffer containing 20 mM HEPES, pH 7.4 and 0.1 mM EDTA, homogenized for 10 seconds, followed by centrifugation at 49,000×g for 15 minutes at 4° C. The resulting pellet can be stored at −80° C. until utilized. On the day of direct identification screening, the membrane pellet is slowly thawed at room temperature, resuspended in buffer containing 20 mM HEPES, pH 7.4 and 10 mM $MgCl_2$, to yield a final protein concentration of 0.60 mg/ml (the resuspended membranes are placed on ice until use).

cAMP standards and Detection Buffer (comprising 2 μCi of tracer [$^{125}$IcAMP (100 μl] to 11 ml Detection Buffer) were prepared and maintained in accordance with the manufacturer's instructions. Assay Buffer was prepared fresh for screening and contained 20 mM HEPES, pH 7.4, 10 mM $MgCl_2$, 20 mM phospocreatine (Sigma), 0.1 units/ml creatine phosphokinase (Sigma), 50 μM GTP (Sigma), and 0.2 mM ATP (Sigma); Assay Buffer can be stored on ice until utilized.

Candidate compounds identified as per above (if frozen, thawed at room temperature) were added to plate wells (3 μl/well; 12 μM final assay concentration), together with 40 μl Membrane Protein (30 μg/well) and 50 μl of Assay Buffer. This admixture was then incubated for 30 minutes at room temperature, with gentle shaking.

Following the incubation, 100 μl of Detection Buffer was added to each well, followed by incubation for 2–24 hours. Plates were then counted in a Wallac MicroBeta™ plate reader using "Prot. #31" (as per manufacturer instructions).

Although a variety of expression vectors are available to those in the art, it is most preferred that the vector utilized be pCMV. This vector has been deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The vector was tested by the ATCC and determined to be viable. The ATCC has assigned the following deposit number to pCMV: ATCC #203351. A diagram of pCMV (including restriction sites) is set forth in FIG. 18.

It is intended that each of the patents, applications, and printed publications mentioned in this patent document be hereby incorporated by reference in their entirety. As those skilled in the art will appreciate, numerous changes and modifications may be made to the preferred embodiments of the invention without departing from the spirit of the invention. It is intended that all such variations fall within the scope of the invention.

Appendix A

FIG. 3 Grid Code

A2—amygdala; A3—caudate nucleus; A4—cerebellum; A5—cerebral cortex; A6—frontal cortex;
A7—hippocampus; A8—medulla oblongata
B1—occipital cortex; B2—putamen; B3—substantia nigra; B4—temporal cortex; B5—thalamus;
B6—sub-thalamic nucleus; B7—spinal cord
C1—heart; C2—aorta; C3—skeletal muscle; C4—colon; C5—bladder; C6—uterus; C7—prostate; C8—stomach
D1—testis; D2—ovary; D3—pancreas; D4—pituitary gland; D5—adrenal gland; D6—thyroid;
D7—salivary gland; D8—mammary gland
E1—kidney; E2—liver; E3—small intestine; E4—spleen; E5—thymus; E6—peripheral leukocyte;
E8—lymph node; E9—bone marrow
F1—tonsil; F2—lung; F3—trachea; F4—placenta
G1—fetal brain; G2—fetal heart; G3—fetal kidney; G4—fetal liver; G5—fetal spleen; G6—fetal thymus; G8—fetal lung

What is claimed is:

1. A method for identifying one or more compounds as an agonist or inverse agonist of an endogenous, constitutively active G protein coupled cell surface receptor, wherein the endogenous ligand for said receptor has not been identified, comprising the steps of:

(a) providing a GPCR Fusion Protein, said GPCR Fusion Protein comprising:

(i) an endogenous, constitutively active G protein coupled cell surface receptor, wherein the endogenous ligand for said receptor has not been identified; and (ii) a Gsα protein;

(b) contacting said GPCR Fusion Protein with one or more candidate compounds;

(c) measuring the ability of said compound to inhibit or stimulate the activity of said receptor; and (d) identifying one or more of said compounds to be agonist or inverse agonist of said receptor, wherein said compound is identified as an agonist by stimulating the activity of said receptor, and said inverse agonist is identified by inhibiting the activity of said receptor.

2. The method of claim 1, wherein one or more of said compounds are directly identified as an inverse agonist to said receptor.

3. The method of claim 1, wherein one or more of said compounds are directly identified as an agonist to said receptor.

* * * * *